| 
US011492645B2

(12) United States Patent
Liu et al.

(10) Patent No.: US 11,492,645 B2
(45) Date of Patent: Nov. 8, 2022

(54) COMPOSITION AND USE OF CAS PROTEIN INHIBITORS

(71) Applicant: ShanghaiTech University, Shanghai (CN)

(72) Inventors: Jia Liu, Shanghai (CN); Biao Jiang, Shanghai (CN); Peixiang Ma, Shanghai (CN); Guang Yang, Shanghai (CN)

(73) Assignee: ShanghaiTech University, Shanghai (CN)

( * ) Notice: Subject to any disclaimer, the term of this patent is extended or adjusted under 35 U.S.C. 154(b) by 0 days.

(21) Appl. No.: 17/272,252

(22) PCT Filed: Aug. 29, 2019

(86) PCT No.: PCT/CN2019/103203
§ 371 (c)(1),
(2) Date: Feb. 26, 2021

(87) PCT Pub. No.: WO2020/043148
PCT Pub. Date: Mar. 5, 2020

(65) Prior Publication Data
US 2021/0317480 A1    Oct. 14, 2021

(30) Foreign Application Priority Data

Aug. 29, 2018  (WO) ................ PCT/CN2018/102908

(51) Int. Cl.
| | |
|---|---|
| *C12N 15/63* | (2006.01) |
| *A61K 31/70* | (2006.01) |
| *C12N 15/90* | (2006.01) |
| *A61K 31/7088* | (2006.01) |
| *A61K 38/16* | (2006.01) |
| *A61K 38/46* | (2006.01) |
| *A61K 38/50* | (2006.01) |
| *C12N 7/00* | (2006.01) |
| *A01K 67/00* | (2006.01) |

(52) U.S. Cl.
CPC ........ *C12N 15/902* (2013.01); *A61K 31/7088* (2013.01); *A61K 38/162* (2013.01); *A61K 38/465* (2013.01); *A61K 38/50* (2013.01); *C12N 7/00* (2013.01); *C12N 2795/14123* (2013.01); *C12N 2795/14143* (2013.01)

(58) Field of Classification Search
CPC .............. C12N 15/902; C12N 2310/20; C12N 2795/14122; C12N 2795/14143; A61K 31/7088
See application file for complete search history.

(56) References Cited

U.S. PATENT DOCUMENTS 5,658,727 A * 8/1997 Barbas et al.
8,252,324 B2   8/2012 Petrenko et al.
8,685,893 B2   4/2014 Sidhu et al.
8,969,253 B2   3/2015 Reiersen et al.
2008/0096769 A1 4/2008 Quay et al.
2015/0064138 A1* 3/2015 Lu et al.
2021/0363206 A1* 11/2021 Blackburn-Marino et al.

FOREIGN PATENT DOCUMENTS

| WO | WO 2014184528 A1 | 11/2014 |
| WO | 2015/200519 | 12/2015 |
| WO | WO 2017077275 A1 | 5/2017 |

OTHER PUBLICATIONS

Karimi et al. Bacteriophages and phage-inspired nanocarriers for targeted delivery of therapeutic cargos. Advanced Drug Delivery Reviews 106:45-62, (Year: 2016).*
Harrington et al. A broad-spectrum inhibitor of CRISPR-Cas9. Cell 170:1224-1233, (Year: 2017).*
Rauch et al. Inhibition of CRISPR-Cas9 with bacteriophage proteins. Cell 168:150-158, (Year: 2017).*
Shin et al. Disabling Cas9 by an anti-CRISPR DNA mimic. Sci. Adv. 3:e1701620, 9 pages, (Year: 2017).*
Hay et al. Filamentous phages: masters of a microbial sharing economy. EMBO reports 20:e47427, 24 pages; (Year: 2019).*
International Search Report for PCT/CN2019/103203, International Filing Date Aug. 29, 2019, 5 pages.
Written Opinion for PCT/CN2019/103203, International Filing Date Aug. 29, 2019, dated Dec. 10, 2019, 4 pages.
Fiester SE et al. "Liquid crystal properties of a self-assembling viral coat protein" *Liquid Crystals*, vol. 38, No. 9, Sep. 9, 2011 (Sep. 9, 2011). pp. 1153-1157.
European Search Report and Opinion dated Jun. 22, 2022 for EP Application No. 19854174.0. 9 pages.
Cui, et al. Allosteric inhibition of CRISPR-Cas9 by bacteriophage-derived peptides. Genome Biology. 2020; 21, Article No. 51. 15 pages.
Pederson, et al. The protein capsid of filamentous bacteriophage PH75 from Thermus thermophilus. Journal of Molecular biology. Jun. 2001; 309(2):401-421.
Zhu, et al. Diverse mechanisms of CRISPR-Cas9 inhibition by type IIC anti-CRISPR proteins. Molecular Cell. Apr. 2019; 74(2):296-309.

* cited by examiner

*Primary Examiner* — Quang Nguyen
(74) *Attorney, Agent, or Firm* — Sheppard Mullin Richter & Hampton LLP

(57) ABSTRACT

Provided are amino acid sequences capable of binding to and inhibiting a Cas protein's ability to bind to a nucleic acid molecule, thereby inhibiting the Cas protein's function in genome editing. Such Cas protein inhibitors, which can be comprised of a major coat protein (G8P), an extracellular region of the G8P (G8P$_{EX}$), or a biological equivalent, are useful in improving the specificity of Cas protein-based genome editing procedures.

13 Claims, 10 Drawing Sheets

Specification includes a Sequence Listing.

| Max. XlinkX Score | Seq. A | Acces. A | Pos. A | Seq. B | Acces. B | Pos. B | Crosslink | #CSMs | Protein. A | Protein. B |
|---|---|---|---|---|---|---|---|---|---|---|
| 138.24 | AEGDDPA[K]AAF | M13-pep | 8 | [K]SVKEL | Cas9 | 1158 | DSSO; Inter | 1 | M13-pep | Cas9 |
| 102.5 | E[K]NPIDFLEAKGY | Cas9 | 1176 | AEGDDPA[K]AAF | M13-pep | 8 | DSSO; Inter | 1 | Cas9 | M13-pep |

FIG. 5

| Organism | Uniprot ID | Bacteria Host | Peptide Sequence |
|---|---|---|---|
| Enterobacteria phage M13 | P69541 | Escherichia coli | AEGDDPAKAAFNSLQASATEY |
| Pseudomonas phage Pf1 | P03631 | Pseudomonas aeruginosa | ATSLPAFAGVIDTSAVESAITDGQGDMKA |
| Enterobacteria phage f1 | P69540 | Escherichia coli | AEGDDPAKAAFDSLQASATEY |
| Pseudomonas phage Pf3 | P03623 | Pseudomonas aeruginosa | MQSVITDVTGQLTAVQAD |
| Enterobacteria phage Ike | P03620 | Escherichia coli | AEPNAATNYATEAMDSLKTQAIDLI |
| Enterobacteria phage If1 | P03619 | Escherichia coli | ADDATSQAKAAFDSLTAQATEM |
| Xanthomonas phage Xf | P03622 | Xanthomonas campestris pv. oryzae | SCVGDGVDVVSAIEGAAGP |
| Thermus phage PH75 | P62889 | Thermus thermophilus | MDFNPSEVASQVTNYIQ |
| Enterobacteria phage I2-2 | P15416 | Escherichia coli | ADGTSTATSYATEAMNSLKTQATDLDQ |
| Xanthomonas phage phiLf | P58674 | Xanthomonas campestris pv. campestris | MGDILTCVSGAE |

FIG. 7

COMPOSITION AND USE OF CAS PROTEIN INHIBITORS

The present invention claims the priority of the PCT/CN2018/102908, filed on Aug. 29, 2018, the contents of which are incorporated herein by its entirety.

BACKGROUND

Genome editing can be used to correct driver mutations underlying genetic diseases and thereby resulting in complete cure of these diseases in a living organism; genome editing can also be applied to engineer the genome of crops, thus increasing the yield of crops and conferring crops resistance to environmental contamination or pathogen infection; likewise, microbial genome transformation through accurate genome editing is of great significance in the development of renewable bio-energy.

CRISPR/Cas (Clustered regularly interspaced short palindromic repeats/CRISPR-associated protein) system has been the most powerful genomic editing tool since its conception for its unparalleled editing efficiency, convenience and the potential applications in living organism. Directed by guide RNA (gRNA), a Cas nuclease can generate DNA double strand breaks (DSBs) at the targeted genomic sites in various cells (both cell lines and cells from living organisms). These DSBs are then repaired by the endogenous DNA repair system, which could be utilized to perform desired genome editing.

Base editors (BE), which integrate the CRISPR/Cas system with the APOBEC (apolipoprotein B mRNA editing enzyme, catalytic polypeptide-like) cytosine deaminase family, were recently developed that greatly enhanced the efficiency of CRISPR/Cas9-mediated gene correction. Through fusion with Cas9 nickase (nCas9) or catalytically dead Cas9 (dCas9), the cytosine (C) deamination activity of rat APOBEC1 (rA1) can be purposely directed to the target bases in genome and to catalyze C to Thymine (T) substitutions at these bases.

Nonspecific and unintended ("off target") genetic modifications can arise through the use of the genome editing methods. For instance, in a CRISPR/Cas system, if the complexes do not bind the target sequence, often a result of homologous sequences and/or mismatch tolerance, they will cleave off-target DSB and cause non-specific genetic modifications. Off-target effects consist of unintended point mutations, deletions, insertions, inversions, and translocations. There is a need to develop methods for reducing such off target genetic modifications.

SUMMARY

The present disclosure provides compositions of peptide inhibitors for Cas proteins and their use in genome editing. One embodiment of the present disclosure provides a method for improving the specificity of a Cas protein-based genome editing procedure, comprising contacting a sample undergoing the Cas protein-based genome editing procedure with a polypeptide or a polynucleotide encoding the polypeptide, wherein the polypeptide comprises a major coat protein (G8P), an extracellular region of the G8P ($G8P_{EX}$), or a biological equivalent of the G8P or the $G8P_{EX}$ capable of binding to the Cas protein.

In some embodiments, the Cas protein is selected from the group consisting of SpCas9, SaCas9, NmeCas9, StCas9, CjCas9, AsCpf1, FnCpf1, SsCpf1, PcCpf1, BpCpf1, CmtCpf1, LiCpf1, PmCpf1, Pb3310Cpf1, Pb4417Cpf1, BsCpf1, EeCpf1, RfCas13d, LwaCas13 a, PspCas13b, PguCas13b, RanCas13b, variants thereof, and chemically modified version thereof which could interact with the peptide inhibitor or the chemically modified version. In some embodiments, the Cas protein and the polypeptide or polynucleotide are provided to the sample simultaneously.

In some embodiments, the polynucleotide further comprises an inducible promoter. In some embodiments, the polypeptide or polynucleotide is provided to the sample after the sample has been in contact with the Cas protein. In some embodiments, the polypeptide is chemically modified.

In some embodiments, the Cas protein-based genome editing procedure is in vitro. In some embodiments, the Cas protein-based genome editing procedure is in a live subject. In some embodiments, the live subject is a human subject, an animal subject, a plant subject, a yeast subject, a bacterial subject, or a viral subject, without limitation.

Also provided, in one embodiment, is a method of genome editing in a subject, comprising: administering to the subject a Cas protein-based genome editing system; and then administering to the subject a polypeptide or a polynucleotide encoding the polypeptide, wherein the polypeptide comprises a major coat protein (G8P), an extracellular region of the G8P ($G8P_{EX}$), or a biological equivalent of the G8P or the $G8P_{EX}$ capable of binding to the Cas protein.

In some embodiments, the polypeptide or polynucleotide is administered after genome editing with the Cas protein-based genome editing system has initiated. In some embodiments, the polypeptide or polynucleotide is administered at least 12 hours after administration of the Cas protein-based genome editing system. In some embodiments, the administration is intravenous injection, muscular injection, nasal spray, or topical application.

Yet another embodiment provides a method of genome editing in a subject, comprising administering to the subject a Cas protein-based genome editing system and a polynucleotide encoding a polypeptide operatively linked to an inducible promoter, wherein the polypeptide comprises a major coat protein (G8P), an extracellular region of the G8P ($G8P_{EX}$), or a biological equivalent of the G8P or the $G8P_{EX}$ capable of binding to the Cas protein.

In some embodiments, the method further comprises inducing the expression of the polypeptide by activating the inducible promoter after the genome editing with the Cas protein-based genome editing system has initiated. In some embodiments, the Cas protein and the polypeptide are encoded on a same nucleic acid construct.

Further provided, in one embodiment, is a recombinant expression vector comprising a first polynucleotide fragment encoding a Cas protein and a second polynucleotide fragment encoding a polypeptide comprising a major coat protein (G8P), an extracellular region of the G8P ($G8P_{EX}$), or a biological equivalent of the G8P or the $G8P_{EX}$ capable of binding to the Cas protein.

In some embodiments, the second polynucleotide fragment is operatively linked to an inducible promoter for expressing the polypeptide in a cell. In some embodiments, the Cas protein is selected from the group consisting of SpCas9, SaCas9, NmeCas9, StCas9, CjCas9, AsCpf1, FnCpf1, SsCpf1, PcCpf1, BpCpf1, CmtCpf1, LiCpf1, PmCpf1, Pb3310Cpf1, Pb4417Cpf1, BsCpf1, EeCpf1, RfCas13d, LwaCas13a, PspCas13b, PguCas13b, RanCas13b and variants thereof.

In some embodiments, the vector further comprises coding sequences for one or more proteins selected from the group consisting of a cytidine deaminase or adenosine deaminase, and a uracil glycosylase inhibitor (UGI).

Yet another embodiment provides a recombinant expression vector comprising a nucleotide fragment encoding a polypeptide and an operatively linked promoter for expressing the amino acid sequence in a eukaryotic cell, wherein the polypeptide comprises a major coat protein (G8P), an extracellular region of the G8P (G8P$_{EX}$), or a biological equivalent of the G8P or the G8P$_{EX}$ capable of binding to a Cas protein.

In some embodiments, the promoter initiates transcription of the nucleotide fragment in a mammalian cell. In some embodiments, the promoter is inducible.

Composition, combination, or kit is also provided comprising a Cas protein and a polypeptide comprising a major coat protein (G8P), an extracellular region of the G8P (G8P$_{EX}$), or a biological equivalent of the G8P or the G8P$_{EX}$ capable of binding to the Cas protein.

The polypeptide of the present disclosure, in some embodiments, may be provided as part of a viral particle, such as an intact M13 bacteriophage, or a nanoparticle.

Still, in another embodiment, the present disclosure provides a molecule comprising a Cas protein, a polypeptide comprising a major coat protein (G8P), an extracellular region of the G8P (G8P$_{EX}$), or a biological equivalent of the G8P or the G8P$_{EX}$ capable of binding to the Cas protein, and a cleavable linker connecting the Cas protein and the polypeptide.

In some embodiments, the cleavable linker is a peptide comprising a protease cleavage site. In some embodiments, the protease cleavage site is a self-cleavage site. In some embodiments, the cleavable linker is a photo- or drug-activatable. In some embodiments, the Cas protein is fused to a cytidine deaminase or an adenosine deaminase.

Also provided is a pharmaceutical composition comprising a pharmaceutically acceptable carrier and a polypeptide comprising a major coat protein (G8P), an extracellular region of the G8P (G8P$_{EX}$), or a biological equivalent of the G8P or the G8P$_{EX}$ capable of binding to a Cas protein. In some embodiments, the composition is provided in the form of an injectable, a tablet, a capsule, a gel, a cream or a spray.

In any of the embodiments, the G8P can be selected from the group consisting of SEQ ID NO:11-20. In any of the embodiments, the G8P$_{EX}$ is selected from the group consisting of SEQ ID NO:1-10. In any of the embodiments, the biological equivalent has at least 70% sequence identity to the G8P or the G8P$_{EX}$. In any embodiment, the biological equivalent is selected from the group consisting of SEQ ID NO:37-436.

Also provided are polypeptides comprising an amino acid sequence derived by including one, two, three, four, or five amino acid addition, deletion, substitutions or the combinations thereof, from a sequence selected from the group consisting of SEQ ID NO:1-22 and 37-436, wherein the polypeptide is capable of binding to a Cas protein. Still also provided are methods of genome editing in a subject, comprising: administering to the subject a Cas protein-based genome editing system; and administering to the subject the polypeptide or a polynucleotide encoding the polypeptide.

BRIEF DESCRIPTION OF THE DRAWINGS

FIG. 5. Mass spectrometry (MS) analyses of the interface between SpCas9 and bacteriophage M13 G8P$_{EX}$. Two cross-linking events are identified between SpCas9 and G8PEX peptides, including the one between KSVKEL (SEQ ID NO:23) and AEGDDPAKAAF (SEQ ID NO:24) and the one between ENKPIDFLEAKGY (SEQ ID NO:25) and AEGDDPAKAAF (SEQ ID NO:24).

DETAILED DESCRIPTION

Definitions

Figure 1:
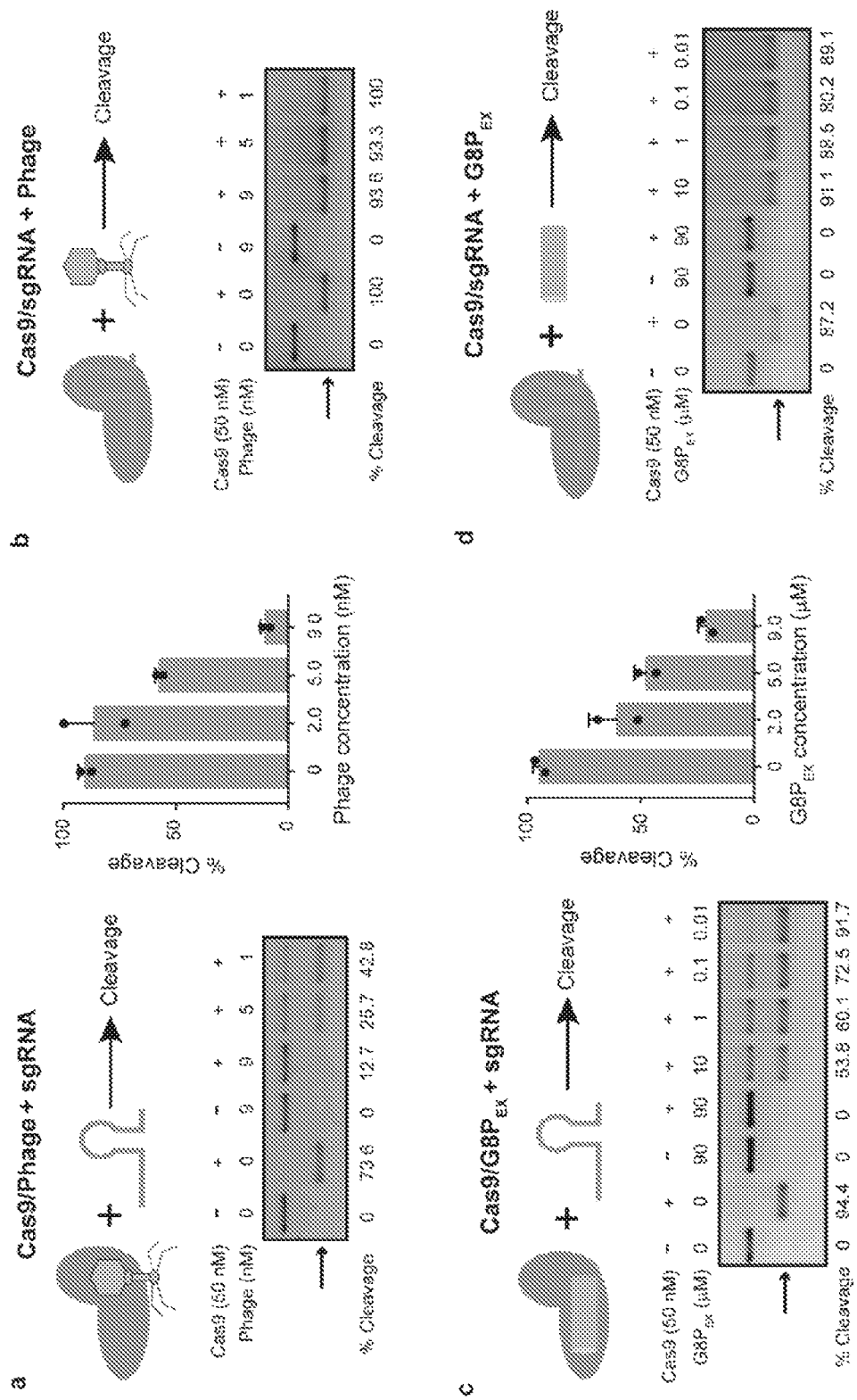
FIG. 1. The major coat protein G8P from bacteriophage M13 inhibits the in vitro activity of SpCas9. a-b, Inhibition of the in vitro activity of SpCas9 by intact M13 bacteriophage prior to (a) or post (b) the assembly of Cas9/sgRNA ribonucleoprotein (Cas9 RNP). c-d, Inhibition of the in vitro activity of SpCas9 by G8P$_{EX}$ prior to (a) or post (b) the assembly of Cas9 RNP. Arrows indicate cleavage products. The results of two biological replicates are shown as mean±SD. Cartoons are not drawn to scale.

It is to be noted that the term "a" or "an" entity refers to one or more of that entity; for example, "a peptide," is understood to represent one or more peptides. As such, the terms "a" (or "an"), "one or more," and "at least one" can be used interchangeably herein.

Major Coat Protein and Fragments, and Methods of Use

It is discovered herein, unexpectedly, that major coat proteins (i.e., G8P) from phage viruses can bind to and prevent Cas proteins from binding to a guide nucleotide. The binding, as demonstrated in the experimental examples, can occur between the extracellular region of the G8P (also referred to as "G8P$_{EX}$"), in particular the N-terminal portion of the α-helical structure, and a site on the Cas protein distal from its RNA- or DNA-binding pocket. Accordingly, this binding allosterically inhibits the function of the Cas protein.

The initial discovery was made with the G8P from Inoviridae inovirus bacteriophage (M13) (including the bacteriophage itself), but further experiments showed that other G8P$_{EX}$, e.g., those prepared from bacteriophages Pf1, f1, I2-2 and L. monocytogenes bacteriophage M7 also efficiently prohibited the binding between Cas and RNA. Moreover, these peptides not only inhibited the function of the Cas9 protein, they also bound to and had inhibitory effects on another Cas protein, Cas12a (Cpf1). These results indicate that the major coat proteins are widely existing Cas inhibitors in bacteriophages.

The G8P proteins and fragments can provide a ready solution to the off-target editing problem in genome editing. After a Cas protein-based genome editing complex has successfully edited a target genomic site, the G8P proteins and fragments can prevent unintended damage to other portions of a genome.

In accordance with one embodiment of the present disclosure, therefore, provided is a method of improving the specificity of a Cas protein-based genome editing procedure in a cell. The method entails contacting the cell with a major coat proteins (G8P), an extracellular portion thereof, or a biological derivative each thereof. The contacting can be in vitro or in vivo (e.g., in a mammalian subject).

Examples of G8P proteins and their extracellular portions (G8P$_{EX}$) are provided in Table 1 below, which have been tested for their ability to bind and inhibit Cas proteins.

TABLE 1

Example G8P and G8P$_{EX}$

| UniProtKB (Name/Organism) | Sequence (G8P$_{EX}$ residues are bold and underlined) | SEQ ID NO: |
|---|---|---|
| P69541 (Capsid protein G8P/ Enterobacteria phage M13) | MKKSLVLKASVAVATLVPMLSFA<u>AEGDDPAKAAFNSLQASATEY</u>IGYAWA MVVVIVGATIGIKLFKKFTSKAS | 11 |
| G8P$_{EX}$ | AEGDDPAKAAFNSLQASATEY | 1 |
| P03621 (Capsid protein G8P/ Pseudomonas phage Pf1)) | MKAMKQRIAKFSPVASFRNLCIAGSVTA<u>ATSLPAFAGVIDTSAVESAITD GQGDMKA</u>IGGYIVGALVILAVAGLIYSMLRKA | 12 |
| G8P$_{EX}$ | ATSLPAFAGVIDTSAVESAITDGQGDMKA | 2 |
| P69540 (Capsid protein G8P/ Enterobacteria phage f1) | MKKSLVLKASVAVATLVPMLSFA<u>AEGDDPAKAAFDSLQASATEY</u>IGYAWA MVVVIVGATIGIKLFKKFTSKAS | 13 |
| G8P$_{EX}$ | AEGDDPAKAAFDSLQASATEY | 3 |
| P03623 (Capsid protein G8P/ Pseudomonas phage Pf3) | <u>MQSVITDVTGQLTAVQAD</u>ITTIGGAIIVLAAVVLGIRWIKAQFF | 14 |
| G8P$_{EX}$ | MQSVITDVTGQLTAVQAD | 4 |
| P03620 (Capsid protein G8P/ Enterobacteria phage IKe) | MRVLSTVLAAKNKIALGAATMLVSAGSFA<u>AEPNAATNYATEAMDSLKTQA IDLI</u>SQTWPVVTTVVVAGLVIRLFKKFSSKAV | 15 |
| G8P$_{EX}$ | AEPNAATNYATEAMDSLKTQAIDLI | 5 |

TABLE 1-continued

Example G8P and G8P$_{EX}$

| UniProtKB (Name/Organism) | Sequence (G8P$_{EX}$ residues are bold and underlined) | SEQ ID NO: |
|---|---|---|
| P03619 (Capsid protein G8P/ Enterobacteria phage If1) | MKKSVVAKIIAGSTLVIGSSAFAADDATSQAKAAFDSLTAQATEMSGYAW ALVVLVVGATVGIKLFKKFVSRAS | 16 |
| G8P$_{EX}$ | ADDATSQAKAAFDSLTAQATEM | 6 |
| P03622 (Capsid protein G8P/ Xanthomonas phage Xf) | SGVGDGVDVVSAIEGAAGPIAAIGGAVLTVMVGIKVYKWVRRAM | 17 |
| G8P$_{EX}$ | SGVGDGVDVVSAIEGAAGP | 7 |
| P82889 (Capsid protein G8P/ Thermus phage PH75) | MDFNPSEVASQVTNYIQAIAAAGVGVLALAIGLSAAWKYAKRFLKG | 18 |
| G8P$_{EX}$ | MDFNPSEVASQVTNYIQ | 8 |
| P15416 (Capsid protein G8P/ Enterobacteria phage I2-2) | MSVITKVAAAKNKIVVGAGLLMASAGAFAADDGTSTATSYATEAMNSLKT QATDLIDQTWPVVTSVAVAGLAIRLFKKFSSKAV | 19 |
| G8P$_{EX}$ | ADDGTSTATSYATEAMNSLKTQATDLIDQ | 9 |
| P68674 (Capsid protein G8P/ Xanthomonas phage phi-Lf) | MGDILTGVSGAEAATAMIAAAAIIALVGFTKWGAKKVASFFG | 20 |
| G8P$_{EX}$ | MGDILTGVSGAE | 10 |
| L. monocytogenes (strain M7) bacteriophage M7 | MANEITKLLDVVTPEVFNAYMDNFTSEKSAIIQSGIAVADPSVAQNITAG GLLVNMPFWNDLDGEDETLGDGEKGLETGKITASADIAAVMYRGRGWSVN ELAAVISGDDPLDALMGKIASWWMRREQTVLISVLNGLFAKNGALASSHL LSKPTSAISGNLVLDAKQLLGDSSDRLSLMVMHSAVYTALQKQNLIAFIP NARGEVNIPTYLGYRVVVDDGVPSTGTGAAKVYTSYLFATGSIGRNIGNP AKLTTFETARDASKGNDQVFTRRAFTMHPYGVKFKNAVRDANEITPTNAD LAKAGNWEKVYEDKQIGIVGIQHLVEELPASGA | 22 |
| G8P$_{EX}$ | SKGNDQVFTRRAFTMHPYGVKFKNAVRDANEITPTNADL | 21 |

Homologues (biological equivalents) of G8P$_{EX}$ have also been identified (e.g., SEQ ID NO:37-436) via informatic approaches, as shown in Example 2 and are contemplated to exhibit similar binding and inhibitory activities.

As shown in Example 1, certain amino acid residues in the G8P$_{EX}$ are important for the binding where the others are less or not important. These important amino acid residents, for instant, can be located at the N-terminal portion of the α-helical structure. Accordingly, if one, two or more amino acid residues in other portions of the G8P$_{EX}$ are modified (substituted, deleted or added), it is expected that such variants still retain the binding and inhibitory activities. Such biological equivalents of the G8P and G8P$_{EX}$, accordingly, are also within the scope of the present disclosure.

The term "biological equivalent" of a reference amino acid sequence refers to an amino acid sequence having a certain degree of sequence identity, while retaining a desired structure, function, or activity of the reference amino acid sequence. In some aspects, the sequence identity is at least about 70%, 75%, 80%, 85%, 90%, 95%, 98%, or 99%. In some aspects, the biological equivalent has one, two, three, four or five addition, deletion, substitution and their combinations thereof of amino acids as compared to the reference polypeptide. A desired structure for the biological equivalent of the G8P or G8P$_{EX}$ is the α-helical structure. A desired activity of the biological equivalent of the G8P or G8P$_{EX}$ is the ability to bind to a Cas protein and/or inhibit the Cas protein's binding to a nucleic acid molecule, such as sgRNA.

In some embodiments, the amino acid substitutions, additions and/or deletions are not within the N-terminal portion (e.g., N-terminal 5, 6, 7, 8, 9, 10, 11, 12, 13, 14, 15, 16, 17, 18, 19 or 20 amino acid residues) of the α-helical structure of the G8P or G8P$_{EX}$ sequence. In some embodiments, the amino acid substitutions, additions and/or deletions are not within the N-terminal portion (e.g., N-terminal 5, 6, 7, 8, 9, 10, 11, 12, 13, 14, 15, 16, 17, 18, 19 or 20 amino acid residues) of the α-helical structure of the G8P or G8P$_{EX}$ sequence. In some embodiments, at least some, or all, of the amino acid substitutions, additions and/or deletions are not within the α-helical structure of the G8P or G8P$_{EX}$ sequence. In some embodiments, the biological equivalent of the G8P or G8P$_{EX}$ retains the α-helical structure.

In some embodiments, one or more of the amino acid substitutions are conservative amino acid substitutions. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in an immunoglobulin polypeptide is preferably replaced with another amino acid residue from the same side chain family. In another embodiment, a string of amino acids can be replaced with a structurally similar string that differs in order and/or composition of side chain family members.

Non-limiting examples of conservative amino acid substitutions are provided in the table below, where a similarity score of 0 or higher indicates conservative substitution between the two amino acids.

TABLE A

Amino Acid Similarity Matrix

| | C | G | P | S | A | T | D | E | N | Q | H | K | R | V | M | I | L | F | Y | W |
|---|---|---|---|---|---|---|---|---|---|---|---|---|---|---|---|---|---|---|---|---|
| W | −8 | −7 | −6 | −2 | −6 | −5 | −7 | −7 | −4 | −5 | −3 | −3 | 2 | −6 | −4 | −5 | −2 | 0 | 0 | 17 |
| Y | 0 | −5 | −5 | −3 | −3 | −3 | −4 | −4 | −2 | −4 | 0 | −4 | −5 | −2 | −2 | −1 | −1 | 7 | 10 | |
| F | −4 | −5 | −5 | −3 | −4 | −3 | −6 | −5 | −4 | −5 | −2 | −5 | −4 | −1 | 0 | 1 | 2 | 9 | | |
| L | −6 | −4 | −3 | −3 | −2 | −2 | −4 | −3 | −3 | −2 | −2 | −3 | −3 | 2 | 4 | 2 | 6 | | | |
| I | −2 | −3 | −2 | −1 | −1 | 0 | −2 | −2 | −2 | −2 | −2 | −2 | −2 | 4 | 2 | 5 | | | | |
| M | −5 | −3 | −2 | −2 | −1 | −1 | −3 | −2 | 0 | −1 | −2 | 0 | 0 | 2 | 6 | | | | | |
| V | −2 | −1 | −1 | −1 | 0 | 0 | −2 | −2 | −2 | −2 | −2 | −2 | −2 | 4 | | | | | | |
| R | −4 | −3 | 0 | 0 | −2 | −1 | −1 | −1 | 0 | 1 | 2 | 3 | 6 | | | | | | | |
| K | −5 | −2 | −1 | 0 | −1 | 0 | 0 | 0 | 1 | 1 | 0 | 5 | | | | | | | | |
| H | −3 | −2 | 0 | −1 | −1 | −1 | 1 | 1 | 2 | 3 | 6 | | | | | | | | | |
| Q | −5 | −1 | 0 | −1 | 0 | −1 | 2 | 2 | 1 | 4 | | | | | | | | | | |
| N | −4 | 0 | −1 | 1 | 0 | 0 | 2 | 1 | 2 | | | | | | | | | | | |
| E | −5 | 0 | −1 | 0 | 0 | 0 | 3 | 4 | | | | | | | | | | | | |
| D | −5 | 1 | −1 | 0 | 0 | 0 | 4 | | | | | | | | | | | | | |
| T | −2 | 0 | 0 | 1 | 1 | 3 | | | | | | | | | | | | | | |
| A | −2 | 1 | 1 | 1 | 2 | | | | | | | | | | | | | | | |
| S | 0 | 1 | 1 | 1 | | | | | | | | | | | | | | | | |
| P | −3 | −1 | 6 | | | | | | | | | | | | | | | | | |
| G | −3 | 5 | | | | | | | | | | | | | | | | | | |
| C | 12 | | | | | | | | | | | | | | | | | | | |

TABLE B

Conservative Amino Acid Substitutions

| For Amino Acid | Substitution With |
|---|---|
| Alanine | D-Ala, Gly, Aib, β-Ala, L-Cys, D-Cys |
| Arginine | D-Arg, Lys, D-Lys, Orn D-Orn |
| Asparagine | D-Asn, Asp, D-Asp, Glu, D-Glu Gln, D-Gln |
| Aspartic Acid | D-Asp, D-Asn, Asn, Glu, D-Glu, Gln, D-Gln |
| Cysteine | D-Cys, S-Me-Cys, Met, D-Met, Thr, D-Thr, L-Ser, D-Ser |
| Glutamine | D-Gln, Asn, D-Asn, Glu, D-Glu, Asp, D-Asp |
| Glutamic Acid | D-Glu, D-Asp, Asp, Asn, D-Asn, Gln, D-Gln |
| Glycine | Ala, D-Ala, Pro, D-Pro, Aib, β-Ala |
| Isoleucine | D-Ile, Val, D-Val, Leu, D-Leu, Met, D-Met |
| Leucine | Val, D-Val, Met, D-Met, D-Ile, D-Leu, Ile |
| Lysine | D-Lys, Arg, D-Arg, Orn, D-Orn |
| Methionine | D-Met, S-Me-Cys, Ile, D-Ile, Leu, D-Leu, Val, D-Val |
| Phenylalanine | D-Phe, Tyr, D-Tyr, His, D-His, Trp, D-Trp |
| Proline | D-Pro |
| Serine | D-Ser, Thr, D-Thr, allo-Thr, L-Cys, D-Cys |
| Threonine | D-Thr, Ser, D-Ser, allo-Thr, Met, D-Met, Val, D-Val |
| Tyrosine | D-Tyr, Phe, D-Phe, His, D-His, Trp, D-Trp |
| Valine | D-Val, Leu, D-Leu, Ile, D-Ile, Met, D-Met |

In some embodiments, the biological equivalent of the G8P or G8P$_{EX}$ retains the ability to bind to a Cas protein and/or inhibit the Cas protein's binding to a nucleic acid molecule, such as sgRNA.

The polypeptides of the present disclosure, which includes a G8P or G8P$_{EX}$ or a biological equivalent, may be delivered as part of a fusion, as a standalone protein, or a part of a viral particle such as a bacteriophage. As shown in the experimental examples, the intact M13 bacteriophage, the isolated G8P protein, and the G8P$_{EX}$ fragments all exhibited inhibitory effects. In some embodiments, therefore, the polypeptide is provided in a viral particle that includes a virus that contains the G8P protein or a biological equivalent.

The term "Cas protein" or "clustered regularly interspaced short palindromic repeats (CRISPR)-associated (Cas) protein" refers to RNA-guided DNA endonuclease enzymes associated with the CRISPR (Clustered Regularly Interspaced Short Palindromic Repeats) adaptive immunity system in *Streptococcus pyogenes*, as well as other bacteria. Non-limiting examples of Cas proteins include *Streptococcus pyogenes* Cas9 (SpCas9), *Staphylococcus aureus* Cas9 (SaCas9), *Acidaminococcus* sp. Cas12a (AsCpf1), *Lachnospiraceae bacterium* Cas12a (LbCpf1), *Francisella novicida* Cas12a (FnCpf1). Additional examples are provided in Komor et al., "CRISPR-Based Technologies for the Manipulation of Eukaryotic Genomes," Cell. 2017 Jan. 12;168(1-2):20-36.

Non-limiting examples include SpCas9, FnCas9, St1Cas9, St3Cas9, NmCas9, SaCas9, AsCpf1, LbCpf1, FnCpf1, VQR SpCas9, EQR SpCas9, VRER SpCas9, RHA FnCas9, and KKH SaCas9. In some embodiments, the Cas protein is a mutant of protein selected from the group consisting of SpCas9, FnCas9, St1Cas9, St3Cas9, NmCas9, SaCas9, AsCpf1, LbCpf1, FnCpf1, VQR SpCas9, EQR SpCas9, VRER SpCas9, RHA FnCas9, and KKH SaCas9, wherein the mutant retains the DNA-binding capability but does not introduce double strand DNA breaks. Cas proteins also encompass chemically modified versions that can interact with the Cas protein inhibitor or the chemically modified version thereof.

For example, it is known that in SpCas9, residues Asp10 and His840 are important for Cas9's catalytic (nuclease) activity. When both residues are mutated to Ala, the mutant loses the nuclease activity. In another embodiment, only the Asp10Ala mutation is made, and such a mutant protein cannot generate a double strand break; rather, a nick is generated on one of the strands. Such a mutant is also referred to as a Cas9 nickase.

Such and more examples are provided in Table C below.

TABLE C

Example Cas Proteins

| Cas protein types | Cas proteins |
| --- | --- |
| Cas9 proteins | Cas9 from *Staphylococcus aureus* (SaCas9) |
| | Cas9 from *Neisseria meningitidis* (NmeCas9) |
| | Cas9 from *Streptococcus thermophilus* (StCas9) |
| | Cas9 from *Campylobacter jejuni* (CjCas9) |
| Cas12a (Cpf1) proteins | Cas12a (Cpf1) from *Acidaminococcus* sp BV3L6 (AsCpf1) |
| | Cas12a (Cpf1) from *Francisella novicida* sp BV3L6 (FnCpf1) |
| | Cas12a (Cpf1) from *Smithella* sp SC K08D17 (SsCpf1) |
| | Cas12a (Cpf1) from *Porphyromonas crevioricanis* (PcCpf1) |
| | Cas12a (Cpf1) from *Butyrivibrio proteoclasticus* (BpCpf1) |
| | Cas12a (Cpf1) from *Candidatus Methanoplasma termitum* (CmtCpf1) |
| | Cas12a (Cpf1) from *Leptospira inadai* (LiCpf1) |
| | Cas12a (Cpf1) from *Porphyromonas macacae* (PmCpf1) |
| | Cas12a (Cpf1) from *Peregrinibacteria bacterium* GW2011 WA2 33 10 (Pb3310Cpf1) |
| | Cas12a (Cpf1) from *Parcubacteria bacterium* GW2011 GWC2 44 17 (Pb4417Cpf1) |
| | Cas12a (Cpf1) from *Butyrivibrio* sp. NC3005 (BsCpf1) |
| | Cas12a (Cpf1) from *Eubacterium eligens* (EeCpf1) |
| Cas13 proteins | Cas13d from *Ruminococcus flavefaciens* XPD3002 (RfCas13d) |
| | Cas13a from *Leptotrichia wadei* (LwaCas13a) |
| | Cas13b from *Prevotella* sp. P5-125 (PspCas13b) |
| | Cas13b from *Porphyromonas gulae* (PguCas13b) |
| | Cas13b from *Riemerella anatipestifer* (RanCas13b) |
| Engineered Cas proteins | Nickases (mutation in one nuclease domain) |
| | Catalytically inactive mutant (dCas9; mutations in both of the nuclease domains) |
| | Enhanced variants with improved specificity (see, e.g., Chen et al., Nature, 550, 407-410 (2017)) |

A "Cas protein-based genome editing procedure" as used herein refers to a method, which can be in vitro or in vivo, in prokaryotic or eukaryotic cells, tissue, organs or bodies, that employs a Cas protein, preferably with other proteins and nucleic acids, to achieve the goal of making a genetic change in a genome. Examples of such procedures include, without limitation, CRISPR-Cas gene editing, and base editing using catalytically dead Cas (dCas) proteins, and cytidine deaminase and adenosine deaminase enzymes.

A "Cas protein-based genome editing system" as used herein refers to a composition or combination of biological molecules needed to carry out a Cas protein-based genome editing procedure. Such biological molecules include a Cas protein as described herein, and optionally a guide nucleic acid, a cytidine deaminase, and/or a uracil glycosylase inhibitor (UGI).

In one embodiment, a "Cas protein inhibitor" of the present disclosure (e.g., G8P, $G8P_{EX}$ or a biological equivalent thereof) is provided to a cell undergoing a Cas protein-based genome editing procedure, such as genome editing or base editing. In an in vitro system, the Cas protein inhibitor can be added to a solution including the cell. For a procedure conducted on an individual such as a patient, the Cas protein inhibitor can be administered using routes known in the art.

As observed in the examples, the G8P, $G8P_{EX}$ or a biological equivalent thereof binds to the Cas protein at a site that is distant from the nucleic acid-binding site of the Cas protein. Such binding, therefore, allosterically inhibits the Cas protein's binding to the nuclei acid molecules (e.g., sgRNA). Accordingly, addition of the G8P, $G8P_{EX}$ or a biological equivalent thereof after a Cas protein is already bound to the nucleic acid would not affect the existing binding. In other words, addition of a G8P, $G8P_{EX}$ or a biological equivalent thereof would only prevent or inhibit new Cas protein-nucleic acid bindings. Such a property of these peptides can have advantages.

For instance, when a Cas protein-based genome editing system is introduced to a cell, the initial genome editing is more likely to be the correct one (desired). After the initial phase of editing, off target (undesired) editing may more likely occur. To reduce undesired genomic changes caused by Cas protein-based systems, therefore, a G8P, $G8P_{EX}$ or a biological equivalent thereof can be added (or induced to express) after the desired editing is initiated. As such, the addition of the G8P, $G8P_{EX}$ or a biological equivalent thereof would not impact the desired editing, and only prevent/inhibit the undesired editing.

In some embodiments, therefore, a genome editing method is provided, in which a Cas protein-based genome editing system and a Cas protein inhibitor (e.g., a G8P, $G8P_{EX}$ or a biological equivalent thereof) are provided to a sample (or administered to a subject). In some embodiments, the Cas protein and the Cas protein inhibitor are provided at the same time, such as in a combined composition of encoded in the same vector. In such a setup, the Cas protein inhibitor can be operatively linked to an inducible promoter, which can be used to induce expression after the initial genome editing phase by the Cas protein has initiated.

Inducible promoters are known in the art. Chemical agents, temperature, and light are all examples of factors that can lead to the induction of a promoter. Common examples of chemical agents are alcohol, tetracycline, steroids, isopropyl β-D-1-thiogalactopyranoside (IPTG), arabinose, metals, and pathogen related (e.g., pathogen infection. Salicylic acid, ethylene and benzothiadiazole (BTH)).

In some embodiments, the Cas protein inhibitor is provided/administered after the Cas protein. The time of such provision/administration can be determined for the particular case. For instance, for mammalian use, after the Cas protein-based genome editing system is administered, it may take up to 2, 4, 6, 8, 12, 18, 24 hours or 1, 2, 3 or 4 days for the system to initiate proper genome editing. Accordingly, the Cas protein inhibitor can be administered to the mammalian subject after that time period. This time period can further be tuned depending on whether the Cas protein inhibitor is administered as a protein or as a polynucleotide which requires transcription and translation.

Without limitation and as further described in detail below, the Cas protein inhibitor of the present disclosure can be provided in the form of a gel, cream, solution, or nebulized particle. Delivery to a subject can be by means of intravenous injection, muscular injection, or topical application without limitation.

Composite Molecules

There are scenarios in which when a Cas protein-based genome editing system should only be functional at certain designated time or location. For instance, when the system is administer to a subject (human, animal, plant etc), it may be desired that the system is only functional in a target tissue (e.g., liver, skin). In other words, the functioning of the system in other tissues is not desired. A ready solution is provided in the present disclosure utilizing the new discovered Cas protein inhibitors.

A composite molecule is provided, in one embodiment, that includes a Cas protein, a polypeptide comprising a major coat protein (G8P), an extracellular region of the G8P (G8P$_{EX}$), or a biological equivalent of the G8P or the G8P$_{EX}$ capable of binding to the Cas protein (collectively Cas protein inhibitors), and a cleavable linker connecting the Cas protein and the polypeptide.

The cleavable linker can be selected or designed such that it is cleaved only in a target tissue or at a target time. For instance, the cleavable linker may be photo-activatable, such that the linker is only cleaved when the composite molecule is delivered to the skin where the light on the skin activates the cleavage of the linker. In tissues wherein light is not available, the composite molecule may be dormant, given that the Cas protein inhibitor binds the Cas protein in the composite molecule, preventing it from binding to a guide nucleic acid. Once the Cas protein inhibitor is cleaved (e.g., in skin cells), the Cas protein has the opportunity to bind to the guide nucleic acid and starts to exert it genome editing functions (the cleaved Cas protein inhibitor may not have sufficient concentration to inhibit the Cas protein).

The cleavable linker may be a peptide comprising a protease cleavage site. When the cleavable linker is a peptide, the composite molecule can be a fusion protein. In some embodiments, the protease cleavage site comprises a self-cleaving peptide, such as the 2A peptides. "2A peptides" are 18-22 amino-acid-long viral oligopeptides that mediate "cleavage" of polypeptides during translation in eukaryotic cells. The designation "2A" refers to a specific region of the viral genome and different viral 2As have generally been named after the virus they were derived from. The first discovered 2A was F2A (foot-and-mouth disease virus), after which E2A (equine rhinitis A virus), P2A (porcine teschovirus-1 2A), and T2A (thosea asigna virus 2A) were also identified.

The cleavable linker can be photo-activatable, as described above, or drug-activatable, or pH-dependent, without limitation. In some embodiments, the Cas protein is fused to a cytidine deaminase or an adenosine deaminase.

Variants, Fusions, Vectors, and Combinations

SEQ ID NO:1-20 are wild-type sequences tested to have Cas protein binding and inhibitory activities. It is contemplated that their variants and homologues also have such activities. For instance, SEQ ID NO:37-436 were identified with bioinformatic searches. Biological equivalents of each of these sequences, it is noted, are also within the scope of the present disclosure.

In any of the embodiments, a Cas protein of the present disclosure may be further fused to a second protein. The second protein can be selected from a FokI nuclease domain, a transcription activator-like effector (TALE), a zinc finger protein, a transposase, a Krüppel associated box (KRAB) transcription suppressor or a transcription activator.

Polynucleotide sequences and vectors are also provided, in some embodiments, which encode one or more of the amino acid sequences described herein. In addition to a coding sequence for the Cas protein inhibitor, the vector can further include a coding sequence for a Cas protein. In addition or alternatively, the Cas protein or a coding sequence can be provided separately in the same composition, formulation, kit or package to facilitate simultaneous delivery. In some embodiments, the Cas protein is fused to a cytidine deaminase, such as A3B (APOBEC3B), A3C (APOBEC3C), A3D (APOBEC3D), A3F (APOBEC3F), A3G (APOBEC3G), A3H (APOBEC3H), A1 (APOBEC1), A3 (APOBEC3), and AID (AICDA). In some embodiments, the Cas protein is fused to an adenosine deaminase, such as adenosine deaminase 1 (Ada1) and adenosine deaminase 2 (Ada2) (see, e.g., Gaudelli et al., *Nature*, 551, 464-71 (2017)).

In some embodiments, the Cas protein is further fused to one, two, three or more uracil glycosylase inhibitor (UGI).

Compositions and Administrations

Methods of administration include but are not limited to intradermal, intramuscular, intraperitoneal, intravenous, subcutaneous, intranasal, epidural, and oral routes. The Cas protein inhibitor or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Thus, pharmaceutical compositions containing the polypeptides of the disclosure may be administered orally, rectally, parenterally, intracisternally, intravaginally, intraperitoneally, topically (as by powders, ointments, drops or transdermal patch), bucally, or as an oral or nasal spray.

The term "parenteral" as used herein refers to modes of administration which include intravenous, intramuscular, intraperitoneal, intrasternal, subcutaneous and intra-articular injection and infusion.

Administration can be systemic or local. In addition, it may be desirable to introduce the Cas protein inhibitor of the disclosure into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

It may be desirable to administer the Cas protein inhibitor or compositions of the disclosure locally to the area in need of treatment; this may be achieved by, for example, and not by way of limitation, local infusion during surgery, topical application, e.g., in conjunction, with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein of the disclosure, care must be taken to use materials to which the protein does not absorb.

The amount of the Cas protein inhibitor of the disclosure which will be effective in the treatment. In addition, in vitro assays may optionally be employed to help identify optimal dosage ranges. The precise dose to be employed in the formulation will also depend on the route of administration, and the seriousness of the disease, disorder or condition, and should be decided according to the judgment of the practitioner and each patient's circumstances. Effective doses may be extrapolated from dose-response curves derived from in vitro or animal model test systems.

The Cas protein inhibitor of the disclosure can be provided in the form of a microparticle or a nanoparticle. Accordingly, preparation of microparticles or nanoparticles are also provided. Microparticles or nanoparticles can be prepared by forming an oil in water emulsion followed by solvent evaporation. The oil phase may be selected from those water immiscible solvents having low boiling point such as esters (e.g. ethyl acetate, butyl acetate), halogenated hydrocarbons (e.g. dichloromethane, chloroform, carbon tetrachloride, chloroethane, dichloroethane, trichloroethane), ethers (e.g. ethyl ether, isopropyl ether), aromatic hydrocarbons (e.g. benzene, toluene, xylene), carbonates (e.g. diethyl carbonate), or the like or mixtures thereof. The oil phase also may comprise a mixture of water miscible solvent (e.g. acetone) and water immiscible solvent (e.g. dichloromethane) in various proportions. Suitable emulsifiers may be used in the preparation of the microparticles or nanoparticles to enhance the stabilization of oil droplets against coalescence, wherein the emulsifier is selected from but not limited to a group comprising polyoxyethylene sorbitan fatty acid esters e.g. mono- and tri-lauryl, palmityl, stearyl and oleyl esters; sorbitan fatty acid esters (SPAN®); polysorbates (Tween®), polyvinyl alcohol, polyvinyl pyrrolidone, gelatin, lecithin, polyoxyethylene castor oil derivatives (Cremophor®), particularly suitable are polyoxyl 35 castor oil (Cremophor®EL) and polyoxyl 40 hydrogenated castor oil (Cremophor® RH40); tocopherol; tocopheryl polyethylene glycol succinate (vitamin E TPGS); tocopherol palmitate and tocopherol acetate; polyoxyethylene-polyoxypropylene co-polymers (Pluronic® or Poloxamer®), sodium CMC and the like or mixtures thereof. Suitable channel forming agents optionally used to formulate the microparticles or nanoparticles is selected from but not limited to a group comprising polyglycols, ethyl vinyl alcohols, glycerin, pentaerythritol, polyvinyl alcohols, polyvinyl pyrrolidone, vinyl pyrrolidone, N-methyl pyrrolidone, polysaccharides such as dextrins and/or hydrolyzed starch, saccharides, sugar alcohols and the like or mixtures thereof.

The present disclosure also provides pharmaceutical compositions. Such compositions comprise an effective amount of a protein and/or nucleotide, and an acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. Further, a "pharmaceutically acceptable carrier" will generally be a non-toxic solid, semisolid or liquid filler, diluent, encapsulating material or formulation auxiliary of any type.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose are also envisioned. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences by E. W. Martin, incorporated herein by reference. Such compositions will contain a therapeutically effective amount of the antigen-binding polypeptide, preferably in purified form, together with a suitable amount of carrier so as to provide the form for proper administration to the patient. The formulation should suit the mode of administration. The parental preparation can be enclosed in ampoules, disposable syringes or multiple dose vials made of glass or plastic.

In an embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

EXAMPLES

Example 1

Inhibition of CRISPR/Cas9 by Bacteriophage Major Coat Protein-Derived Peptides

This example describes the discovery that the major coat protein G8P from Inoviridae inovirus bacteriophage (M13), or even the intact M13 bacteriophage, can inhibit the activity of *Streptococcus pyogenes* Cas9 nuclease (SpCas9). Mutational analyses and high-resolution mass spectrometry determined the candidate interface between G8P peptide and Cas9 protein. It was found that G8P bound to SpCas9 on a site distal from the sgRNA- or DNA-binding pocket. Moreover, in vitro DNA cleavage and Cas9/sgRNA gel mobility shift studies suggested that G8P inhibited the activity of Cas9 by preventing the formation of Cas9/sgRNA ribonucleoprotein (RNP) complex. These results indicate that G8P is mechanistically distinct from previously identified anti-CRISPR proteins (Acrs). G8P allosterically inhibits the function of SpCas9. This example also shows that G8P orthologs from other Inoviridae bacteriophages and *Listeria monocytogenes* serotype 4a (strain M7) bacteriophage can inhibit the activity of CRISPR/Cas9, suggesting that the major coat proteins is a general mechanism used by bacteriophages to invade bacterial immunity. This example further demonstrates that G8P peptide could inhibit the genome editing activity of SpCas9 in human cells.

Phylogenetic analyses suggest a widespread presence of Acrs in bacteriophage. However only a small fraction of Acrs have been experimentally validated to date. Here, it is discovered that the widely used laboratory bacteriophage strain M13 can inhibit the in vitro activity of SpCas9. Treatment of SpCas9 with intact M13 phage particles prior to the assembly with sgRNA prevented the cleavage of substrate DNA. The inhibition was dependent on the concentration of M13 bacteriophage (FIG. 1a). Interestingly, treatment of pre-formed Cas9/sgRNA RNP complex with bacteriophage M13 did not inhibit the cleavage reaction (FIG. 1b).

These observations prompted the examination of the surface proteins of bacteriophage M13. This example found that the extracellular region (SEQ ID NO:1) of the major coat protein G8P (SEQ ID NO:11) (G8P$_{EX}$, SEQ ID NO:1) could inhibit the activity of SpCas9 in a manner similar to the intact phage. Addition of G8P$_{EX}$ to Cas9 prior to the formation of RNP efficiently inhibited DNA cleavage with an approximate half maximum inhibitory concentration (IC$_{50}$) of 5 µM (FIG. 1c) whereas the activity of pre-assembled Cas9 RNP was not affected by G8P$_{EX}$ (FIG. 1d). Importantly, the results that the presence of intact phage or G8P$_{EX}$ did not compromise the activity of pre-formed Cas9 RNP on DNA cleavage suggested that phage or G8P$_{EX}$ did not function as direct competitors to sgRNA or DNA.

Figure 2:
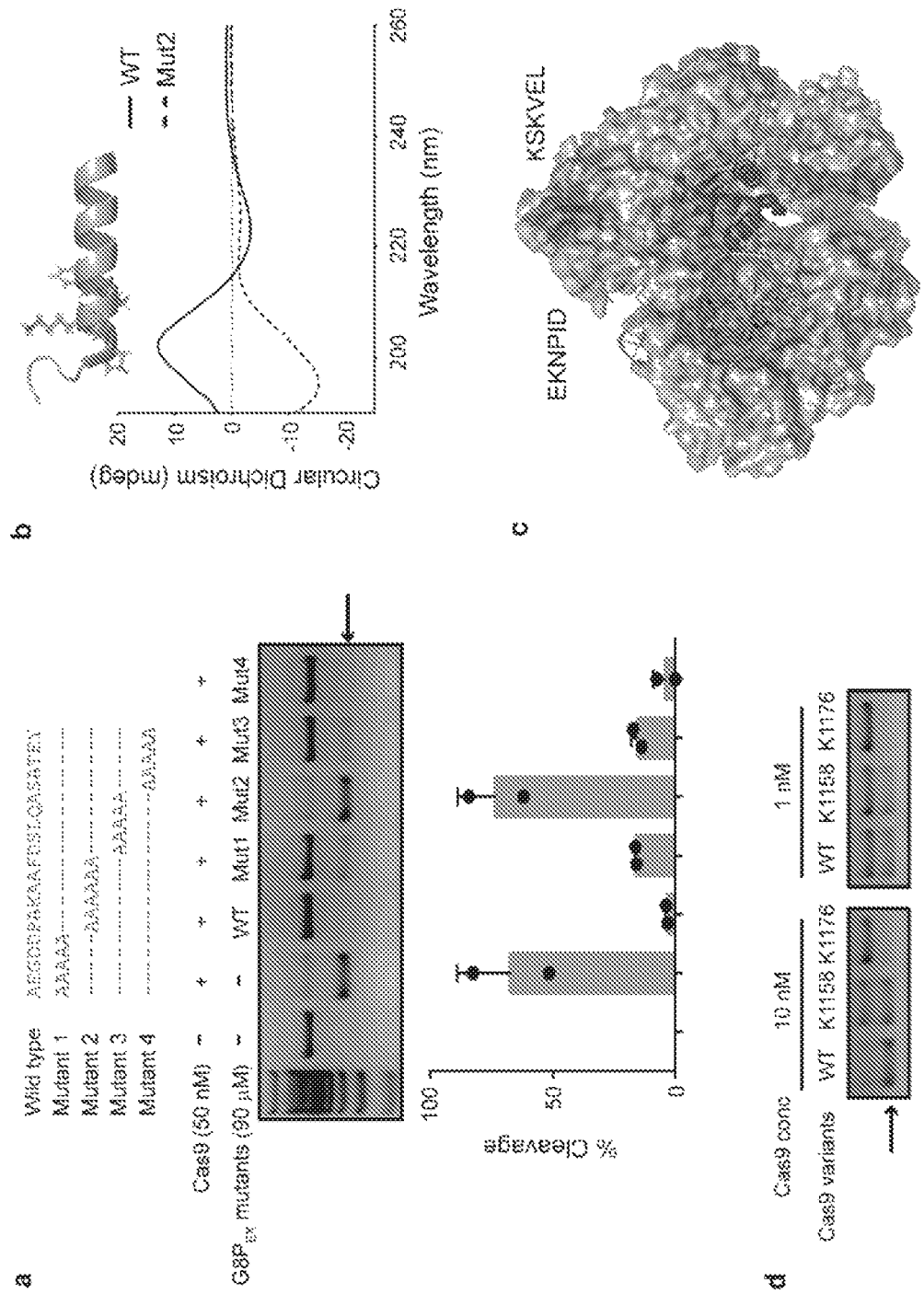
FIG. 2. Determination of the interaction sites between G8P$_{EX}$ and SpCas9. a, Alanine mutations at position 6-11 abolish the inhibitory activity of G8P$_{EX}$ on SpCas9, as determined by in vitro cleavage. Sequences shown in (a) include, from top to bottom, Wild type: AEGDDPAKAAF-DSLQASATEY (SEQ ID NO:3), Mutant 1: AAAAAPA-KAAFDSLQASATEY (SEQ ID NO:30), Mutant 2: AEGD-DAAAAAFDSLQASATEY (SEQ ID NO:31), Mutant 2: AEGDDPAKAAAAAAASATEY (SEQ ID NO:32), and Mutant 4: AEGDDPAKAAFDSLQAAAAAA (SEQ ID NO:33). b, Structural analyses of G8P$_{EX}$. Upper panel, cartoon showing the structure of G8P$_{EX}$ (PDB entry 2MJZ) and residues 6-11 displayed as stick. This figure is generated by PyMOL. Lower panel, circular dichroism (CD) spectra of wild-type (WT) and mutant 2 G8P$_{EX}$ peptides. c, Identification of the interface between SpCas9 and crosslinked G8P$_{EX}$ by mass spectrometry analyses. SpCas9 structure in complex with the inhibitory protein AcrIIA4 (PDB entry 5VW1) is shown by PyMOL. AcrIIA4 is shown in blue. The candidate G8P$_{EX}$ binding sites on SpCas9 are shown in green and red respectively. d, Alanine scan determines the importance of KSVKEL (SEQ ID NO:23) and EKNPID (SEQ ID NO:34) sites for the catalytic activity of SpCas9 nuclease. Arrow indicates cleavage product.

To understand the mechanism of inhibition, this example performed alanine scan on the 21 amino acid G8P$_{EX}$ peptide. Four peptide mutants were designed, carrying consecutive alanines at different segments of G8P$_{EX}$. Although mutants 1, 3 and 4 displayed limited or no reduction on the inhibitory activity toward Cas9, alanine mutations at positions 6-11 in mutant 2 abolished the inhibitory activity of G8P$_{EX}$ (FIG. 2a). Because this segment contains three native alanine residues, the other three residues P6, K8 and F11 must play critical roles for the inhibitory activity of G8P$_{EX}$. Structural analyses reveal that position 6-11 of G8P$_{EX}$ is located at the N-terminus of an α-helical structure. Circular dichroism (CD) spectra illustrated that alanine mutations at this region prevented the formation of the α helix (FIG. 2b). This α-helical structure may be required for the interaction between G8P$_{EX}$ and Cas9.

Figure 6:
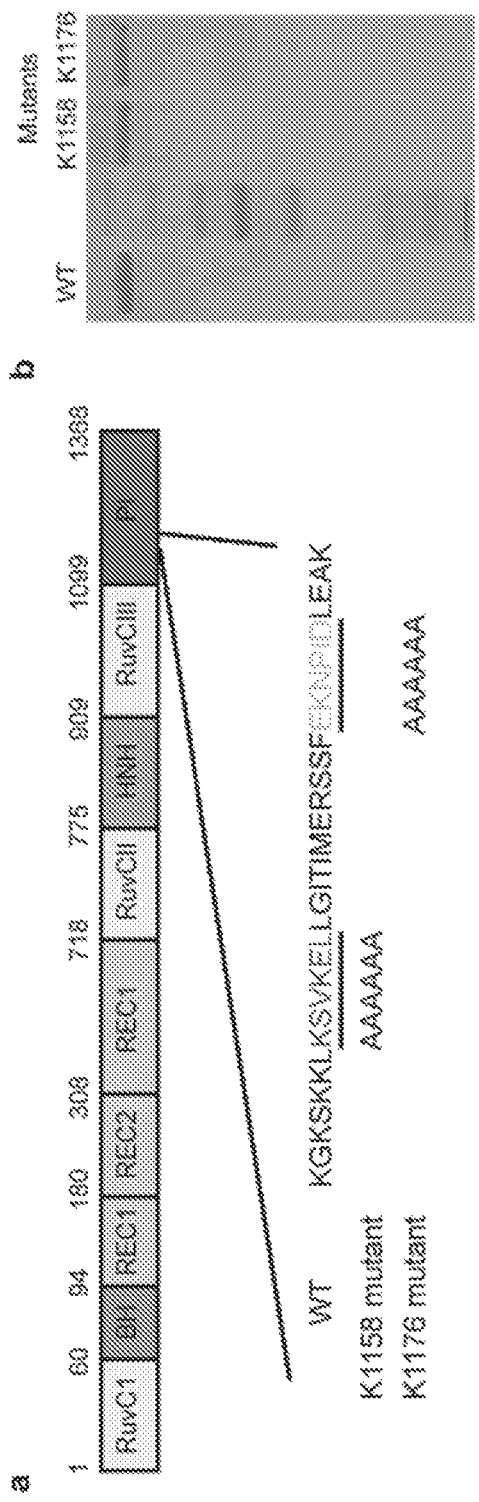
FIG. 6. Construction and purification of KS and EK mutants of SpCas9. a, Schematic presentation of the domain organization of *S. pyogenes* Cas9. BH, bridging helix. PI, PAM interacting domain (KGKSKKLKSVKELLGITIM-ERSSFEKNPIDLEAK; SEQ ID NO:26). Position of alanine mutations in KS (KGKSKKLAAAAAALGITIMERSS-FEKNPIDLEAK; SEQ ID NO:35) and EK (KGK-SKKLKSVKELLGITIMERSSFAAAAAALEAK; SEQ ID NO:36) mutants. b, Purified WT, KS mutant and EK mutant of SpCas9 proteins.

Next the example sought to examine the binding region of G8P$_{EX}$ on SpCas9. SpCas9 and G8P$_{EX}$ were crosslinked using collision-induced dissociation (CID)-cleavable crosslinker disuccinimido sulfoxide (DSSO). The crosslinked products were digested with Chymotrypsin. The integration analyses of CID-induced cleavage of interlinked peptides in MS/MS and MS$^3$ of single peptide chain fragment ions revealed the crosslinking residues K1158 of [K]SVKEL peptide and K1176 of E[K]NPIDFLEAKGY from SpCas9 (FIG. 5). These peptides occupy a continuous region in the protospacer adjacent motif (PAM)-interacting (PI) domain that is responsible for recognizing the PAM sequence on the non-complementary DNA strand (FIG. 2c and FIG. 6). Interestingly, this candidate G8P$_{EX}$ binding site is distal from the sgRNA and DNA binding pocket of Cas9. This suggests that G8P$_{EX}$ may suppress Cas9 activity as an allosteric inhibitor, a mechanism that is distinct from the previously identified Acrs which bind to the DNA binding pocket of Cas9 as DNA mimics. These two sites were mutated respectively into alanines and the mutants were purified (FIG. 6). In vitro cleavage reaction showed that alanine mutation at position KSKVEL (K1158 mutant) abolished the cleavage activity, indicating the importance of G8P$_{EX}$ binding site for SpCas9.

Figure 3:
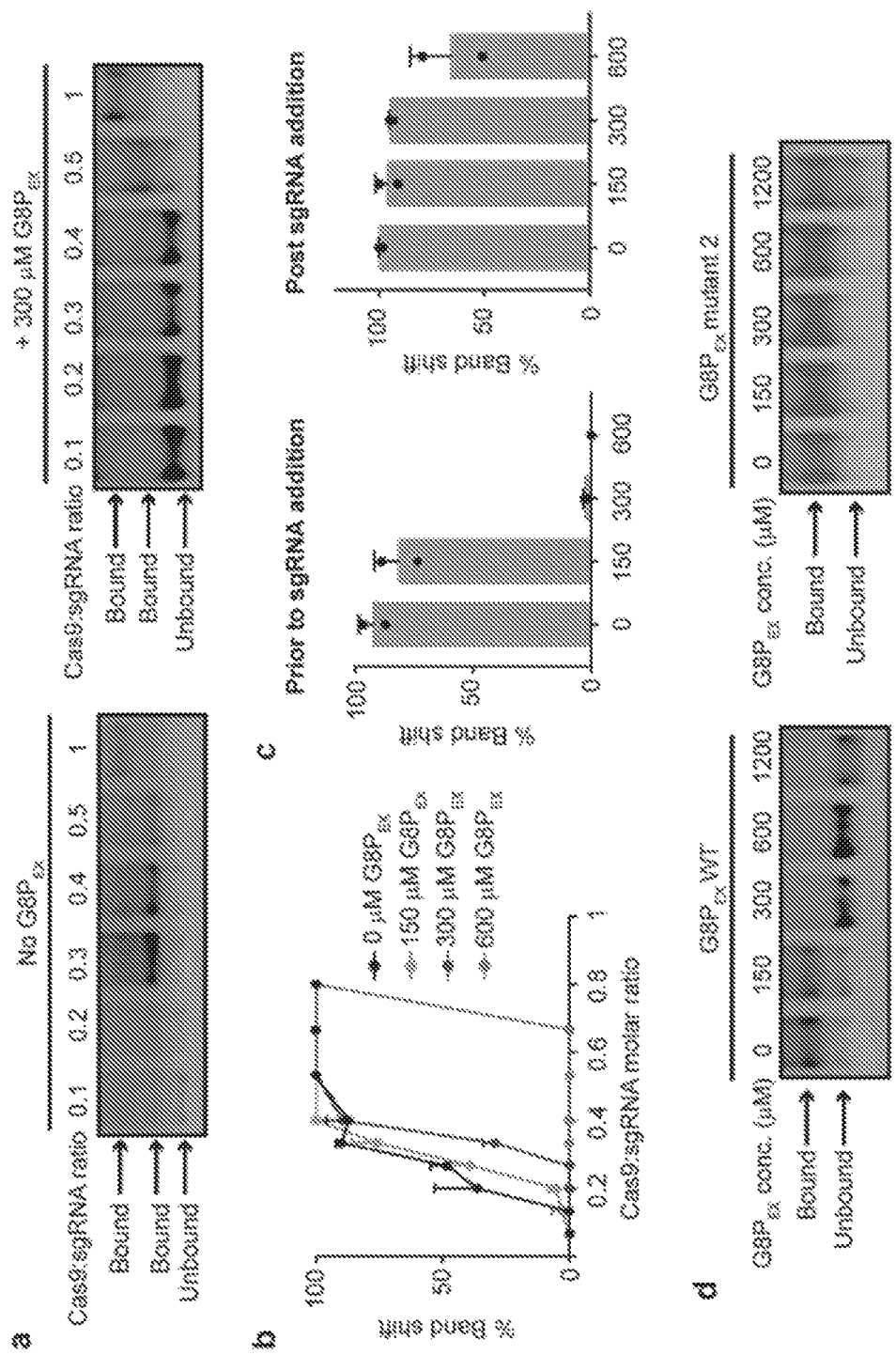
FIG. 3. Effects of G8P$_{EX}$ on Cas9-sgRNA binding. a, EMSA showing the disruption of Cas9-sgRNA binding by G8P$_{EX}$. b, Dose-dependent inhibition activity of G8P$_{EX}$ on Cas9-sgRNA binding. The results are shown as mean±SD (n=2). c, The differential inhibiting effects of G8P$_{EX}$ on Cas9-sgRNA binding prior to or post sgRNA addition. d, Diminished inhibitory activity of G8P$_{EX}$ mutant 2 on Cas9-sgRNA binding.

SpCas9 adopts a RNA induced structural conformation change for catalytic activation. K1158 and K1176 were located on the opposite surface of the stem loop 1 and 2 binding region, therefore this example analyzed the G8P$_{EX}$ effect on the binding between Cas9 nuclease and sgRNA. Gel electrophoresis mobility shift assay (EMSA) was performed using fixed concentration of sgRNA and increasing concentration of Cas9 protein. In the absence of G8P$_{EX}$, gel shift was observed starting from a Cas9:sgRNA molar ratio of 0.1. In the presence of 300 µM G8P$_{EX}$, gel shift of Cas9-bound sgRNA was observed at higher Cas9:sgRNA molar ratio, suggesting a perturbed interaction between Cas9 and sgRNA (FIG. 3a). The inhibitory effects of G8P$_{EX}$ on Cas9-sgRNA interaction is concentration dependent. With the increase of G8P$_{EX}$ concentration, Cas9-bound sgRNA complex was formed at higher molar ratio of Cas9 to sgRNA (FIG. 3b).

Similar to the cleavage reaction, the suppression of Cas9-sgRNA interaction by G8P$_{EX}$ is dependent on the sequence of sgRNA addition. Under a fixed Cas9:sgRNA ratio of 0.4, incubation of Cas9 with G8P$_{EX}$ prior to sgRNA addition resulted in complete suppression of the formation of Cas9/sgRNA complex at G8P$_{EX}$ concentrations of 300 and 600 µM. By contrast, when supplemented post sgRNA addition, G8P$_{EX}$ did not achieve complete inhibition at concentrations of 600 µM or below (FIG. 3c). These results suggested that G8P$_{EX}$ did not directly compete with sgRNA for Cas9 binding. In addition, G8P$_{EX}$ mutant 2 carrying alanine mutations in P6 to F11 residues showed abolished inhibitory activity toward the formation of Cas9/sgRNA complex (FIG. 3d). This result is consistent with the in vitro cleavage (FIG. 2a) and provided further evidence that G8P$_{EX}$ inhibit the nuclease activity of Cas9 by perturbing its interaction with sgRNA. Collectively, the above results suggest that G8P$_{EX}$ suppresses Cas9 activity by disrupting Cas9-sgRNA interaction in an allosteric manner.

Figure 7:
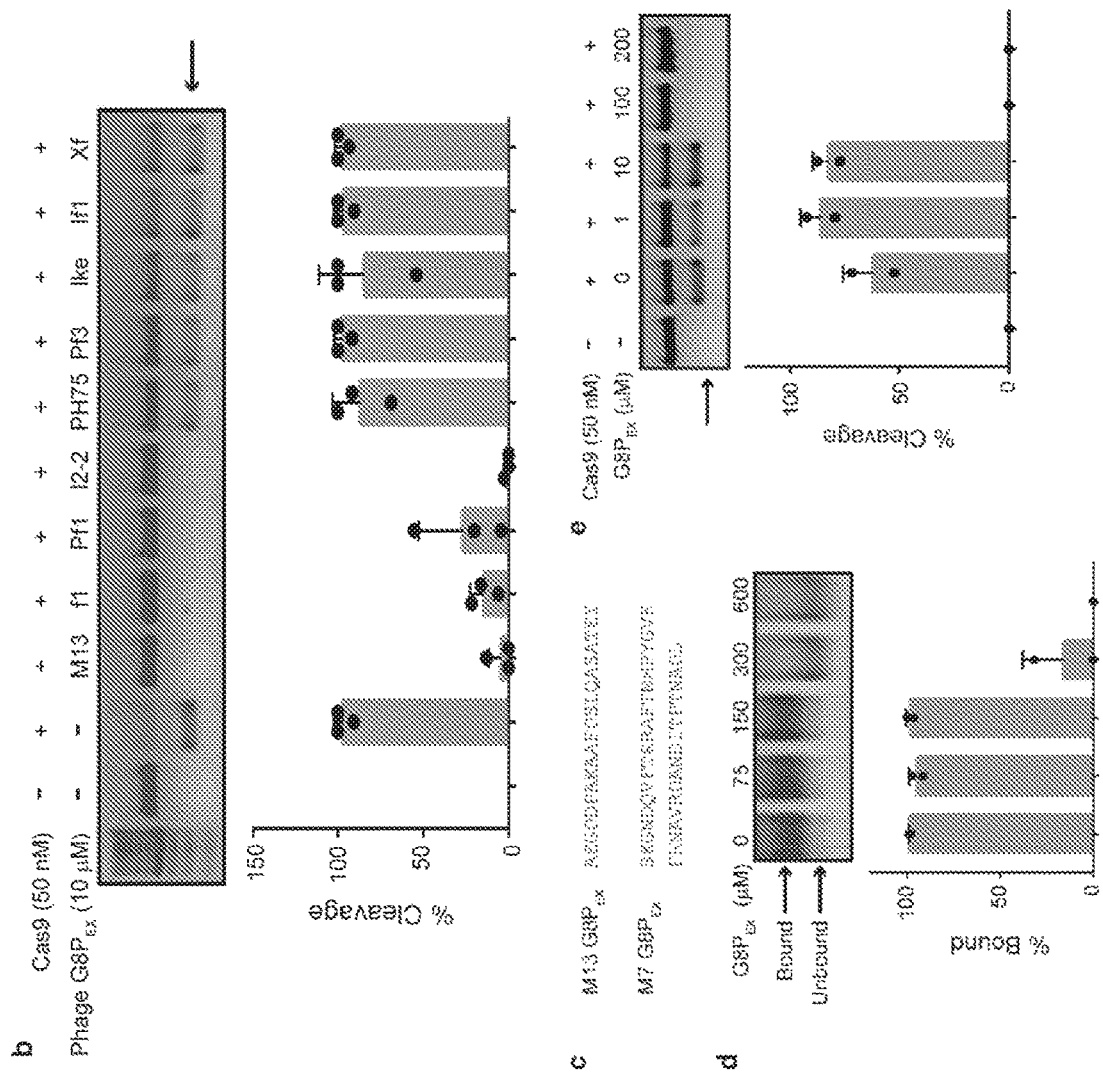
FIG. 7. Investigation of selected G8P$_{EX}$ orthologs. a, List of selected G8P$_{EX}$ (SEQ ID NO: 1-10 in last column, from top to bottom). b, In vitro cleavage reactions showing the inhibitory activity of different G8P$_{EX}$ on SpCas9. The results are shown as mean±SD (n=2). Arrow donates cleavage products. 10% DMSO is included as a control for the solvent. c, Amino acid sequence of M13 (SEQ ID NO:1) and M7 (SEQ ID NO:21) G8P$_{EX}$ peptides. d-e, Inhibition of sgRNA binding (d) and DNA cleavage activity (e) of SpCas9 by M7 G8P$_{EX}$. The results are shown as mean±SD (n=2).

To investigate whether G8P$_{EX}$ is a general approach used by bacteriophage for CRISPR/Cas inhibition, this example analyzed several G8P$_{EX}$ peptides from Inoviridae bacteriophages (SEQ ID NO:2-10) (FIG. 7a). It was found that in addition to the M13 bacteriophage G8P$_{EX}$ (SEQ ID NO:1), the G8P$_{EX}$ from bacteriophage Pf1 (SEQ ID NO:2), f1 (SEQ ID NO:3) and 12-2 (SEQ ID NO:9) could efficiently inhibit the cleavage activity of SpCas9 in vitro (FIG. 7b). Importantly, the G8P$_{EX}$ ortholog peptide (SEQ ID NO:21) from *L. monocytogenes* (strain M7) bacteriophage M7 (FIG. 7c) efficiently prohibited SpCas9 to bind to sgRNA (FIG. 7d) or cleave DNA substrate (FIG. 7e). These results suggest that the major coat protein G8Ps are widely existing CRISPR inhibitors in bacteriophages. MS analyses of Cas9 protein crosslinked with the G8P$_{EX}$ from Pseudomonas phage Pf1 identified the same binding site (FIG. 8) as observed with M13 bacteriophage G8P$_{EX}$, supporting that G8P$_{EX}$ inhibits Cas9 activity in an allosteric mode.

Figure 4:
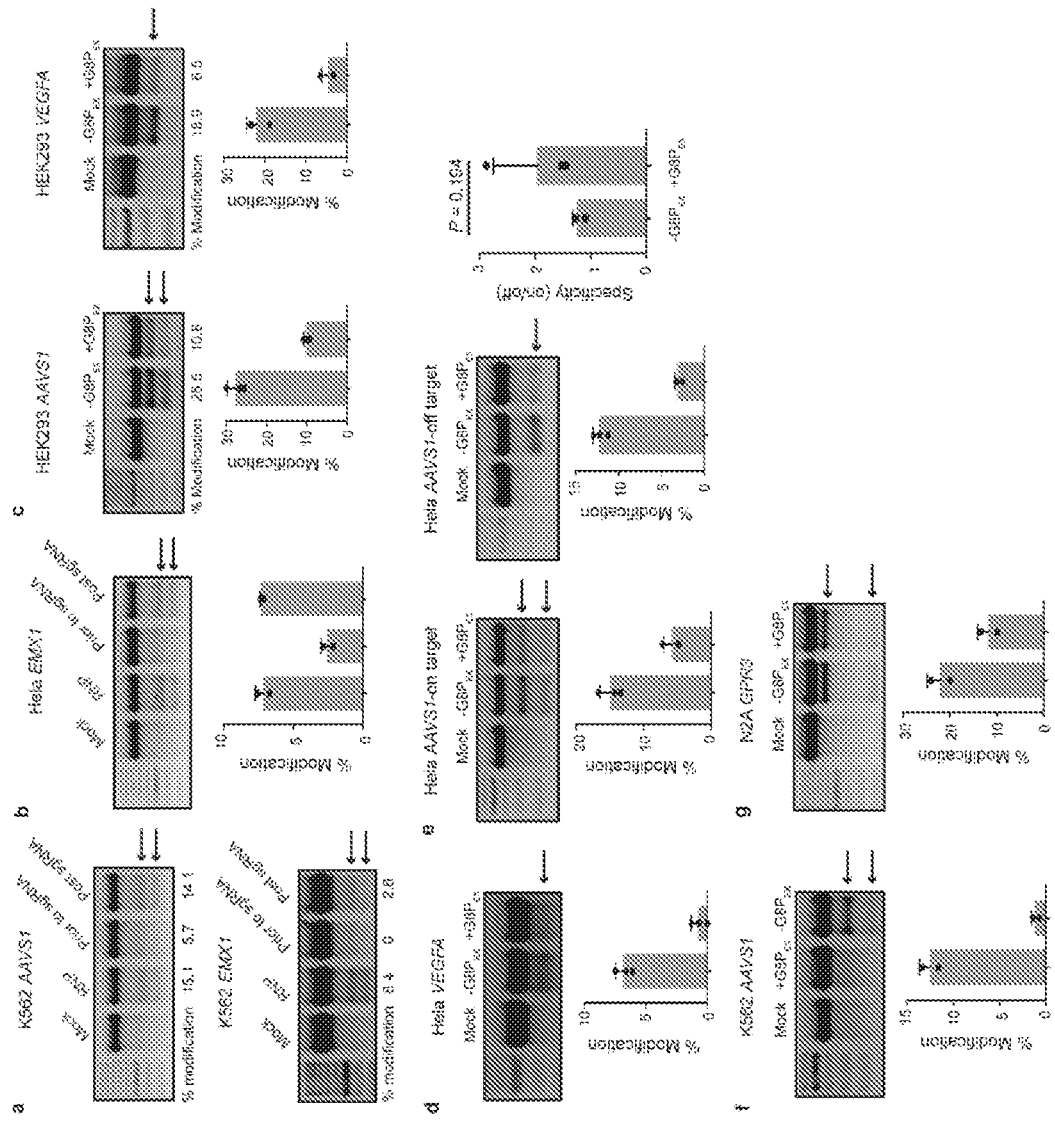
FIG. 4. Inhibition of the genome-editing activity of CRISPR/Cas in mammalian cells by G8P$_{EX}$. a-b, Inhibition of the genome-editing activity of nucleofected Cas9/sgRNA RNP in K562 (a) and Hela (b) cells by co-delivery of G8P$_{EX}$ peptide. c-d, Inhibition of the genome-editing activity of transiently transfected CRISPR/Cas9 in HEK293 (c) and Hela (d) cells by overexpression of G8P$_{EX}$. e, The effects of G8P$_{EX}$ overexpression on the specificity of CRISPR/Cas9. Significant difference between the specificity of CRISPR/Cas9 in the absence or presence of G8P$_{EX}$ is examined by Student's t test. f-g, Inhibition of the genome-editing activity of transiently transfected CRISPR/Cas12a (Cpf1) in K562 (f) and mouse N2A (g) cells by overexpression of G8P$_{EX}$. The results are shown as mean±SD (n=2 or 3). Arrows indicate the cleavage products in T7E1 assays.

To explore the applicability of G8P$_{EX}$, this example evaluated the effects of G8P$_{EX}$ on the genome editing activity of CRISPR/Cas in mammalian cells. The example first examined whether G8P$_{EX}$ could suppress the cellular activity of nucleofected SpCas9 protein as co-delivered peptides. T7E1 analyses showed that G8P$_{EX}$ peptide inactivated SpCas9 proteins across different genes and cell types (FIG. 4a-b). In consistency with the in vitro studies, G8P$_{EX}$ peptides abolished the genome editing activity of SpCas9 proteins when supplemented prior to, but not post, the formation of Cas9/sgRNA RNP complex (FIG. 4a-b). These data further support the notion that G8P$_{EX}$ inhibit the activity of Cas9 as indirect competitor to sgRNA or DNA. Next, this example evaluated the effects of overexpressed G8P$_{EX}$ on transiently transfected CRISPR/Cas9. Cas9 and sgRNA-coding plasmids were transiently transfected into human cells by lipofection and at 6 h post transfection G8P$_{EX}$ overexpression plasmid was transfected. It was found that G8P$_{EX}$ inhibited 50% or more of the genome-editing activity of transiently transfected SpCas9 across various genes and cell types (FIG. 4c-d). Importantly, G8P$_{EX}$ inhibited the activity of Cas9 without compromising its specificity, as evidenced by the on/off cleavage activities in the absence or presence of G8P$_{EX}$ (FIG. 4e). To investigate whether G8P$_{EX}$ is general off-switch to different CRISPR/Cas system, this example examined its inhibitory effects on CRISPR/Cas12a (Cpf1). It was found that G8P$_{EX}$ inhibited the genome-editing activity of Cpf1 in human and mouse cells (FIG. 4f-g).

Figure 8:
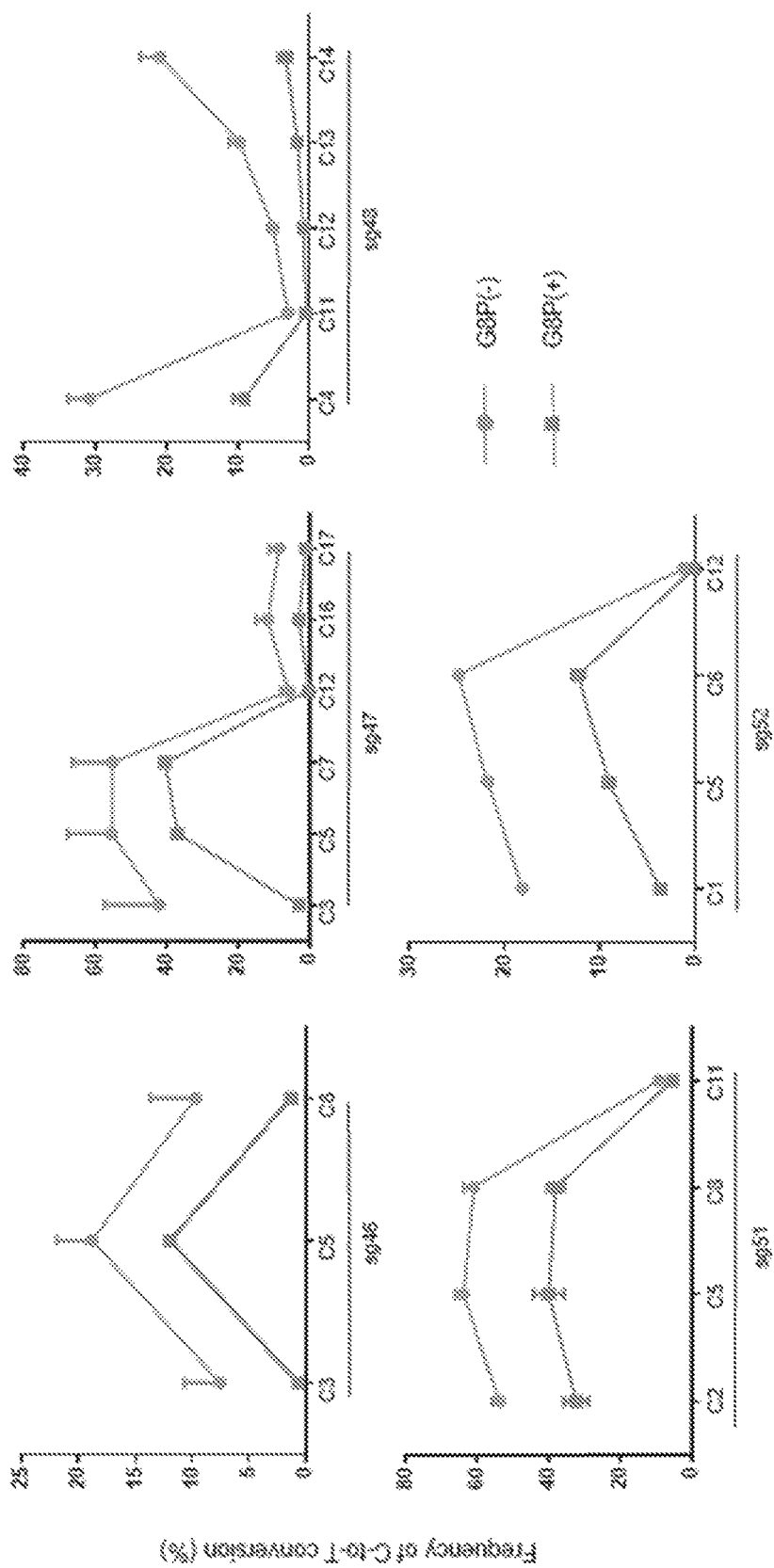
FIG. 8. G8P$_{EX}$ inhibit the activity of A3A cytidine base editor (CBE, hAPOBEC1-nCas9-UGI) for C-to-T conversion in HEK293 cells. Multiple sgRNA and targeting sites are analyzed by next-generation sequencing. The data of two or three biological replicates are shown mean±SD.

In addition to inhibiting the DNA cleavage activity of CRISPR/Cas9, G8P$_{EX}$ can also be employed to modulate the activity of Cas9-derived base editor. We show that the G8P$_{EX}$ can inhibit the C-to-T conversion induced by A3A cytidine base editor (CBE, hAPOBEC1-nCas9-UGI) in HEK293 cells. The inhibitory activity was observed across multiple genomic sites with different sgRNA (FIG. 8). Moreover, within the same targeting sites, G8P$_{EX}$ exhibited different degree of inhibition at different cytidine positions.

Figure 9:
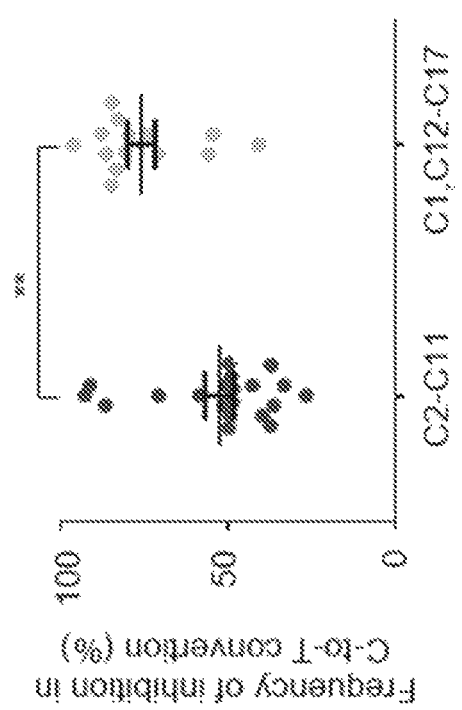
FIG. 9. G8P$_{EX}$ can improve the targeting specificity of A3A CBE. G8P$_{EX}$ treatment had significantly more inhibition at the out-of-window sites (C1, C12-C17) than at the on-target sites (C2-C11). Multiple sgRNA and targeting sites are analyzed by next-generation sequencing. The data of two or three biological replicates are shown mean±SD.

A3A CBE can induce C-to-T conversion at on-target sites (positions 2-11) within the 20-bp targeting site. In addition, A3A CBE can induce C-to-T conversion at out-of-window sites (positions 1 and 12 to 20). Surprisingly, we found that G8P$_{EX}$ displayed significantly more inhibition at the out-of-window sites than at the on-target sites (FIG. 9). In other words, in the presence of G8P$_{EX}$ the ratio of on-target and out-of-window targeting was increased. This suggests that G8P$_{EX}$ can be used to improve the targeting specificity at the on-target sites.

Example 2

Search of G8P$_{Ex}$ Homologue Sequences

The G8P$_{EX}$ sequences successfully tested in Example 1 were used as input sequences to search for homologues. The NCBI BLAST™ program was used, with the following parameters (Expect threshold: 10, Word size: 6, Max matches in a query range: 0, Matrix: blosum62, Gap Costs: Existence:11 Extension: 1, Compositional adjustments: Conditional compositional score matrix adjustment).

Four hundred significant hits were identified, as listed in Table 2 below. It is contemplated that these sequences and their variants also have the ability to bind to Cas proteins and inhibit their function to bind to nucleic acids.

TABLE 2

G8P$_{Ex}$ Homologues

| SEQ ID NO: | Sequence |
|---|---|
| 37 | GTATATS |
| 38 | MDFDPSE |
| 39 | MDFNPSEV |
| 40 | MEFNPSDV |
| 41 | PSEVASQV |
| 42 | SQVTNYIQ |
| 43 | ASQVTDYIQ |
| 44 | DFNPSAVAS |
| 45 | FNPSDVAPQ |
| 46 | FDPSEVAPQ |
| 47 | MDFDPSEVA |
| 48 | MDFEPSEVA |
| 49 | NPAEVASQV |
| 50 | PSEVASQVT |
| 51 | TQATDLLDQ |
| 52 | DFNPTDVASQ |
| 53 | DFNYPSEVAS |
| 54 | DTSAIEAAIT |
| 55 | EAASQVTNYI |
| 56 | MDINPSDIAS |
| 57 | MNALKTTDLI |
| 58 | NPSEVAPQVT |
| 59 | PAFAGVIDTS |
| 60 | SAASSYAAEA |
| 61 | SAADSYDADA |
| 62 | ALTEAQGDMKA |
| 63 | DDGTATATSYA |
| 64 | DSLKTQAIDLI |
| 65 | EDEAKAAFEAL |
| 66 | EVAAQVTDYLQ |
| 67 | EVVSDLTNYIQ |
| 68 | FNPSEIPSQIT |
| 69 | GTPTATSYATE |
| 70 | GTSAATSYDTE |
| 71 | MDFDPSELAYI |
| 72 | MDFNPEMASSV |
| 73 | MDFNPSDIAYI |
| 74 | MNSLKNHTDLI |
| 75 | MSFNPEVASQV |
| 76 | NDGTSTATSAT |
| 77 | NFNPQVTNYIE |
| 78 | NPSEVASQIIQ |
| 79 | PSAVQVTNYIQ |
| 80 | SEVGGNMTSYI |

TABLE 2-continued

G8P_FY_ Homologues

| SEQ ID NO: | Sequence |
|---|---|
| 81 | SQVASQVTDYI |
| 82 | TEIMGSLKTQA |
| 83 | AADSLQASATDY |
| 84 | AMNSLKENDLID |
| 85 | DDASSNATSYAT |
| 86 | DDGTANATSYAT |
| 87 | DFNLSEVAAQVT |
| 88 | DFVASQVTNYKQ |
| 89 | EVASQLLGTNYI |
| 90 | FNPPTVTSQVTN |
| 91 | GTSTTTTYTDAM |
| 92 | IDTSLIEAAITD |
| 93 | LDLSPSEVASQV |
| 94 | LPAFAGVIDVES |
| 95 | MDEISQITDYIQ |
| 96 | MDFTPSEVARNV |
| 97 | NPNEVSRQVNYI |
| 98 | NPREIASQVSDY |
| 99 | NPSEVASQIIIQ |
| 100 | NSSEVASQVANY |
| 101 | PAKAAFDLQATA |
| 102 | SEVASQVQNFIQ |
| 103 | SFATEVMNSLPT |
| 104 | SYATSMNNLKKQ |
| 105 | TASSYATQAQKS |
| 106 | MGDILTGVSGAE |
| 107 | AGLIDTASVESDI |
| 108 | AGLIDTSSVDNAI |
| 109 | AGLIDTSSVEKSI |
| 110 | AGLIETSSVERSI |
| 111 | AGLIDTSSVESSI |
| 112 | AGLIDTSTVDSTI |
| 113 | AGMIDSSSVDSAI |
| 114 | AGMIDTSSIDSSI |
| 115 | DDGTTTAYATDEA |
| 116 | DFDPSEVEQVVNY |
| 117 | DFNPAEVAKRNYI |
| 118 | DFNPSEIAKRNYI |
| 119 | DFSPAEVAKRNYI |
| 120 | DFSQSEVDQQVTN |
| 121 | DSGTSAATSYDTE |
| 122 | FLGVIDNSESAIT |
| 123 | FNPNEVLASQSTN |
| 124 | FNPSEVAALTSFI |
| 125 | FNPSEVPSIGNYI |
| 126 | MDDFNPAEVARQI |
| 127 | MDFYQKNPSAVAS |
| 128 | MSFNSESASQVTN |
| 129 | MSFSPSEIASEIQ |
| 130 | PSEVAAQIVNYYQ |
| 131 | SAVESAFNEGEGD |
| 132 | TSYATNSINSLNT |
| 133 | TSYATSSINSLNT |
| 134 | VLDTSEVESPITE |
| 135 | ADEGTTATTYAVDA |
| 136 | AEDGTTATTYAVEA |
| 137 | ADEGSSATSYAVDA |
| 138 | AFCGVIDTSAVASA |
| 139 | AGDGTTTATIYAEA |
| 140 | AGEGTSTATVYAEA |
| 141 | AKAAFDSLTAQATE |
| 142 | ASVADSSAAESAIT |
| 143 | DMTAVNSAITAGQG |
| 144 | FNPTEVVQVTQYLQ |
| 145 | FSPEVISQITEYIQ |
| 146 | GQATATSYATQTQA |
| 147 | GVIDASAVERAIAD |
| 148 | LNFEISEVASQVTN |
| 149 | MDFNRSGVTSSVTN |
| 150 | MDINSSEVATDFYI |
| 151 | MGFNPSIDVRQVTN |
| 152 | NPNEVAEHVTAYIE |
| 153 | NPSDIASQVADYFQ |
| 154 | PSEIANQITNYLIQ |

TABLE 2-continued

G8P_FY Homologues

| SEQ ID NO: | Sequence |
|---|---|
| 155 | TSLPVFNAGYIDTS |
| 156 | AGVIDRSALQSAMKA |
| 157 | AKAAFEALRAAETEY |
| 158 | AKEAINSLKTQSKDL |
| 159 | AMKSILKTTADLVDQ |
| 160 | ATEAMDSLETQTATD |
| 161 | DAAKAAFDSLKAGAT |
| 162 | DAAKAAFESLKTGAT |
| 163 | EAAKAAYDSLKAGAT |
| 164 | DAAKAAYDSLRAGAT |
| 165 | DAAKAAYDTLKAGAS |
| 166 | DDARAAFDSIKSGAT |
| 167 | DGTSTATATSSEAAN |
| 168 | DPTNAAFDSLAAGAT |
| 169 | EAMNKLKAQAKEVID |
| 170 | EAMNVLSILETDLID |
| 171 | EAMNVLSLLKTELIE |
| 172 | EAMTNLDTQAINAID |
| 173 | EGADPAAVAFDSLQA |
| 174 | DGSEPAAVAFDALQA |
| 175 | EGSDPAAVAFETLQA |
| 176 | FNPSETISQLTHYIE |
| 177 | LPAFLGIIATSTVSA |
| 178 | MGFNPFVSEVAHQLT |
| 179 | MHFNVSDAANQITNY |
| 180 | NPEVADSSQCTSYIQ |
| 181 | NPSEIALSDVANFIQ |
| 182 | QAMNEALKTSATDLI |
| 183 | QGNDPDVKAAFDSLQ |
| 184 | TAVSIATEAMDRLRT |
| 185 | TEIMNSLKNSDTDLI |
| 186 | TSLPAFAALIDSAAV |
| 187 | TSTATSYSTELRTAM |
| 188 | ATALPAFATSAVAAIT |
| 189 | ATSFSTEAVNSLTNLI |
| 190 | ATSYATAEPMDATQAT |
| 191 | DFLNPSEVASLQQVYN |
| 192 | DFNPSASADVAAAITN |
| 193 | DGTSSTSYETVPLNSL |
| 194 | EAMNSLTTQAKADLLE |
| 195 | GIIDTNVVQSAISDAQ |
| 196 | GVIRDTPEAVESAFTD |
| 197 | MDFNPSEIATTVVQYI |
| 198 | MEFHADEVAANVTGYI |
| 199 | MGFNPREVSKQVIENY |
| 200 | MSFNSEVLNASQITDY |
| 201 | NFNASEPSQLVTKYIQ |
| 202 | TAISYQTEAMQSLQIQ |
| 203 | VIDASNVEKAFIITDG |
| 204 | VTDTSEAAITDKHGDM |
| 205 | YATELSSLTTQVSQLI |
| 206 | YATKALNSVKTANDDQ |
| 207 | YATKSLNSVKTSNEEQ |
| 208 | YATNALNSVRTANEDQ |
| 209 | ATEALNEFKTQITDLAD |
| 210 | ATSLPAFAGVIDTSAVE |
| 211 | DDGSTSDGTSYATNVLK |
| 212 | DDPATAAFDGGPSLTEY |
| 213 | DFNPSKVAQDPKVTAYI |
| 214 | DENTSTELAGQVTDYFQ |
| 215 | DESGSEVAAQTNLGVTN |
| 216 | DESQSEIAAAGAVTDYI |
| 217 | EEEDPADAAFPTLQASA |
| 218 | FNPSVEIGSQQNVTDYV |
| 219 | GVIDSAPVVQSAITNGQ |
| 220 | LPAFTGVKIDVEGAVIT |
| 221 | MNSLKTQAEELVMTELI |
| 222 | SKATSFKATEPALNSLK |
| 223 | TDAKNELTTQVTDLTTQ |
| 224 | TEGMNSLKTLASQLTDQ |
| 225 | TESLQSLKAQIMDLIDQ |
| 226 | TETLQSLMKSQATDLLN |
| 227 | TEVLNFLKTQTDLVIDQ |
| 228 | VFDSSAADKAIQGDLKA |

TABLE 2-continued

G8P_FX Homologues

| SEQ ID NO: | Sequence |
|---|---|
| 229 | VTDTSAIEAAVVQIITD |
| 230 | YAEASLKTTATREDLIE |
| 231 | MDFNPSEVASQVTNYIQ |
| 232 | AAGDDPAVAAVQTAATEY |
| 233 | AATLRIFAIDTTAVESAI |
| 234 | ASDGTSSTSYETVPVNSL |
| 235 | ATQAANNLATQATNLVNQ |
| 236 | DFNPAEVAKTLSSENITN |
| 237 | DGDTATANSYLTEAANSL |
| 238 | EDDDAVKAAFDKLQASQT |
| 239 | EEEEAVKAAFEKLQASQT |
| 240 | EDDEAVKSAFDKLQASQT |
| 241 | EGDDDAAVKAAFEKLQAS |
| 242 | EGTDDAAVKAAFEKLQAS |
| 243 | FSPTEVASLLDVGTNYVQ |
| 244 | IDTSAIENAVKKSDGQGE |
| 245 | IDTSATETAVRKSDGQGE |
| 246 | MDFLLNPENIAAVTNYAQ |
| 247 | MEFLYKPDVAAELTDYIQ |
| 248 | MDYLVPSPTEVPSMVTDY |
| 249 | MFNPSVEIGSQQNVTDYV |
| 250 | QAMDSLKTATASVADLLD |
| 251 | SEVAAAKQRHQQVTNYIQ |
| 252 | SNATEAKNGLKKQATDLI |
| 253 | TNMSTAYAFLEAINSLKT |
| 254 | TSAVASADTDGSDDQGDM |
| 255 | MQSVITDVTGQLTAVQAD |
| 256 | AELGDDPAAAIDALAAAAT |
| 257 | AGVINTAVIEQAITDASDM |
| 258 | DFYPSELAGQIDQLADYIQ |
| 259 | EALSSLKIKIDDQPTDLID |
| 260 | EEMAAAANSLKTQAKELVD |
| 261 | EGDDPLSRLARASLQASAT |
| 262 | FNPSENASKLTNRNIHYIQ |
| 263 | IDTSSASSIAAAEASIAAG |
| 264 | LPGFLGVIDTAISKIESVI |
| 265 | MEINPSEVTKILKEQIKNY |
| 266 | MEINPSEVTKILKDQIRNY |
| 267 | MQSLKTQEEEKRKADLVDQ |
| 268 | TAITSYATENATQMNSIKT |
| 269 | TKYETEAKHLKSLETQGTD |
| 270 | TSLPSISGGIETSESAGTD |
| 271 | TTTGYGMNSLKSKETNLID |
| 272 | SGVGDGVDVVSAIEGAAGP |
| 273 | ADDGEGFTGSTTEAMNKLKT |
| 274 | AEGEGASAVFTALQAKATEY |
| 275 | AGDGTTTATVLTQSIATEGM |
| 276 | AGEGTTTATVLTQSIATDGM |
| 277 | ASVISTRNVETAMKNGQGDL |
| 278 | DDASSTVESATSSATEAMES |
| 279 | DDATSQAKAAFDSLTAQATE |
| 280 | DDPNATAAFESLQADIAANE |
| 281 | DTSSESATESAVGQGDLAMK |
| 282 | EGTDDDAVKAAFEKLQASQT |
| 283 | MDFNPSEQGAKVLKQVTDFV |
| 284 | MQFNPYEISSQIKQNGGYIQ |
| 285 | TSLPGVIGAAAVQSAKTEGQ |
| 286 | VIDVSSASHVQSFVESAITD |
| 287 | YSTEDAAAMNAADGLKTQAT |
| 288 | AAGNDRVFTRRAFTMHPYGVK |
| 289 | ADQGTMTATDYATYTSLFEAM |
| 290 | APGEDPEARAAYDEMQAAAAE |
| 291 | DDGTATIGVSAYAVEALTDLV |
| 292 | DGYGKATSFSTEAVNSLTNII |
| 293 | GVIDTSAVESAITDGQGDMKA |
| 294 | LDFNSSEVALSEGMQVTSFLQ |
| 295 | LPDFAGVVDDYDEFTDAVESA |
| 296 | TGLPHAFPAVSGASAVESAIT |
| 297 | TGLPHAFPAVSGASAVESAIT |
| 298 | TSAEATYEKAMNALKIQATDL |
| 299 | AEGDDPAKAAFDSLQASATEY |
| 300 | AEGDDPAKAAFNSLQASATEY |
| 301 | AEGDASSQAKAAFDSLTAQATE |
| 302 | AEGDATSQAKAAFDSLTAQATE |

TABLE 2-continued

G8P_FY Homologues

| SEQ ID NO: | Sequence |
|---|---|
| 303 | ADGEATSQAKVAFDSLTAQATE |
| 304 | AGDGTTTATVLTQAIATEGMKS |
| 305 | ATNYATEAMDSLKTQAIDLISQ |
| 306 | ATPLPAFTVDVESGITDPTSGQ |
| 307 | DGSTSYTLDTLDSLKTQGTEII |
| 308 | EGSDPAATVFDSLQAAKARGTE |
| 309 | GTSTTAFYDRATIDMNALRTQA |
| 310 | GVDELWVRRQFVMHPYGIKWTD |
| 311 | IIDAGAVISGITDGYQGSAPDM |
| 312 | IIEAGTVISGITEGYQGSSPDM |
| 313 | TSTATGPIIYAAEAINSGADLI |
| 314 | TSTATSYDGEAVVTSLKTSTAL |
| 315 | ADDATSQAKAAFDSLTAQATEM |
| 316 | ADDGDDTTTATTSATEPVASIKT |
| 317 | ADSSTDYAGQAMDSLLTQANDLI |
| 318 | AFTQPIDTSAIETAIIDQSKGQG |
| 319 | AGDGTTTATVLAYAMVREGMKNL |
| 320 | STGGTDYAGQAMDALLTQANDLI |
| 321 | TATNYATEAMTSLKTQATDLIAQ |
| 322 | AGDGTTTATVLACSIAKESMNSIK |
| 323 | AKGNDNVFTRRAFVMHPYGVKWTD |
| 324 | ANDGTATATSIETGATEALPTSAT |
| 325 | ASSYADEAKASLKTAGVLASQATD |
| 326 | ATEAMNLWIREKTQEAIARDALDQ |
| 327 | DDGTATSYSVALSLNPYSTEAMDS |
| 328 | DGSATTTSTEARDALKAEATTLED |
| 329 | DNPSKAAYDSLQAQLKRDIEAAEY |
| 330 | DNPSKAAYDSLQAQLKRDLEASEY |
| 331 | EAMSTYRAMRYLKTDEVSTDLIEQ |
| 332 | MTFNPAAVVSPLLLGNASRITNYI |
| 333 | SLPAFIEVIGTSGVDAAIKQYATD |
| 334 | TDLPTIDELGSAGLIDTSTVDSQI |
| 335 | TPLQAFSGVPRTRDTSESPITDGE |
| 336 | TSFAEDAMSSLTTAGPTTATDLLD |
| 337 | TSMPAYTSKALVIDTSPIEKEISN |
| 338 | AFSAVLDTAVTAVENVNAAIEAITD |
| 339 | AGEGASTDYAGQAMDSLLTQANDLI |
| 340 | ATPVFVDVLGNQLIDPNAIEKAITD |
| 341 | ATVPAFAAVVDTAAIQAQIQEGQGD |
| 342 | ATVPAFAAVVDTAAIQTQIQEGQAD |
| 343 | DGTSASTVYVTGALCLLLEAMPGLK |
| 344 | EDVTVTATISYAASPMNGQVVNLIN |
| 345 | GITDTSDVSLVALSDAVESAITETQ |
| 346 | TSNSAESMNSLSKHPQKTPITQLID |
| 347 | AEPNAATNYATEAMDSLKTQAIDLI |
| 348 | ATSSPSYAVIDVTAVTTGITDAQTAM |
| 349 | DDGTVSRFAEDHFLITTTTAYATEAM |
| 350 | SLFGPVFAGIITAAVLSAIMSTADSQ |
| 351 | AADGATGSTDYAGQAMDSLLTQANDLI |
| 352 | AADGATTDYATDAFATLKTTATDMIEQ |
| 353 | AADGSTGGADYAGQAMDALLTQANDLI |
| 354 | AAEGATGGTDYAGQAMDALLTQANDLI |
| 355 | AAEGATGSTDYAGKAMDSLLTQANDLI |
| 356 | AAEGATGSTDYAGQAMDSLLTQANDLI |
| 357 | AEGGAATTPDYAGQAMDSLLTQANTLI |
| 358 | AEPDEEAKAMFDSLAKPALGPGASATE |
| 359 | AEPDEEAKAMFESLAKPALGPGASATD |
| 360 | AFTGTIDVDSAAESLKLFTKTFAITDG |
| 361 | ATALPAWAAVIDTTEVQATFGEAKGDM |
| 362 | ATSLPAFAGVIDTSAVEAAITDGKGDM |
| 363 | ATSLPAFAGVIGAVALALAVGDGDMKA |
| 364 | ATTLPAVATRAGDTWAVEVRISDGEDM |
| 365 | TSVPAFAASVIDTXAVEQAITDGKSDM |
| 366 | TSVPAFAGSVIDTSAVETAITDGKSDM |
| 367 | ADDGTSTHISYMQLHGRVCRFANALKAQ |
| 368 | AFANDDAIDTAVGTAQNVTDTWLAQGDM |
| 369 | ASSMPVWAASVIDTSSVEQAITDGKGDM |
| 370 | ASSVPAWAGSVIDTSAVESAISDGKQDM |
| 371 | ATSLPAFAGVIDTSAVETAMTDGQGDMK |
| 372 | TALPVIETAAGDVSAFVPTNVISITDGQ |
| 373 | TSLPVIETQAGDVSAYIPTNVISITDGQ |
| 374 | AEDPAMQQRSVAAFDALQLSATDAELREY |
| 375 | AEDPAMQQRSVAAFDALQQSATDAELREY |
| 376 | AEDPAMQQRSVAAFEALQESATDAGLREY |

TABLE 2-continued

G8P_FY Homologues

| SEQ ID NO: | Sequence |
|---|---|
| 377 | ASTLPAIATRAGDVWTVEVRITDGEDMSA |
| 378 | DFNIAPGLAPLNGLLLPSEVVSQISSFIQ |
| 379 | STTTSYSSELSVYPSLNSLKETHGQDLID |
| 380 | ATSLPAFAGVIDTSAVESAITDGQGDMKA |
| 381 | ADDGTSTATSYATEAMNSLKTQATDLIDQ |
| 382 | ADDGGSTITSYTVEYATSNSGPWTTHSTNL |
| 383 | MFNPSEVADNLKRSGAFVPGIRPGQQTANYI |
| 384 | DHLETRLAFNYHPFGHTYISAILDANDFTPTS |
| 385 | AGDGTTTATIYAEAIFNEGLKNVVAGADAMSLK |
| 386 | GDDILINRQAFVLHPRGVEFKNASVAGATPSNAEV |
| 387 | GDDILINRQHFILHPRGVKFKNTSVAGSSPTNAEL |
| 388 | GDDILINRQHFLLHPRGVKFNNAAVAGSSPTNAEL |
| 389 | GDDILINRQHFLLHPRGVKFTDKSVAGNSPTNAEL |
| 390 | GDDILINRQHFLLHPRGVKFTDKSVSGSSPTNAEL |
| 391 | GDDILINRQHFLLHPRGVKFTNKSVAGSSPTNAEL |
| 392 | GDDILVNRQHFLLHPRGVKFTNKTVTGSSPTNAEL |
| 393 | GDDILVNRRHFVLHPRGIKFTNASVAGVSPTNAEL |
| 394 | GEDILINRKHFVLHPRGIKFTNASVAKTAPTNAEL |
| 395 | GEDILINRKHFVLHPRGIKFTNATVAKTAPTNAEL |
| 396 | GEDILINRQHFVLHPRGVAFQNASVAGSSPTNAEL |
| 397 | GEDYLINRRTFILHPRGVRFTSGSVAGVSPTNAEL |
| 398 | GGDILYTRRQFVLHPYGIAWQDASVAAEFPTNVEL |
| 399 | GGDILYTRRQFVLHPYGIKWTDASVAGEFPTTAEM |
| 400 | GNDKLYTRRAIVMHPYGLSFEPEELSDFTPTNGDL |
| 401 | GVDYLITRRHFLLHPRGIKFTNSSVAGAAPTNAEL |
| 402 | GIDYLINRKTFILHPRGVKFTNTVRANTETVSRAEL |
| 403 | GVDYLINRKAFILHPRGIAYTGAKRGHVETPTRAEL |
| 404 | GVDYLINRKTFILHPRGIKFTGAVRANQETVSRAEL |
| 405 | QGDDILINRQHFILHPRGVEFKNAAVAGPSPTNAEL |
| 406 | QGDDILINRQHFILHPRGVEFKNAAVASSSPTNTEL |
| 407 | AAGIDEIFTRRAFVYHPYGVKFTSKAVAGLTPSNAEL |
| 408 | AAGNDRIFTRRALVMHPYGIKWTDTSVEGATPSNEEL |
| 409 | AAGNDRVFTRRAFTMHPYGVKFKSTTVAGATPSNAEM |
| 410 | AAGVDELFTRRAFVYHPYGVKFTSKAVAGLTPSNTEL |
| 411 | AAGVDEVFTRRAFVFHPYGVKFTDTTVAGLTPSNTEL |
| 412 | AAGVDEVFTRRAFVYHPYGIKFKSTTVTGETPSNAEL |
| 413 | AAGVDEVYTRRAFVFHPYGIKFTDTTVAGETPSNAEL |
| 414 | AAGVDNVYTRRALTMHPYGVRWQDNSIVGLTPSNAEL |
| 415 | GQDYLVTRRHYVLHPRGIKWDPGSGVPASVTPSDAEL |
| 416 | SKGIDEVYTRRAFVFHPYGVKFTDATVSGETPSNAEL |
| 417 | SSGEDFLINRQIYILHPRGVKFTDTAVADVFPTNAEL |
| 418 | KGNDEVYTRRAFTMHPYGVKFTNADRDSGEITPTNKDL |
| 419 | KGNDEVYTRRAFTMHPYGVKFTNIEREEGEITPTNNDL |
| 420 | AKGNDMIYTRRALVMHPYGVKWTGAEVDAGNITPSNADL |
| 421 | AKGNDQVFTRRAFTMHPYGVKFKNAVRDANEITPTNADL |
| 422 | AKGNDQVFTRRAFTMHPYGVKFTNADREAGEITPTNKDL |
| 423 | AKGNDQVFTRRAITMHPYGIKWTDNLRDDGNITPTNVDL |
| 424 | AKGNDQVFTRRAITMHPYGIKWTDNLREEGNITPTNVDL |
| 425 | AKGNDQVFTRRAITMHPYGIKWTENLREEGNITPTNVDL |
| 426 | AKGNDRIFTRWALTMHPYGVKWNDSTREDGNITPTNVDL |
| 427 | AKGNNNIFTRRAFTMHPYGVKFTNAARESGFITPTNKDL |
| 428 | AKGTDIIYTRRAVTMHPYGVKWKDAEREAGNMTPTNVDL |
| 429 | NKGNDEVYTRRAFTMHPYGVKFTNTDRESGEITPTNKDL |
| 430 | SKGNDQVFTRRAFTMHPYGVKFKNAVRDVNEITPTNADL |
| 431 | SKGNDQVFTRRAFTMHPYGVKFKNAVRDANDITPTNAEL |
| 432 | DGTSYVSSTASPYSATENSTLKGTELIYKFPLAAMNSLKT |
| 433 | DDGSSTASAASVSYRVDGAPGAQVATITLERPEAMNGLDTETKD |
| 434 | YVITGSVNPKRFAYTERGNTQIVIREPFTDHPIYDAFKDCFYDAYDLELD |
| 435 | YVFQGQGNDHRFTTRPFVTGSKKFLFKNQVRDNMIRTLTSAVPIITGYEVFTYWAFANGYLGLFDLG |
| 436 | YVFQGQGNDHRFTTRPFATGSKKFLFKNQVRDNMIRTLASAVPIITGYEVFTYWAFANGYLGLFDLGSS |

The present disclosure is not to be limited in scope by the specific embodiments described which are intended as single illustrations of individual aspects of the disclosure, and any compositions or methods which are functionally equivalent are within the scope of this disclosure. It will be apparent to those skilled in the art that various modifications and variations can be made in the methods and compositions of the present disclosure without departing from the spirit or scope of the disclosure. Thus, it is intended that the present disclosure cover the modifications and variations of this disclosure provided they come within the scope of the appended claims and their equivalents.

All publications and patent applications mentioned in this specification are herein incorporated by reference to the same extent as if each individual publication or patent application was specifically and individually indicated to be incorporated by reference

What is claimed is:

1. A method for improving the specificity of a Cas protein-based genome editing procedure, comprising introducing to a cell undergoing the Cas protein-based genome editing procedure a non-bacteriophage vector comprising a polynucleotide encoding a polypeptide comprising a bacteriophage major coat protein G8P, an extracellular region of the G8P (G8P$_{EX}$), or an amino acid sequence having at least 70% sequence identity to the G8P or the G8P$_{EX}$ and capable of binding to the Cas protein, wherein the Cas protein is a Cas9 protein or a Cas12a protein, and wherein the polynucleotide further comprises an inducible promoter regulating the expression of the polypeptide.

2. The method of claim 1, wherein the Cas protein is selected from the group consisting of SpCas9, SaCas9, NmeCas9, StCas9, CjCas9, AsCpf1, FnCpf1, ScCpf1, PcCpf1, BpCpf1, CmtCpf1, LiCpf1, PmCpf1, Pb3310Cpf1, Pb4417Cpf1, BsCpf1, EeCpf1, variants thereof and chemically modified versions thereof capable of interacting with the polypeptide.

3. The method of claim 1, wherein the Cas protein and the polynucleotide are introduced to the cell simultaneously.

4. The method of claim 1, wherein the polynucleotide is introduced to the cell after the cell has been in contact with the Cas protein.

5. The method of claim 1, wherein the Cas protein-based genome editing procedure is in vitro.

6. The method of claim 1, wherein the Cas protein-based genome editing procedure is in a live subject.

7. The method of claim 6, wherein the live subject is a human subject.

8. The method of claim 1, wherein the polypeptide comprises an amino acid sequence selected from the group consisting of SEQ ID NOs:1-22 or a sequence having at least 70% sequence identity to any one of SEQ ID NOs:1-22 and capable of binding to the Cas protein.

9. The method of claim 8, wherein the polypeptide comprises an amino acid sequence selected from the group consisting of SEQ ID NOs:1-10 and 21.

10. A method of genome editing in a subject, comprising administering to the subject a Cas protein-based genome editing system and a non-bacteriophage vector comprising a polynucleotide encoding a polypeptide operatively linked to an inducible promoter, wherein the polypeptide comprises a bacteriophage major coat protein G8P, an extracellular region of the G8P (G8P$_{EX}$), or an amino acid sequence having at least 70% sequence identity to the G8P or the G8P$_{EX}$ and capable of binding to the Cas protein, wherein the Cas protein is a Cas9 protein or a Cas12a protein.

11. The method of claim 10, further comprising inducing the expression of the polypeptide by activating the inducible promoter after the genome editing with the Cas protein-based genome editing system has initiated.

12. The method of claim 10, wherein the Cas protein and the polypeptide are encoded on a same nucleic acid construct.

13. The method of claim 10, wherein the the polypeptide comprises an amino acid sequence selected from the group consisting of SEQ ID NOs:1-22.

* * * * *

SEQUENCE LISTING

<160> NUMBER OF SEQ ID NOS: 436

<210> SEQ ID NO 1
<211> LENGTH: 21
<212> TYPE: PRT
<213> ORGANISM: Artificial Sequence
<220> FEATURE:
<223> OTHER INFORMATION: Synthetic

<400> SEQUENCE: 1

Ala Glu Gly Asp Asp Pro Ala Lys Ala Ala Phe Asn Ser Leu Gln Ala
1               5                   10                  15

Ser Ala Thr Glu Tyr
            20

<210> SEQ ID NO 2
<211> LENGTH: 29
<212> TYPE: PRT
<213> ORGANISM: Artificial Sequence
<220> FEATURE:
<223> OTHER INFORMATION: Synthetic

<400> SEQUENCE: 2

Ala Thr Ser Leu Pro Ala Phe Ala Gly Val Ile Asp Thr Ser Ala Val
1               5                   10                  15

Glu Ser Ala Ile Thr Asp Gly Gln Gly Asp Met Lys Ala
            20                  25

<210> SEQ ID NO 3
<211> LENGTH: 21
<212> TYPE: PRT
<213> ORGANISM: Artificial Sequence
<220> FEATURE:
<223> OTHER INFORMATION: Synthetic

<400> SEQUENCE: 3

Ala Glu Gly Asp Asp Pro Ala Lys Ala Ala Phe Asp Ser Leu Gln Ala
1               5                   10                  15

Ser Ala Thr Glu Tyr
            20

<210> SEQ ID NO 4
<211> LENGTH: 18
<212> TYPE: PRT
<213> ORGANISM: Artificial Sequence
<220> FEATURE:
<223> OTHER INFORMATION: Synthetic

<400> SEQUENCE: 4

Met Gln Ser Val Ile Thr Asp Val Thr Gly Gln Leu Thr Ala Val Gln
1               5                   10                  15

Ala Asp

<210> SEQ ID NO 5
<211> LENGTH: 25
<212> TYPE: PRT
<213> ORGANISM: Artificial Sequence
<220> FEATURE:
<223> OTHER INFORMATION: Synthetic

<400> SEQUENCE: 5

Ala Glu Pro Asn Ala Ala Thr Asn Tyr Ala Thr Glu Ala Met Asp Ser
1               5                   10                  15

Leu Lys Thr Gln Ala Ile Asp Leu Ile 20                  25

<210> SEQ ID NO 6
<211> LENGTH: 22
<212> TYPE: PRT
<213> ORGANISM: Artificial Sequence
<220> FEATURE:
<223> OTHER INFORMATION: Synthetic

<400> SEQUENCE: 6

Ala Asp Asp Ala Thr Ser Gln Ala Lys Ala Ala Phe Asp Ser Leu Thr
1               5                   10                  15

Ala Gln Ala Thr Glu Met
            20

<210> SEQ ID NO 7
<211> LENGTH: 19
<212> TYPE: PRT
<213> ORGANISM: Artificial Sequence
<220> FEATURE:
<223> OTHER INFORMATION: Synthetic

<400> SEQUENCE: 7

Ser Gly Val Gly Asp Gly Val Asp Val Val Ser Ala Ile Glu Gly Ala
1               5                   10                  15

Ala Gly Pro

<210> SEQ ID NO 8
<211> LENGTH: 17
<212> TYPE: PRT
<213> ORGANISM: Artificial Sequence
<220> FEATURE:
<223> OTHER INFORMATION: Synthetic

<400> SEQUENCE: 8

Met Asp Phe Asn Pro Ser Glu Val Ala Ser Gln Val Thr Asn Tyr Ile
1               5                   10                  15

Gln

<210> SEQ ID NO 9
<211> LENGTH: 29
<212> TYPE: PRT
<213> ORGANISM: Artificial Sequence
<220> FEATURE:
<223> OTHER INFORMATION: Synthetic

<400> SEQUENCE: 9

Ala Asp Asp Gly Thr Ser Thr Ala Thr Ser Tyr Ala Thr Glu Ala Met
1               5                   10                  15

Asn Ser Leu Lys Thr Gln Ala Thr Asp Leu Ile Asp Gln
            20                  25

<210> SEQ ID NO 10
<211> LENGTH: 12
<212> TYPE: PRT
<213> ORGANISM: Artificial Sequence
<220> FEATURE:
<223> OTHER INFORMATION: Synthetic

<400> SEQUENCE: 10

Met Gly Asp Ile Leu Thr Gly Val Ser Gly Ala Glu
1               5                   10

<210> SEQ ID NO 11

<211> LENGTH: 73
<212> TYPE: PRT
<213> ORGANISM: Artificial Sequence
<220> FEATURE:
<223> OTHER INFORMATION: Synthetic

<400> SEQUENCE: 11

Met Lys Lys Ser Leu Val Leu Lys Ala Ser Val Ala Val Ala Thr Leu
1               5                   10                  15

Val Pro Met Leu Ser Phe Ala Ala Glu Gly Asp Asp Pro Ala Lys Ala
            20                  25                  30

Ala Phe Asn Ser Leu Gln Ala Ser Ala Thr Glu Tyr Ile Gly Tyr Ala
        35                  40                  45

Trp Ala Met Val Val Val Ile Val Gly Ala Thr Ile Gly Ile Lys Leu
    50                  55                  60

Phe Lys Lys Phe Thr Ser Lys Ala Ser
65                  70

<210> SEQ ID NO 12
<211> LENGTH: 82
<212> TYPE: PRT
<213> ORGANISM: Artificial Sequence
<220> FEATURE:
<223> OTHER INFORMATION: Synthetic

<400> SEQUENCE: 12

Met Lys Ala Met Lys Gln Arg Ile Ala Lys Phe Ser Pro Val Ala Ser
1               5                   10                  15

Phe Arg Asn Leu Cys Ile Ala Gly Ser Val Thr Ala Ala Thr Ser Leu
            20                  25                  30

Pro Ala Phe Ala Gly Val Ile Asp Thr Ser Ala Val Glu Ser Ala Ile
        35                  40                  45

Thr Asp Gly Gln Gly Asp Met Lys Ala Ile Gly Gly Tyr Ile Val Gly
    50                  55                  60

Ala Leu Val Ile Leu Ala Val Ala Gly Leu Ile Tyr Ser Met Leu Arg
65                  70                  75                  80

Lys Ala

<210> SEQ ID NO 13
<211> LENGTH: 73
<212> TYPE: PRT
<213> ORGANISM: Artificial Sequence
<220> FEATURE:
<223> OTHER INFORMATION: Synthetic

<400> SEQUENCE: 13

Met Lys Lys Ser Leu Val Leu Lys Ala Ser Val Ala Val Ala Thr Leu
1               5                   10                  15

Val Pro Met Leu Ser Phe Ala Ala Glu Gly Asp Asp Pro Ala Lys Ala
            20                  25                  30

Ala Phe Asp Ser Leu Gln Ala Ser Ala Thr Glu Tyr Ile Gly Tyr Ala
        35                  40                  45

Trp Ala Met Val Val Val Ile Val Gly Ala Thr Ile Gly Ile Lys Leu
    50                  55                  60

Phe Lys Lys Phe Thr Ser Lys Ala Ser
65                  70

<210> SEQ ID NO 14
<211> LENGTH: 44
<212> TYPE: PRT

<213> ORGANISM: Artificial Sequence
<220> FEATURE:
<223> OTHER INFORMATION: Synthetic

<400> SEQUENCE: 14

```
Met Gln Ser Val Ile Thr Asp Val Thr Gly Gln Leu Thr Ala Val Gln
1               5                   10                  15

Ala Asp Ile Thr Thr Ile Gly Gly Ala Ile Ile Val Leu Ala Ala Val
            20                  25                  30

Val Leu Gly Ile Arg Trp Ile Lys Ala Gln Phe Phe
        35                  40
```

<210> SEQ ID NO 15
<211> LENGTH: 82
<212> TYPE: PRT
<213> ORGANISM: Artificial Sequence
<220> FEATURE:
<223> OTHER INFORMATION: Synthetic

<400> SEQUENCE: 15

```
Met Arg Val Leu Ser Thr Val Leu Ala Ala Lys Asn Lys Ile Ala Leu
1               5                   10                  15

Gly Ala Ala Thr Met Leu Val Ser Ala Gly Ser Phe Ala Ala Glu Pro
            20                  25                  30

Asn Ala Ala Thr Asn Tyr Ala Thr Glu Ala Met Asp Ser Leu Lys Thr
            35                  40                  45

Gln Ala Ile Asp Leu Ile Ser Gln Thr Trp Pro Val Val Thr Thr Val
        50                  55                  60

Val Val Ala Gly Leu Val Ile Arg Leu Phe Lys Lys Phe Ser Ser Lys
65                  70                  75                  80

Ala Val
```

<210> SEQ ID NO 16
<211> LENGTH: 74
<212> TYPE: PRT
<213> ORGANISM: Artificial Sequence
<220> FEATURE:
<223> OTHER INFORMATION: Synthetic

<400> SEQUENCE: 16

```
Met Lys Lys Ser Val Val Ala Lys Ile Ile Ala Gly Ser Thr Leu Val
1               5                   10                  15

Ile Gly Ser Ser Ala Phe Ala Ala Asp Asp Ala Thr Ser Gln Ala Lys
            20                  25                  30

Ala Ala Phe Asp Ser Leu Thr Ala Gln Ala Thr Glu Met Ser Gly Tyr
            35                  40                  45

Ala Trp Ala Leu Val Val Leu Val Val Gly Ala Thr Val Gly Ile Lys
        50                  55                  60

Leu Phe Lys Lys Phe Val Ser Arg Ala Ser
65                  70
```

<210> SEQ ID NO 17
<211> LENGTH: 44
<212> TYPE: PRT
<213> ORGANISM: Artificial Sequence
<220> FEATURE:
<223> OTHER INFORMATION: Synthetic

<400> SEQUENCE: 17

```
Ser Gly Val Gly Asp Gly Val Asp Val Val Ser Ala Ile Glu Gly Ala
1               5                   10                  15
```

```
Ala Gly Pro Ile Ala Ala Ile Gly Gly Ala Val Leu Thr Val Met Val
             20                  25                  30

Gly Ile Lys Val Tyr Lys Trp Val Arg Arg Ala Met
             35                  40

<210> SEQ ID NO 18
<211> LENGTH: 46
<212> TYPE: PRT
<213> ORGANISM: Artificial Sequence
<220> FEATURE:
<223> OTHER INFORMATION: Synthetic

<400> SEQUENCE: 18

Met Asp Phe Asn Pro Ser Glu Val Ala Ser Gln Val Thr Asn Tyr Ile
1               5                   10                  15

Gln Ala Ile Ala Ala Ala Gly Val Gly Val Leu Ala Leu Ala Ile Gly
             20                  25                  30

Leu Ser Ala Ala Trp Lys Tyr Ala Lys Arg Phe Leu Lys Gly
             35                  40                  45

<210> SEQ ID NO 19
<211> LENGTH: 84
<212> TYPE: PRT
<213> ORGANISM: Artificial Sequence
<220> FEATURE:
<223> OTHER INFORMATION: Synthetic

<400> SEQUENCE: 19

Met Ser Val Ile Thr Lys Val Ala Ala Ala Lys Asn Lys Ile Val Val
1               5                   10                  15

Gly Ala Gly Leu Leu Met Ala Ser Ala Gly Ala Phe Ala Ala Asp Asp
             20                  25                  30

Gly Thr Ser Thr Ala Thr Ser Tyr Ala Thr Glu Ala Met Asn Ser Leu
             35                  40                  45

Lys Thr Gln Ala Thr Asp Leu Ile Asp Gln Thr Trp Pro Val Val Thr
         50                  55                  60

Ser Val Ala Val Ala Gly Leu Ala Ile Arg Leu Phe Lys Lys Phe Ser
65                  70                  75                  80

Ser Lys Ala Val

<210> SEQ ID NO 20
<211> LENGTH: 42
<212> TYPE: PRT
<213> ORGANISM: Artificial Sequence
<220> FEATURE:
<223> OTHER INFORMATION: Synthetic

<400> SEQUENCE: 20

Met Gly Asp Ile Leu Thr Gly Val Ser Gly Ala Glu Ala Ala Thr Ala
1               5                   10                  15

Met Ile Ala Ala Ala Ile Ile Ala Leu Val Gly Phe Thr Lys Trp
             20                  25                  30

Gly Ala Lys Lys Val Ala Ser Phe Phe Gly
             35                  40

<210> SEQ ID NO 21
<211> LENGTH: 39
<212> TYPE: PRT
<213> ORGANISM: Artificial Sequence
<220> FEATURE:
<223> OTHER INFORMATION: Synthetic
```

<400> SEQUENCE: 21

Ser Lys Gly Asn Asp Gln Val Phe Thr Arg Arg Ala Phe Thr Met His
1               5                   10                  15

Pro Tyr Gly Val Lys Phe Lys Asn Ala Val Arg Asp Ala Asn Glu Ile
            20                  25                  30

Thr Pro Thr Asn Ala Asp Leu
            35

<210> SEQ ID NO 22
<211> LENGTH: 333
<212> TYPE: PRT
<213> ORGANISM: Artificial Sequence
<220> FEATURE:
<223> OTHER INFORMATION: Synthetic

<400> SEQUENCE: 22

Met Ala Asn Glu Ile Thr Lys Leu Leu Asp Val Val Thr Pro Glu Val
1               5                   10                  15

Phe Asn Ala Tyr Met Asp Asn Phe Thr Ser Glu Lys Ser Ala Ile Ile
            20                  25                  30

Gln Ser Gly Ile Ala Val Ala Asp Pro Ser Val Ala Gln Asn Ile Thr
        35                  40                  45

Ala Gly Gly Leu Leu Val Asn Met Pro Phe Trp Asn Asp Leu Asp Gly
    50                  55                  60

Glu Asp Glu Thr Leu Gly Asp Gly Glu Lys Gly Leu Glu Thr Gly Lys
65                  70                  75                  80

Ile Thr Ala Ser Ala Asp Ile Ala Ala Val Met Tyr Arg Gly Arg Gly
                85                  90                  95

Trp Ser Val Asn Glu Leu Ala Ala Val Ile Ser Gly Asp Pro Leu
            100                 105                 110

Asp Ala Leu Met Gly Lys Ile Ala Ser Trp Trp Met Arg Arg Glu Gln
            115                 120                 125

Thr Val Leu Ile Ser Val Leu Asn Gly Leu Phe Ala Lys Asn Gly Ala
130                 135                 140

Leu Ala Ser Ser His Leu Leu Ser Lys Pro Thr Ser Ala Ile Ser Gly
145                 150                 155                 160

Asn Leu Val Leu Asp Ala Lys Gln Leu Leu Gly Asp Ser Ser Asp Arg
                165                 170                 175

Leu Ser Leu Met Val Met His Ser Ala Val Tyr Thr Ala Leu Gln Lys
            180                 185                 190

Gln Asn Leu Ile Ala Phe Ile Pro Asn Ala Arg Gly Glu Val Asn Ile
        195                 200                 205

Pro Thr Tyr Leu Gly Tyr Arg Val Val Val Asp Gly Val Pro Ser
    210                 215                 220

Thr Gly Thr Gly Ala Ala Lys Val Tyr Thr Ser Tyr Leu Phe Ala Thr
225                 230                 235                 240

Gly Ser Ile Gly Arg Asn Ile Gly Asn Pro Ala Lys Leu Thr Thr Phe
                245                 250                 255

Glu Thr Ala Arg Asp Ala Ser Lys Gly Asn Asp Gln Val Phe Thr Arg
            260                 265                 270

Arg Ala Phe Thr Met His Pro Tyr Gly Val Lys Phe Lys Asn Ala Val
        275                 280                 285

Arg Asp Ala Asn Glu Ile Thr Pro Thr Asn Ala Asp Leu Ala Lys Ala
    290                 295                 300

Gly Asn Trp Glu Lys Val Tyr Glu Asp Lys Gln Ile Gly Ile Val Gly
305                 310                 315                 320

Ile Gln His Leu Val Glu Glu Leu Pro Ala Ser Gly Ala
            325                 330

<210> SEQ ID NO 23
<211> LENGTH: 6
<212> TYPE: PRT
<213> ORGANISM: Artificial Sequence
<220> FEATURE:
<223> OTHER INFORMATION: Synthetic

<400> SEQUENCE: 23

Lys Ser Val Lys Glu Leu
1               5

<210> SEQ ID NO 24
<211> LENGTH: 11
<212> TYPE: PRT
<213> ORGANISM: Artificial Sequence
<220> FEATURE:
<223> OTHER INFORMATION: Synthetic

<400> SEQUENCE: 24

Ala Glu Gly Asp Asp Pro Ala Lys Ala Ala Phe
1               5                   10

<210> SEQ ID NO 25
<211> LENGTH: 13
<212> TYPE: PRT
<213> ORGANISM: Artificial Sequence
<220> FEATURE:
<223> OTHER INFORMATION: Synthetic

<400> SEQUENCE: 25

Glu Asn Lys Pro Ile Asp Phe Leu Glu Ala Lys Gly Tyr
1               5                   10

<210> SEQ ID NO 26
<211> LENGTH: 34
<212> TYPE: PRT
<213> ORGANISM: Artificial Sequence
<220> FEATURE:
<223> OTHER INFORMATION: Synthetic

<400> SEQUENCE: 26

Lys Gly Lys Ser Lys Lys Leu Lys Ser Val Lys Glu Leu Leu Gly Ile
1               5                   10                  15

Thr Ile Met Glu Arg Ser Ser Phe Glu Lys Asn Pro Ile Asp Leu Glu
            20                  25                  30

Ala Lys

<210> SEQ ID NO 27
<211> LENGTH: 13
<212> TYPE: PRT
<213> ORGANISM: Artificial Sequence
<220> FEATURE:
<223> OTHER INFORMATION: Synthetic

<400> SEQUENCE: 27

Glu Lys Asn Pro Ile Asp Phe Leu Glu Ala Lys Gly Tyr
1               5                   10

<210> SEQ ID NO 28
<211> LENGTH: 10

```
<212> TYPE: PRT
<213> ORGANISM: Artificial Sequence
<220> FEATURE:
<223> OTHER INFORMATION: Synthetic

<400> SEQUENCE: 28

Phe Asp Thr Thr Ile Asp Arg Lys Arg Tyr
1               5                   10

<210> SEQ ID NO 29
<211> LENGTH: 9
<212> TYPE: PRT
<213> ORGANISM: Artificial Sequence
<220> FEATURE:
<223> OTHER INFORMATION: Synthetic

<400> SEQUENCE: 29

Val Arg Gln Gln Leu Pro Glu Lys Tyr
1               5

<210> SEQ ID NO 30
<211> LENGTH: 21
<212> TYPE: PRT
<213> ORGANISM: Artificial Sequence
<220> FEATURE:
<223> OTHER INFORMATION: Synthetic

<400> SEQUENCE: 30

Ala Ala Ala Ala Ala Pro Ala Lys Ala Ala Phe Asp Ser Leu Gln Ala
1               5                   10                  15

Ser Ala Thr Glu Tyr
            20

<210> SEQ ID NO 31
<211> LENGTH: 21
<212> TYPE: PRT
<213> ORGANISM: Artificial Sequence
<220> FEATURE:
<223> OTHER INFORMATION: Synthetic

<400> SEQUENCE: 31

Ala Glu Gly Asp Asp Ala Ala Ala Ala Phe Asp Ser Leu Gln Ala
1               5                   10                  15

Ser Ala Thr Glu Tyr
            20

<210> SEQ ID NO 32
<211> LENGTH: 21
<212> TYPE: PRT
<213> ORGANISM: Artificial Sequence
<220> FEATURE:
<223> OTHER INFORMATION: Synthetic

<400> SEQUENCE: 32

Ala Glu Gly Asp Asp Pro Ala Lys Ala Ala Ala Ala Ala Ala
1               5                   10                  15

Ser Ala Thr Glu Tyr
            20

<210> SEQ ID NO 33
<211> LENGTH: 21
<212> TYPE: PRT
<213> ORGANISM: Artificial Sequence
<220> FEATURE:
<223> OTHER INFORMATION: Synthetic
```

-continued

```
<400> SEQUENCE: 33

Ala Glu Gly Asp Asp Pro Ala Lys Ala Ala Phe Asp Ser Leu Gln Ala
1               5                   10                  15

Ala Ala Ala Ala Ala
            20

<210> SEQ ID NO 34
<211> LENGTH: 6
<212> TYPE: PRT
<213> ORGANISM: Artificial Sequence
<220> FEATURE:
<223> OTHER INFORMATION: Synthetic

<400> SEQUENCE: 34

Glu Lys Asn Pro Ile Asp
1               5

<210> SEQ ID NO 35
<211> LENGTH: 34
<212> TYPE: PRT
<213> ORGANISM: Artificial Sequence
<220> FEATURE:
<223> OTHER INFORMATION: Synthetic

<400> SEQUENCE: 35

Lys Gly Lys Ser Lys Lys Leu Ala Ala Ala Ala Ala Ala Leu Gly Ile
1               5                   10                  15

Thr Ile Met Glu Arg Ser Ser Phe Glu Lys Asn Pro Ile Asp Leu Glu
            20                  25                  30

Ala Lys

<210> SEQ ID NO 36
<211> LENGTH: 34
<212> TYPE: PRT
<213> ORGANISM: Artificial Sequence
<220> FEATURE:
<223> OTHER INFORMATION: Synthetic

<400> SEQUENCE: 36

Lys Gly Lys Ser Lys Lys Leu Lys Ser Val Lys Glu Leu Leu Gly Ile
1               5                   10                  15

Thr Ile Met Glu Arg Ser Ser Phe Ala Ala Ala Ala Ala Ala Leu Glu
            20                  25                  30

Ala Lys

<210> SEQ ID NO 37
<211> LENGTH: 7
<212> TYPE: PRT
<213> ORGANISM: Artificial Sequence
<220> FEATURE:
<223> OTHER INFORMATION: Synthetic

<400> SEQUENCE: 37

Gly Thr Ala Thr Ala Thr Ser
1               5

<210> SEQ ID NO 38
<211> LENGTH: 7
<212> TYPE: PRT
<213> ORGANISM: Artificial Sequence
<220> FEATURE:
<223> OTHER INFORMATION: Synthetic

<400> SEQUENCE: 38
```

Met Asp Phe Asp Pro Ser Glu
1               5

<210> SEQ ID NO 39
<211> LENGTH: 8
<212> TYPE: PRT
<213> ORGANISM: Artificial Sequence
<220> FEATURE:
<223> OTHER INFORMATION: Synthetic

<400> SEQUENCE: 39

Met Asp Phe Asn Pro Ser Glu Val
1               5

<210> SEQ ID NO 40
<211> LENGTH: 8
<212> TYPE: PRT
<213> ORGANISM: Artificial Sequence
<220> FEATURE:
<223> OTHER INFORMATION: Synthetic

<400> SEQUENCE: 40

Met Glu Phe Asn Pro Ser Asp Val
1               5

<210> SEQ ID NO 41
<211> LENGTH: 8
<212> TYPE: PRT
<213> ORGANISM: Artificial Sequence
<220> FEATURE:
<223> OTHER INFORMATION: Synthetic

<400> SEQUENCE: 41

Pro Ser Glu Val Ala Ser Gln Val
1               5

<210> SEQ ID NO 42
<211> LENGTH: 8
<212> TYPE: PRT
<213> ORGANISM: Artificial Sequence
<220> FEATURE:
<223> OTHER INFORMATION: Synthetic

<400> SEQUENCE: 42

Ser Gln Val Thr Asn Tyr Ile Gln
1               5

<210> SEQ ID NO 43
<211> LENGTH: 9
<212> TYPE: PRT
<213> ORGANISM: Artificial Sequence
<220> FEATURE:
<223> OTHER INFORMATION: Synthetic

<400> SEQUENCE: 43

Ala Ser Gln Val Thr Asp Tyr Ile Gln
1               5

<210> SEQ ID NO 44
<211> LENGTH: 9
<212> TYPE: PRT
<213> ORGANISM: Artificial Sequence
<220> FEATURE:
<223> OTHER INFORMATION: Synthetic

<400> SEQUENCE: 44

```
Asp Phe Asn Pro Ser Ala Val Ala Ser
1               5
```

<210> SEQ ID NO 45
<211> LENGTH: 9
<212> TYPE: PRT
<213> ORGANISM: Artificial Sequence
<220> FEATURE:
<223> OTHER INFORMATION: Synthetic

<400> SEQUENCE: 45

```
Phe Asn Pro Ser Asp Val Ala Pro Gln
1               5
```

<210> SEQ ID NO 46
<211> LENGTH: 9
<212> TYPE: PRT
<213> ORGANISM: Artificial Sequence
<220> FEATURE:
<223> OTHER INFORMATION: Synthetic

<400> SEQUENCE: 46

```
Phe Asp Pro Ser Glu Val Ala Pro Gln
1               5
```

<210> SEQ ID NO 47
<211> LENGTH: 9
<212> TYPE: PRT
<213> ORGANISM: Artificial Sequence
<220> FEATURE:
<223> OTHER INFORMATION: Synthetic

<400> SEQUENCE: 47

```
Met Asp Phe Asp Pro Ser Glu Val Ala
1               5
```

<210> SEQ ID NO 48
<211> LENGTH: 9
<212> TYPE: PRT
<213> ORGANISM: Artificial Sequence
<220> FEATURE:
<223> OTHER INFORMATION: Synthetic

<400> SEQUENCE: 48

```
Met Asp Phe Glu Pro Ser Glu Val Ala
1               5
```

<210> SEQ ID NO 49
<211> LENGTH: 9
<212> TYPE: PRT
<213> ORGANISM: Artificial Sequence
<220> FEATURE:
<223> OTHER INFORMATION: Synthetic

<400> SEQUENCE: 49

```
Asn Pro Ala Glu Val Ala Ser Gln Val
1               5
```

<210> SEQ ID NO 50
<211> LENGTH: 9
<212> TYPE: PRT
<213> ORGANISM: Artificial Sequence
<220> FEATURE:
<223> OTHER INFORMATION: Synthetic

<400> SEQUENCE: 50

```
Pro Ser Glu Val Ala Ser Gln Val Thr
```

```
1               5

<210> SEQ ID NO 51
<211> LENGTH: 9
<212> TYPE: PRT
<213> ORGANISM: Artificial Sequence
<220> FEATURE:
<223> OTHER INFORMATION: Synthetic

<400> SEQUENCE: 51

Thr Gln Ala Thr Asp Leu Leu Asp Gln
1               5

<210> SEQ ID NO 52
<211> LENGTH: 10
<212> TYPE: PRT
<213> ORGANISM: Artificial Sequence
<220> FEATURE:
<223> OTHER INFORMATION: Synthetic

<400> SEQUENCE: 52

Asp Phe Asn Pro Thr Asp Val Ala Ser Gln
1               5                   10

<210> SEQ ID NO 53
<211> LENGTH: 10
<212> TYPE: PRT
<213> ORGANISM: Artificial Sequence
<220> FEATURE:
<223> OTHER INFORMATION: Synthetic

<400> SEQUENCE: 53

Asp Phe Asn Tyr Pro Ser Glu Val Ala Ser
1               5                   10

<210> SEQ ID NO 54
<211> LENGTH: 10
<212> TYPE: PRT
<213> ORGANISM: Artificial Sequence
<220> FEATURE:
<223> OTHER INFORMATION: Synthetic

<400> SEQUENCE: 54

Asp Thr Ser Ala Ile Glu Ala Ala Ile Thr
1               5                   10

<210> SEQ ID NO 55
<211> LENGTH: 10
<212> TYPE: PRT
<213> ORGANISM: Artificial Sequence
<220> FEATURE:
<223> OTHER INFORMATION: Synthetic

<400> SEQUENCE: 55

Glu Ala Ala Ser Gln Val Thr Asn Tyr Ile
1               5                   10

<210> SEQ ID NO 56
<211> LENGTH: 10
<212> TYPE: PRT
<213> ORGANISM: Artificial Sequence
<220> FEATURE:
<223> OTHER INFORMATION: Synthetic

<400> SEQUENCE: 56

Met Asp Ile Asn Pro Ser Asp Ile Ala Ser
1               5                   10
```

```
<210> SEQ ID NO 57
<211> LENGTH: 10
<212> TYPE: PRT
<213> ORGANISM: Artificial Sequence
<220> FEATURE:
<223> OTHER INFORMATION: Synthetic

<400> SEQUENCE: 57

Met Asn Ala Leu Lys Thr Thr Asp Leu Ile
1               5                   10

<210> SEQ ID NO 58
<211> LENGTH: 10
<212> TYPE: PRT
<213> ORGANISM: Artificial Sequence
<220> FEATURE:
<223> OTHER INFORMATION: Synthetic

<400> SEQUENCE: 58

Asn Pro Ser Glu Val Ala Pro Gln Val Thr
1               5                   10

<210> SEQ ID NO 59
<211> LENGTH: 10
<212> TYPE: PRT
<213> ORGANISM: Artificial Sequence
<220> FEATURE:
<223> OTHER INFORMATION: Synthetic

<400> SEQUENCE: 59

Pro Ala Phe Ala Gly Val Ile Asp Thr Ser
1               5                   10

<210> SEQ ID NO 60
<211> LENGTH: 10
<212> TYPE: PRT
<213> ORGANISM: Artificial Sequence
<220> FEATURE:
<223> OTHER INFORMATION: Synthetic

<400> SEQUENCE: 60

Ser Ala Ala Ser Ser Tyr Ala Ala Glu Ala
1               5                   10

<210> SEQ ID NO 61
<211> LENGTH: 10
<212> TYPE: PRT
<213> ORGANISM: Artificial Sequence
<220> FEATURE:
<223> OTHER INFORMATION: Synthetic

<400> SEQUENCE: 61

Ser Ala Ala Asp Ser Tyr Asp Ala Asp Ala
1               5                   10

<210> SEQ ID NO 62
<211> LENGTH: 11
<212> TYPE: PRT
<213> ORGANISM: Artificial Sequence
<220> FEATURE:
<223> OTHER INFORMATION: Synthetic

<400> SEQUENCE: 62

Ala Leu Thr Glu Ala Gln Gly Asp Met Lys Ala
1               5                   10
```

```
<210> SEQ ID NO 63
<211> LENGTH: 11
<212> TYPE: PRT
<213> ORGANISM: Artificial Sequence
<220> FEATURE:
<223> OTHER INFORMATION: Synthetic

<400> SEQUENCE: 63

Asp Asp Gly Thr Ala Thr Ala Thr Ser Tyr Ala
1               5                   10

<210> SEQ ID NO 64
<211> LENGTH: 11
<212> TYPE: PRT
<213> ORGANISM: Artificial Sequence
<220> FEATURE:
<223> OTHER INFORMATION: Synthetic

<400> SEQUENCE: 64

Asp Ser Leu Lys Thr Gln Ala Ile Asp Leu Ile
1               5                   10

<210> SEQ ID NO 65
<211> LENGTH: 11
<212> TYPE: PRT
<213> ORGANISM: Artificial Sequence
<220> FEATURE:
<223> OTHER INFORMATION: Synthetic

<400> SEQUENCE: 65

Glu Asp Glu Ala Lys Ala Ala Phe Glu Ala Leu
1               5                   10

<210> SEQ ID NO 66
<211> LENGTH: 11
<212> TYPE: PRT
<213> ORGANISM: Artificial Sequence
<220> FEATURE:
<223> OTHER INFORMATION: Synthetic

<400> SEQUENCE: 66

Glu Val Ala Ala Gln Val Thr Asp Tyr Leu Gln
1               5                   10

<210> SEQ ID NO 67
<211> LENGTH: 11
<212> TYPE: PRT
<213> ORGANISM: Artificial Sequence
<220> FEATURE:
<223> OTHER INFORMATION: Synthetic

<400> SEQUENCE: 67

Glu Val Val Ser Asp Leu Thr Asn Tyr Ile Gln
1               5                   10

<210> SEQ ID NO 68
<211> LENGTH: 11
<212> TYPE: PRT
<213> ORGANISM: Artificial Sequence
<220> FEATURE:
<223> OTHER INFORMATION: Synthetic

<400> SEQUENCE: 68

Phe Asn Pro Ser Glu Ile Pro Ser Gln Ile Thr
1               5                   10
```

```
<210> SEQ ID NO 69
<211> LENGTH: 11
<212> TYPE: PRT
<213> ORGANISM: Artificial Sequence
<220> FEATURE:
<223> OTHER INFORMATION: Synthetic

<400> SEQUENCE: 69

Gly Thr Pro Thr Ala Thr Ser Tyr Ala Thr Glu
1               5                   10

<210> SEQ ID NO 70
<211> LENGTH: 11
<212> TYPE: PRT
<213> ORGANISM: Artificial Sequence
<220> FEATURE:
<223> OTHER INFORMATION: Synthetic

<400> SEQUENCE: 70

Gly Thr Ser Ala Ala Thr Ser Tyr Asp Thr Glu
1               5                   10

<210> SEQ ID NO 71
<211> LENGTH: 11
<212> TYPE: PRT
<213> ORGANISM: Artificial Sequence
<220> FEATURE:
<223> OTHER INFORMATION: Synthetic

<400> SEQUENCE: 71

Met Asp Phe Asp Pro Ser Glu Leu Ala Tyr Ile
1               5                   10

<210> SEQ ID NO 72
<211> LENGTH: 11
<212> TYPE: PRT
<213> ORGANISM: Artificial Sequence
<220> FEATURE:
<223> OTHER INFORMATION: Synthetic

<400> SEQUENCE: 72

Met Asp Phe Asn Pro Glu Met Ala Ser Ser Val
1               5                   10

<210> SEQ ID NO 73
<211> LENGTH: 11
<212> TYPE: PRT
<213> ORGANISM: Artificial Sequence
<220> FEATURE:
<223> OTHER INFORMATION: Synthetic

<400> SEQUENCE: 73

Met Asp Phe Asn Pro Ser Asp Ile Ala Tyr Ile
1               5                   10

<210> SEQ ID NO 74
<211> LENGTH: 11
<212> TYPE: PRT
<213> ORGANISM: Artificial Sequence
<220> FEATURE:
<223> OTHER INFORMATION: Synthetic

<400> SEQUENCE: 74

Met Asn Ser Leu Lys Asn His Thr Asp Leu Ile
1               5                   10

<210> SEQ ID NO 75
```

```
<211> LENGTH: 11
<212> TYPE: PRT
<213> ORGANISM: Artificial Sequence
<220> FEATURE:
<223> OTHER INFORMATION: Synthetic

<400> SEQUENCE: 75

Met Ser Phe Asn Pro Glu Val Ala Ser Gln Val
1               5                   10

<210> SEQ ID NO 76
<211> LENGTH: 11
<212> TYPE: PRT
<213> ORGANISM: Artificial Sequence
<220> FEATURE:
<223> OTHER INFORMATION: Synthetic

<400> SEQUENCE: 76

Asn Asp Gly Thr Ser Thr Ala Thr Ser Ala Thr
1               5                   10

<210> SEQ ID NO 77
<211> LENGTH: 11
<212> TYPE: PRT
<213> ORGANISM: Artificial Sequence
<220> FEATURE:
<223> OTHER INFORMATION: Synthetic

<400> SEQUENCE: 77

Asn Phe Asn Pro Gln Val Thr Asn Tyr Ile Glu
1               5                   10

<210> SEQ ID NO 78
<211> LENGTH: 11
<212> TYPE: PRT
<213> ORGANISM: Artificial Sequence
<220> FEATURE:
<223> OTHER INFORMATION: Synthetic

<400> SEQUENCE: 78

Asn Pro Ser Glu Val Ala Ser Gln Ile Ile Gln
1               5                   10

<210> SEQ ID NO 79
<211> LENGTH: 11
<212> TYPE: PRT
<213> ORGANISM: Artificial Sequence
<220> FEATURE:
<223> OTHER INFORMATION: Synthetic

<400> SEQUENCE: 79

Pro Ser Ala Val Gln Val Thr Asn Tyr Ile Gln
1               5                   10

<210> SEQ ID NO 80
<211> LENGTH: 11
<212> TYPE: PRT
<213> ORGANISM: Artificial Sequence
<220> FEATURE:
<223> OTHER INFORMATION: Synthetic

<400> SEQUENCE: 80

Ser Glu Val Gly Gly Asn Met Thr Ser Tyr Ile
1               5                   10

<210> SEQ ID NO 81
<211> LENGTH: 11
```

```
<212> TYPE: PRT
<213> ORGANISM: Artificial Sequence
<220> FEATURE:
<223> OTHER INFORMATION: Synthetic

<400> SEQUENCE: 81

Ser Gln Val Ala Ser Gln Val Thr Asp Tyr Ile
1               5                   10

<210> SEQ ID NO 82
<211> LENGTH: 11
<212> TYPE: PRT
<213> ORGANISM: Artificial Sequence
<220> FEATURE:
<223> OTHER INFORMATION: Synthetic

<400> SEQUENCE: 82

Thr Glu Ile Met Gly Ser Leu Lys Thr Gln Ala
1               5                   10

<210> SEQ ID NO 83
<211> LENGTH: 12
<212> TYPE: PRT
<213> ORGANISM: Artificial Sequence
<220> FEATURE:
<223> OTHER INFORMATION: Synthetic

<400> SEQUENCE: 83

Ala Ala Asp Ser Leu Gln Ala Ser Ala Thr Asp Tyr
1               5                   10

<210> SEQ ID NO 84
<211> LENGTH: 12
<212> TYPE: PRT
<213> ORGANISM: Artificial Sequence
<220> FEATURE:
<223> OTHER INFORMATION: Synthetic

<400> SEQUENCE: 84

Ala Met Asn Ser Leu Lys Glu Asn Asp Leu Ile Asp
1               5                   10

<210> SEQ ID NO 85
<211> LENGTH: 12
<212> TYPE: PRT
<213> ORGANISM: Artificial Sequence
<220> FEATURE:
<223> OTHER INFORMATION: Synthetic

<400> SEQUENCE: 85

Asp Asp Ala Ser Ser Asn Ala Thr Ser Tyr Ala Thr
1               5                   10

<210> SEQ ID NO 86
<211> LENGTH: 12
<212> TYPE: PRT
<213> ORGANISM: Artificial Sequence
<220> FEATURE:
<223> OTHER INFORMATION: Synthetic

<400> SEQUENCE: 86

Asp Asp Gly Thr Ala Asn Ala Thr Ser Tyr Ala Thr
1               5                   10

<210> SEQ ID NO 87
<211> LENGTH: 12
<212> TYPE: PRT
```

```
<213> ORGANISM: Artificial Sequence
<220> FEATURE:
<223> OTHER INFORMATION: Synthetic

<400> SEQUENCE: 87

Asp Phe Asn Leu Ser Glu Val Ala Ala Gln Val Thr
1               5                   10

<210> SEQ ID NO 88
<211> LENGTH: 12
<212> TYPE: PRT
<213> ORGANISM: Artificial Sequence
<220> FEATURE:
<223> OTHER INFORMATION: Synthetic

<400> SEQUENCE: 88

Asp Phe Val Ala Ser Gln Val Thr Asn Tyr Lys Gln
1               5                   10

<210> SEQ ID NO 89
<211> LENGTH: 12
<212> TYPE: PRT
<213> ORGANISM: Artificial Sequence
<220> FEATURE:
<223> OTHER INFORMATION: Synthetic

<400> SEQUENCE: 89

Glu Val Ala Ser Gln Leu Leu Gly Thr Asn Tyr Ile
1               5                   10

<210> SEQ ID NO 90
<211> LENGTH: 12
<212> TYPE: PRT
<213> ORGANISM: Artificial Sequence
<220> FEATURE:
<223> OTHER INFORMATION: Synthetic

<400> SEQUENCE: 90

Phe Asn Pro Pro Thr Val Thr Ser Gln Val Thr Asn
1               5                   10

<210> SEQ ID NO 91
<211> LENGTH: 12
<212> TYPE: PRT
<213> ORGANISM: Artificial Sequence
<220> FEATURE:
<223> OTHER INFORMATION: Synthetic

<400> SEQUENCE: 91

Gly Thr Ser Thr Thr Thr Thr Tyr Thr Asp Ala Met
1               5                   10

<210> SEQ ID NO 92
<211> LENGTH: 12
<212> TYPE: PRT
<213> ORGANISM: Artificial Sequence
<220> FEATURE:
<223> OTHER INFORMATION: Synthetic

<400> SEQUENCE: 92

Ile Asp Thr Ser Leu Ile Glu Ala Ala Ile Thr Asp
1               5                   10

<210> SEQ ID NO 93
<211> LENGTH: 12
<212> TYPE: PRT
<213> ORGANISM: Artificial Sequence
```

```
<220> FEATURE:
<223> OTHER INFORMATION: Synthetic

<400> SEQUENCE: 93

Leu Asp Leu Ser Pro Ser Glu Val Ala Ser Gln Val
1               5                   10

<210> SEQ ID NO 94
<211> LENGTH: 12
<212> TYPE: PRT
<213> ORGANISM: Artificial Sequence
<220> FEATURE:
<223> OTHER INFORMATION: Synthetic

<400> SEQUENCE: 94

Leu Pro Ala Phe Ala Gly Val Ile Asp Val Glu Ser
1               5                   10

<210> SEQ ID NO 95
<211> LENGTH: 12
<212> TYPE: PRT
<213> ORGANISM: Artificial Sequence
<220> FEATURE:
<223> OTHER INFORMATION: Synthetic

<400> SEQUENCE: 95

Met Asp Glu Ile Ser Gln Ile Thr Asp Tyr Ile Gln
1               5                   10

<210> SEQ ID NO 96
<211> LENGTH: 12
<212> TYPE: PRT
<213> ORGANISM: Artificial Sequence
<220> FEATURE:
<223> OTHER INFORMATION: Synthetic

<400> SEQUENCE: 96

Met Asp Phe Thr Pro Ser Glu Val Ala Arg Asn Val
1               5                   10

<210> SEQ ID NO 97
<211> LENGTH: 12
<212> TYPE: PRT
<213> ORGANISM: Artificial Sequence
<220> FEATURE:
<223> OTHER INFORMATION: Synthetic

<400> SEQUENCE: 97

Asn Pro Asn Glu Val Ser Arg Gln Val Asn Tyr Ile
1               5                   10

<210> SEQ ID NO 98
<211> LENGTH: 12
<212> TYPE: PRT
<213> ORGANISM: Artificial Sequence
<220> FEATURE:
<223> OTHER INFORMATION: Synthetic

<400> SEQUENCE: 98

Asn Pro Arg Glu Ile Ala Ser Gln Val Ser Asp Tyr
1               5                   10

<210> SEQ ID NO 99
<211> LENGTH: 12
<212> TYPE: PRT
<213> ORGANISM: Artificial Sequence
<220> FEATURE:
```

<223> OTHER INFORMATION: Synthetic

<400> SEQUENCE: 99

Asn Pro Ser Glu Val Ala Ser Gln Ile Ile Gln
1               5                   10

<210> SEQ ID NO 100
<211> LENGTH: 12
<212> TYPE: PRT
<213> ORGANISM: Artificial Sequence
<220> FEATURE:
<223> OTHER INFORMATION: Synthetic

<400> SEQUENCE: 100

Asn Ser Ser Glu Val Ala Ser Gln Val Ala Asn Tyr
1               5                   10

<210> SEQ ID NO 101
<211> LENGTH: 12
<212> TYPE: PRT
<213> ORGANISM: Artificial Sequence
<220> FEATURE:
<223> OTHER INFORMATION: Synthetic

<400> SEQUENCE: 101

Pro Ala Lys Ala Ala Phe Asp Leu Gln Ala Thr Ala
1               5                   10

<210> SEQ ID NO 102
<211> LENGTH: 12
<212> TYPE: PRT
<213> ORGANISM: Artificial Sequence
<220> FEATURE:
<223> OTHER INFORMATION: Synthetic

<400> SEQUENCE: 102

Ser Glu Val Ala Ser Gln Val Gln Asn Phe Ile Gln
1               5                   10

<210> SEQ ID NO 103
<211> LENGTH: 12
<212> TYPE: PRT
<213> ORGANISM: Artificial Sequence
<220> FEATURE:
<223> OTHER INFORMATION: Synthetic

<400> SEQUENCE: 103

Ser Phe Ala Thr Glu Val Met Asn Ser Leu Pro Thr
1               5                   10

<210> SEQ ID NO 104
<211> LENGTH: 12
<212> TYPE: PRT
<213> ORGANISM: Artificial Sequence
<220> FEATURE:
<223> OTHER INFORMATION: Synthetic

<400> SEQUENCE: 104

Ser Tyr Ala Thr Ser Met Asn Asn Leu Lys Lys Gln
1               5                   10

<210> SEQ ID NO 105
<211> LENGTH: 12
<212> TYPE: PRT
<213> ORGANISM: Artificial Sequence
<220> FEATURE:
<223> OTHER INFORMATION: Synthetic

<400> SEQUENCE: 105

Thr Ala Ser Ser Tyr Ala Thr Gln Ala Gln Lys Ser
1               5                   10

<210> SEQ ID NO 106
<211> LENGTH: 12
<212> TYPE: PRT
<213> ORGANISM: Artificial Sequence
<220> FEATURE:
<223> OTHER INFORMATION: Synthetic

<400> SEQUENCE: 106

Met Gly Asp Ile Leu Thr Gly Val Ser Gly Ala Glu
1               5                   10

<210> SEQ ID NO 107
<211> LENGTH: 13
<212> TYPE: PRT
<213> ORGANISM: Artificial Sequence
<220> FEATURE:
<223> OTHER INFORMATION: Synthetic

<400> SEQUENCE: 107

Ala Gly Leu Ile Asp Thr Ala Ser Val Glu Ser Asp Ile
1               5                   10

<210> SEQ ID NO 108
<211> LENGTH: 13
<212> TYPE: PRT
<213> ORGANISM: Artificial Sequence
<220> FEATURE:
<223> OTHER INFORMATION: Synthetic

<400> SEQUENCE: 108

Ala Gly Leu Ile Asp Thr Ser Ser Val Asp Asn Ala Ile
1               5                   10

<210> SEQ ID NO 109
<211> LENGTH: 13
<212> TYPE: PRT
<213> ORGANISM: Artificial Sequence
<220> FEATURE:
<223> OTHER INFORMATION: Synthetic

<400> SEQUENCE: 109

Ala Gly Leu Ile Asp Thr Ser Ser Val Glu Lys Ser Ile
1               5                   10

<210> SEQ ID NO 110
<211> LENGTH: 13
<212> TYPE: PRT
<213> ORGANISM: Artificial Sequence
<220> FEATURE:
<223> OTHER INFORMATION: Synthetic

<400> SEQUENCE: 110

Ala Gly Leu Ile Glu Thr Ser Ser Val Glu Arg Ser Ile
1               5                   10

<210> SEQ ID NO 111
<211> LENGTH: 13
<212> TYPE: PRT
<213> ORGANISM: Artificial Sequence
<220> FEATURE:
<223> OTHER INFORMATION: Synthetic

```
<400> SEQUENCE: 111

Ala Gly Leu Ile Asp Thr Ser Ser Val Glu Ser Ser Ile
1               5                   10

<210> SEQ ID NO 112
<211> LENGTH: 13
<212> TYPE: PRT
<213> ORGANISM: Artificial Sequence
<220> FEATURE:
<223> OTHER INFORMATION: Synthetic

<400> SEQUENCE: 112

Ala Gly Leu Ile Asp Thr Ser Thr Val Asp Ser Thr Ile
1               5                   10

<210> SEQ ID NO 113
<211> LENGTH: 13
<212> TYPE: PRT
<213> ORGANISM: Artificial Sequence
<220> FEATURE:
<223> OTHER INFORMATION: Synthetic

<400> SEQUENCE: 113

Ala Gly Met Ile Asp Ser Ser Ser Val Asp Ser Ala Ile
1               5                   10

<210> SEQ ID NO 114
<211> LENGTH: 13
<212> TYPE: PRT
<213> ORGANISM: Artificial Sequence
<220> FEATURE:
<223> OTHER INFORMATION: Synthetic

<400> SEQUENCE: 114

Ala Gly Met Ile Asp Thr Ser Ser Ile Asp Ser Ser Ile
1               5                   10

<210> SEQ ID NO 115
<211> LENGTH: 13
<212> TYPE: PRT
<213> ORGANISM: Artificial Sequence
<220> FEATURE:
<223> OTHER INFORMATION: Synthetic

<400> SEQUENCE: 115

Asp Asp Gly Thr Thr Thr Ala Tyr Ala Thr Asp Glu Ala
1               5                   10

<210> SEQ ID NO 116
<211> LENGTH: 13
<212> TYPE: PRT
<213> ORGANISM: Artificial Sequence
<220> FEATURE:
<223> OTHER INFORMATION: Synthetic

<400> SEQUENCE: 116

Asp Phe Asp Pro Ser Glu Val Glu Gln Val Val Asn Tyr
1               5                   10

<210> SEQ ID NO 117
<211> LENGTH: 13
<212> TYPE: PRT
<213> ORGANISM: Artificial Sequence
<220> FEATURE:
<223> OTHER INFORMATION: Synthetic

<400> SEQUENCE: 117
```

Asp Phe Asn Pro Ala Glu Val Ala Lys Arg Asn Tyr Ile
1               5                   10

<210> SEQ ID NO 118
<211> LENGTH: 13
<212> TYPE: PRT
<213> ORGANISM: Artificial Sequence
<220> FEATURE:
<223> OTHER INFORMATION: Synthetic

<400> SEQUENCE: 118

Asp Phe Asn Pro Ser Glu Ile Ala Lys Arg Asn Tyr Ile
1               5                   10

<210> SEQ ID NO 119
<211> LENGTH: 13
<212> TYPE: PRT
<213> ORGANISM: Artificial Sequence
<220> FEATURE:
<223> OTHER INFORMATION: Synthetic

<400> SEQUENCE: 119

Asp Phe Ser Pro Ala Glu Val Ala Lys Arg Asn Tyr Ile
1               5                   10

<210> SEQ ID NO 120
<211> LENGTH: 13
<212> TYPE: PRT
<213> ORGANISM: Artificial Sequence
<220> FEATURE:
<223> OTHER INFORMATION: Synthetic

<400> SEQUENCE: 120

Asp Phe Ser Gln Ser Glu Val Asp Gln Gln Val Thr Asn
1               5                   10

<210> SEQ ID NO 121
<211> LENGTH: 13
<212> TYPE: PRT
<213> ORGANISM: Artificial Sequence
<220> FEATURE:
<223> OTHER INFORMATION: Synthetic

<400> SEQUENCE: 121

Asp Ser Gly Thr Ser Ala Ala Thr Ser Tyr Asp Thr Glu
1               5                   10

<210> SEQ ID NO 122
<211> LENGTH: 13
<212> TYPE: PRT
<213> ORGANISM: Artificial Sequence
<220> FEATURE:
<223> OTHER INFORMATION: Synthetic

<400> SEQUENCE: 122

Phe Leu Gly Val Ile Asp Asn Ser Glu Ser Ala Ile Thr
1               5                   10

<210> SEQ ID NO 123
<211> LENGTH: 13
<212> TYPE: PRT
<213> ORGANISM: Artificial Sequence
<220> FEATURE:
<223> OTHER INFORMATION: Synthetic

<400> SEQUENCE: 123

Phe Asn Pro Asn Glu Val Leu Ala Ser Gln Ser Thr Asn
1               5                   10

<210> SEQ ID NO 124
<211> LENGTH: 13
<212> TYPE: PRT
<213> ORGANISM: Artificial Sequence
<220> FEATURE:
<223> OTHER INFORMATION: Synthetic

<400> SEQUENCE: 124

Phe Asn Pro Ser Glu Val Ala Ala Leu Thr Ser Phe Ile
1               5                   10

<210> SEQ ID NO 125
<211> LENGTH: 13
<212> TYPE: PRT
<213> ORGANISM: Artificial Sequence
<220> FEATURE:
<223> OTHER INFORMATION: Synthetic

<400> SEQUENCE: 125

Phe Asn Pro Ser Glu Val Pro Ser Ile Gly Asn Tyr Ile
1               5                   10

<210> SEQ ID NO 126
<211> LENGTH: 13
<212> TYPE: PRT
<213> ORGANISM: Artificial Sequence
<220> FEATURE:
<223> OTHER INFORMATION: Synthetic

<400> SEQUENCE: 126

Met Asp Asp Phe Asn Pro Ala Glu Val Ala Arg Gln Ile
1               5                   10

<210> SEQ ID NO 127
<211> LENGTH: 13
<212> TYPE: PRT
<213> ORGANISM: Artificial Sequence
<220> FEATURE:
<223> OTHER INFORMATION: Synthetic

<400> SEQUENCE: 127

Met Asp Phe Tyr Gln Lys Asn Pro Ser Ala Val Ala Ser
1               5                   10

<210> SEQ ID NO 128
<211> LENGTH: 13
<212> TYPE: PRT
<213> ORGANISM: Artificial Sequence
<220> FEATURE:
<223> OTHER INFORMATION: Synthetic

<400> SEQUENCE: 128

Met Ser Phe Asn Ser Glu Ser Ala Ser Gln Val Thr Asn
1               5                   10

<210> SEQ ID NO 129
<211> LENGTH: 13
<212> TYPE: PRT
<213> ORGANISM: Artificial Sequence
<220> FEATURE:
<223> OTHER INFORMATION: Synthetic

<400> SEQUENCE: 129

Met Ser Phe Ser Pro Ser Glu Ile Ala Ser Glu Ile Gln

```
<210> SEQ ID NO 130
<211> LENGTH: 13
<212> TYPE: PRT
<213> ORGANISM: Artificial Sequence
<220> FEATURE:
<223> OTHER INFORMATION: Synthetic

<400> SEQUENCE: 130

Pro Ser Glu Val Ala Ala Gln Ile Val Asn Tyr Tyr Gln
1               5                   10

<210> SEQ ID NO 131
<211> LENGTH: 13
<212> TYPE: PRT
<213> ORGANISM: Artificial Sequence
<220> FEATURE:
<223> OTHER INFORMATION: Synthetic

<400> SEQUENCE: 131

Ser Ala Val Glu Ser Ala Phe Asn Glu Gly Glu Gly Asp
1               5                   10

<210> SEQ ID NO 132
<211> LENGTH: 13
<212> TYPE: PRT
<213> ORGANISM: Artificial Sequence
<220> FEATURE:
<223> OTHER INFORMATION: Synthetic

<400> SEQUENCE: 132

Thr Ser Tyr Ala Thr Asn Ser Ile Asn Ser Leu Asn Thr
1               5                   10

<210> SEQ ID NO 133
<211> LENGTH: 13
<212> TYPE: PRT
<213> ORGANISM: Artificial Sequence
<220> FEATURE:
<223> OTHER INFORMATION: Synthetic

<400> SEQUENCE: 133

Thr Ser Tyr Ala Thr Ser Ser Ile Asn Ser Leu Asn Thr
1               5                   10

<210> SEQ ID NO 134
<211> LENGTH: 13
<212> TYPE: PRT
<213> ORGANISM: Artificial Sequence
<220> FEATURE:
<223> OTHER INFORMATION: Synthetic

<400> SEQUENCE: 134

Val Leu Asp Thr Ser Glu Val Glu Ser Pro Ile Thr Glu
1               5                   10

<210> SEQ ID NO 135
<211> LENGTH: 14
<212> TYPE: PRT
<213> ORGANISM: Artificial Sequence
<220> FEATURE:
<223> OTHER INFORMATION: Synthetic

<400> SEQUENCE: 135

Ala Asp Glu Gly Thr Thr Ala Thr Thr Tyr Ala Val Asp Ala
1               5                   10
```

<210> SEQ ID NO 136
<211> LENGTH: 14
<212> TYPE: PRT
<213> ORGANISM: Artificial Sequence
<220> FEATURE:
<223> OTHER INFORMATION: Synthetic

<400> SEQUENCE: 136

Ala Glu Asp Gly Thr Thr Ala Thr Thr Tyr Ala Val Glu Ala
1               5                   10

<210> SEQ ID NO 137
<211> LENGTH: 14
<212> TYPE: PRT
<213> ORGANISM: Artificial Sequence
<220> FEATURE:
<223> OTHER INFORMATION: Synthetic

<400> SEQUENCE: 137

Ala Asp Glu Gly Ser Ser Ala Thr Ser Tyr Ala Val Asp Ala
1               5                   10

<210> SEQ ID NO 138
<211> LENGTH: 14
<212> TYPE: PRT
<213> ORGANISM: Artificial Sequence
<220> FEATURE:
<223> OTHER INFORMATION: Synthetic

<400> SEQUENCE: 138

Ala Phe Cys Gly Val Ile Asp Thr Ser Ala Val Ala Ser Ala
1               5                   10

<210> SEQ ID NO 139
<211> LENGTH: 14
<212> TYPE: PRT
<213> ORGANISM: Artificial Sequence
<220> FEATURE:
<223> OTHER INFORMATION: Synthetic

<400> SEQUENCE: 139

Ala Gly Asp Gly Thr Thr Thr Ala Thr Ile Tyr Ala Glu Ala
1               5                   10

<210> SEQ ID NO 140
<211> LENGTH: 14
<212> TYPE: PRT
<213> ORGANISM: Artificial Sequence
<220> FEATURE:
<223> OTHER INFORMATION: Synthetic

<400> SEQUENCE: 140

Ala Gly Glu Gly Thr Ser Thr Ala Thr Val Tyr Ala Glu Ala
1               5                   10

<210> SEQ ID NO 141
<211> LENGTH: 14
<212> TYPE: PRT
<213> ORGANISM: Artificial Sequence
<220> FEATURE:
<223> OTHER INFORMATION: Synthetic

<400> SEQUENCE: 141

Ala Lys Ala Ala Phe Asp Ser Leu Thr Ala Gln Ala Thr Glu
1               5                   10

<210> SEQ ID NO 142
<211> LENGTH: 14
<212> TYPE: PRT
<213> ORGANISM: Artificial Sequence
<220> FEATURE:
<223> OTHER INFORMATION: Synthetic

<400> SEQUENCE: 142

Ala Ser Val Ala Asp Ser Ser Ala Ala Glu Ser Ala Ile Thr
1               5                   10

<210> SEQ ID NO 143
<211> LENGTH: 14
<212> TYPE: PRT
<213> ORGANISM: Artificial Sequence
<220> FEATURE:
<223> OTHER INFORMATION: Synthetic

<400> SEQUENCE: 143

Asp Met Thr Ala Val Asn Ser Ala Ile Thr Ala Gly Gln Gly
1               5                   10

<210> SEQ ID NO 144
<211> LENGTH: 14
<212> TYPE: PRT
<213> ORGANISM: Artificial Sequence
<220> FEATURE:
<223> OTHER INFORMATION: Synthetic

<400> SEQUENCE: 144

Phe Asn Pro Thr Glu Val Val Gln Val Thr Gln Tyr Leu Gln
1               5                   10

<210> SEQ ID NO 145
<211> LENGTH: 14
<212> TYPE: PRT
<213> ORGANISM: Artificial Sequence
<220> FEATURE:
<223> OTHER INFORMATION: Synthetic

<400> SEQUENCE: 145

Phe Ser Pro Glu Val Ile Ser Gln Ile Thr Glu Tyr Ile Gln
1               5                   10

<210> SEQ ID NO 146
<211> LENGTH: 14
<212> TYPE: PRT
<213> ORGANISM: Artificial Sequence
<220> FEATURE:
<223> OTHER INFORMATION: Synthetic

<400> SEQUENCE: 146

Gly Gln Ala Thr Ala Thr Ser Tyr Ala Thr Gln Thr Gln Ala
1               5                   10

<210> SEQ ID NO 147
<211> LENGTH: 14
<212> TYPE: PRT
<213> ORGANISM: Artificial Sequence
<220> FEATURE:
<223> OTHER INFORMATION: Synthetic

<400> SEQUENCE: 147

Gly Val Ile Asp Ala Ser Ala Val Glu Arg Ala Ile Ala Asp
1               5                   10

```
<210> SEQ ID NO 148
<211> LENGTH: 14
<212> TYPE: PRT
<213> ORGANISM: Artificial Sequence
<220> FEATURE:
<223> OTHER INFORMATION: Synthetic

<400> SEQUENCE: 148

Leu Asn Phe Glu Ile Ser Glu Val Ala Ser Gln Val Thr Asn
1               5                   10

<210> SEQ ID NO 149
<211> LENGTH: 14
<212> TYPE: PRT
<213> ORGANISM: Artificial Sequence
<220> FEATURE:
<223> OTHER INFORMATION: Synthetic

<400> SEQUENCE: 149

Met Asp Phe Asn Arg Ser Gly Val Thr Ser Ser Val Thr Asn
1               5                   10

<210> SEQ ID NO 150
<211> LENGTH: 14
<212> TYPE: PRT
<213> ORGANISM: Artificial Sequence
<220> FEATURE:
<223> OTHER INFORMATION: Synthetic

<400> SEQUENCE: 150

Met Asp Ile Asn Ser Ser Glu Val Ala Thr Asp Phe Tyr Ile
1               5                   10

<210> SEQ ID NO 151
<211> LENGTH: 14
<212> TYPE: PRT
<213> ORGANISM: Artificial Sequence
<220> FEATURE:
<223> OTHER INFORMATION: Synthetic

<400> SEQUENCE: 151

Met Gly Phe Asn Pro Ser Ile Asp Val Arg Gln Val Thr Asn
1               5                   10

<210> SEQ ID NO 152
<211> LENGTH: 14
<212> TYPE: PRT
<213> ORGANISM: Artificial Sequence
<220> FEATURE:
<223> OTHER INFORMATION: Synthetic

<400> SEQUENCE: 152

Asn Pro Asn Glu Val Ala Glu His Val Thr Ala Tyr Ile Glu
1               5                   10

<210> SEQ ID NO 153
<211> LENGTH: 14
<212> TYPE: PRT
<213> ORGANISM: Artificial Sequence
<220> FEATURE:
<223> OTHER INFORMATION: Synthetic

<400> SEQUENCE: 153

Asn Pro Ser Asp Ile Ala Ser Gln Val Ala Asp Tyr Phe Gln
1               5                   10

<210> SEQ ID NO 154
```

```
<211> LENGTH: 14
<212> TYPE: PRT
<213> ORGANISM: Artificial Sequence
<220> FEATURE:
<223> OTHER INFORMATION: Synthetic

<400> SEQUENCE: 154

Pro Ser Glu Ile Ala Asn Gln Ile Thr Asn Tyr Leu Ile Gln
1               5                   10

<210> SEQ ID NO 155
<211> LENGTH: 14
<212> TYPE: PRT
<213> ORGANISM: Artificial Sequence
<220> FEATURE:
<223> OTHER INFORMATION: Synthetic

<400> SEQUENCE: 155

Thr Ser Leu Pro Val Phe Asn Ala Gly Tyr Ile Asp Thr Ser
1               5                   10

<210> SEQ ID NO 156
<211> LENGTH: 15
<212> TYPE: PRT
<213> ORGANISM: Artificial Sequence
<220> FEATURE:
<223> OTHER INFORMATION: Synthetic

<400> SEQUENCE: 156

Ala Gly Val Ile Asp Arg Ser Ala Leu Gln Ser Ala Met Lys Ala
1               5                   10                  15

<210> SEQ ID NO 157
<211> LENGTH: 15
<212> TYPE: PRT
<213> ORGANISM: Artificial Sequence
<220> FEATURE:
<223> OTHER INFORMATION: Synthetic

<400> SEQUENCE: 157

Ala Lys Ala Ala Phe Glu Ala Leu Arg Ala Ala Glu Thr Glu Tyr
1               5                   10                  15

<210> SEQ ID NO 158
<211> LENGTH: 15
<212> TYPE: PRT
<213> ORGANISM: Artificial Sequence
<220> FEATURE:
<223> OTHER INFORMATION: Synthetic

<400> SEQUENCE: 158

Ala Lys Glu Ala Ile Asn Ser Leu Lys Thr Gln Ser Lys Asp Leu
1               5                   10                  15

<210> SEQ ID NO 159
<211> LENGTH: 15
<212> TYPE: PRT
<213> ORGANISM: Artificial Sequence
<220> FEATURE:
<223> OTHER INFORMATION: Synthetic

<400> SEQUENCE: 159

Ala Met Lys Ser Ile Leu Lys Thr Thr Ala Asp Leu Val Asp Gln
1               5                   10                  15

<210> SEQ ID NO 160
<211> LENGTH: 15
```

```
<212> TYPE: PRT
<213> ORGANISM: Artificial Sequence
<220> FEATURE:
<223> OTHER INFORMATION: Synthetic

<400> SEQUENCE: 160

Ala Thr Glu Ala Met Asp Ser Leu Glu Thr Gln Thr Ala Thr Asp
1               5                   10                  15

<210> SEQ ID NO 161
<211> LENGTH: 15
<212> TYPE: PRT
<213> ORGANISM: Artificial Sequence
<220> FEATURE:
<223> OTHER INFORMATION: Synthetic

<400> SEQUENCE: 161

Asp Ala Ala Lys Ala Ala Phe Asp Ser Leu Lys Ala Gly Ala Thr
1               5                   10                  15

<210> SEQ ID NO 162
<211> LENGTH: 15
<212> TYPE: PRT
<213> ORGANISM: Artificial Sequence
<220> FEATURE:
<223> OTHER INFORMATION: Synthetic

<400> SEQUENCE: 162

Asp Ala Ala Lys Ala Ala Phe Glu Ser Leu Lys Thr Gly Ala Thr
1               5                   10                  15

<210> SEQ ID NO 163
<211> LENGTH: 15
<212> TYPE: PRT
<213> ORGANISM: Artificial Sequence
<220> FEATURE:
<223> OTHER INFORMATION: Synthetic

<400> SEQUENCE: 163

Glu Ala Ala Lys Ala Ala Tyr Asp Ser Leu Lys Ala Gly Ala Thr
1               5                   10                  15

<210> SEQ ID NO 164
<211> LENGTH: 15
<212> TYPE: PRT
<213> ORGANISM: Artificial Sequence
<220> FEATURE:
<223> OTHER INFORMATION: Synthetic

<400> SEQUENCE: 164

Asp Ala Ala Lys Ala Ala Tyr Asp Ser Leu Arg Ala Gly Ala Thr
1               5                   10                  15

<210> SEQ ID NO 165
<211> LENGTH: 15
<212> TYPE: PRT
<213> ORGANISM: Artificial Sequence
<220> FEATURE:
<223> OTHER INFORMATION: Synthetic

<400> SEQUENCE: 165

Asp Ala Ala Lys Ala Ala Tyr Asp Thr Leu Lys Ala Gly Ala Ser
1               5                   10                  15

<210> SEQ ID NO 166
<211> LENGTH: 15
<212> TYPE: PRT
```

```
<213> ORGANISM: Artificial Sequence
<220> FEATURE:
<223> OTHER INFORMATION: Synthetic

<400> SEQUENCE: 166

Asp Asp Ala Arg Ala Ala Phe Asp Ser Ile Lys Ser Gly Ala Thr
1               5                   10                  15

<210> SEQ ID NO 167
<211> LENGTH: 15
<212> TYPE: PRT
<213> ORGANISM: Artificial Sequence
<220> FEATURE:
<223> OTHER INFORMATION: Synthetic

<400> SEQUENCE: 167

Asp Gly Thr Ser Thr Ala Thr Ala Thr Ser Ser Glu Ala Ala Asn
1               5                   10                  15

<210> SEQ ID NO 168
<211> LENGTH: 15
<212> TYPE: PRT
<213> ORGANISM: Artificial Sequence
<220> FEATURE:
<223> OTHER INFORMATION: Synthetic

<400> SEQUENCE: 168

Asp Pro Thr Asn Ala Ala Phe Asp Ser Leu Ala Ala Gly Ala Thr
1               5                   10                  15

<210> SEQ ID NO 169
<211> LENGTH: 15
<212> TYPE: PRT
<213> ORGANISM: Artificial Sequence
<220> FEATURE:
<223> OTHER INFORMATION: Synthetic

<400> SEQUENCE: 169

Glu Ala Met Asn Lys Leu Lys Ala Gln Ala Lys Glu Val Ile Asp
1               5                   10                  15

<210> SEQ ID NO 170
<211> LENGTH: 15
<212> TYPE: PRT
<213> ORGANISM: Artificial Sequence
<220> FEATURE:
<223> OTHER INFORMATION: Synthetic

<400> SEQUENCE: 170

Glu Ala Met Asn Val Leu Ser Ile Leu Glu Thr Asp Leu Ile Asp
1               5                   10                  15

<210> SEQ ID NO 171
<211> LENGTH: 15
<212> TYPE: PRT
<213> ORGANISM: Artificial Sequence
<220> FEATURE:
<223> OTHER INFORMATION: Synthetic

<400> SEQUENCE: 171

Glu Ala Met Asn Val Leu Ser Leu Leu Lys Thr Glu Leu Ile Glu
1               5                   10                  15

<210> SEQ ID NO 172
<211> LENGTH: 15
<212> TYPE: PRT
<213> ORGANISM: Artificial Sequence
```

-continued

```
<220> FEATURE:
<223> OTHER INFORMATION: Synthetic

<400> SEQUENCE: 172

Glu Ala Met Thr Asn Leu Asp Thr Gln Ala Ile Asn Ala Ile Asp
1               5                   10                  15

<210> SEQ ID NO 173
<211> LENGTH: 15
<212> TYPE: PRT
<213> ORGANISM: Artificial Sequence
<220> FEATURE:
<223> OTHER INFORMATION: Synthetic

<400> SEQUENCE: 173

Glu Gly Ala Asp Pro Ala Ala Val Ala Phe Asp Ser Leu Gln Ala
1               5                   10                  15

<210> SEQ ID NO 174
<211> LENGTH: 15
<212> TYPE: PRT
<213> ORGANISM: Artificial Sequence
<220> FEATURE:
<223> OTHER INFORMATION: Synthetic

<400> SEQUENCE: 174

Asp Gly Ser Glu Pro Ala Ala Val Ala Phe Asp Ala Leu Gln Ala
1               5                   10                  15

<210> SEQ ID NO 175
<211> LENGTH: 15
<212> TYPE: PRT
<213> ORGANISM: Artificial Sequence
<220> FEATURE:
<223> OTHER INFORMATION: Synthetic

<400> SEQUENCE: 175

Glu Gly Ser Asp Pro Ala Ala Val Ala Phe Glu Thr Leu Gln Ala
1               5                   10                  15

<210> SEQ ID NO 176
<211> LENGTH: 15
<212> TYPE: PRT
<213> ORGANISM: Artificial Sequence
<220> FEATURE:
<223> OTHER INFORMATION: Synthetic

<400> SEQUENCE: 176

Phe Asn Pro Ser Glu Thr Ile Ser Gln Leu Thr His Tyr Ile Glu
1               5                   10                  15

<210> SEQ ID NO 177
<211> LENGTH: 15
<212> TYPE: PRT
<213> ORGANISM: Artificial Sequence
<220> FEATURE:
<223> OTHER INFORMATION: Synthetic

<400> SEQUENCE: 177

Leu Pro Ala Phe Leu Gly Ile Ile Ala Thr Ser Thr Val Ser Ala
1               5                   10                  15

<210> SEQ ID NO 178
<211> LENGTH: 15
<212> TYPE: PRT
<213> ORGANISM: Artificial Sequence
<220> FEATURE:
```

```
<223> OTHER INFORMATION: Synthetic

<400> SEQUENCE: 178

Met Gly Phe Asn Pro Phe Val Ser Glu Val Ala His Gln Leu Thr
1               5                   10                  15

<210> SEQ ID NO 179
<211> LENGTH: 15
<212> TYPE: PRT
<213> ORGANISM: Artificial Sequence
<220> FEATURE:
<223> OTHER INFORMATION: Synthetic

<400> SEQUENCE: 179

Met His Phe Asn Val Ser Asp Ala Ala Asn Gln Ile Thr Asn Tyr
1               5                   10                  15

<210> SEQ ID NO 180
<211> LENGTH: 15
<212> TYPE: PRT
<213> ORGANISM: Artificial Sequence
<220> FEATURE:
<223> OTHER INFORMATION: Synthetic

<400> SEQUENCE: 180

Asn Pro Glu Val Ala Asp Ser Ser Gln Cys Thr Ser Tyr Ile Gln
1               5                   10                  15

<210> SEQ ID NO 181
<211> LENGTH: 15
<212> TYPE: PRT
<213> ORGANISM: Artificial Sequence
<220> FEATURE:
<223> OTHER INFORMATION: Synthetic

<400> SEQUENCE: 181

Asn Pro Ser Glu Ile Ala Leu Ser Asp Val Ala Asn Phe Ile Gln
1               5                   10                  15

<210> SEQ ID NO 182
<211> LENGTH: 15
<212> TYPE: PRT
<213> ORGANISM: Artificial Sequence
<220> FEATURE:
<223> OTHER INFORMATION: Synthetic

<400> SEQUENCE: 182

Gln Ala Met Asn Glu Ala Leu Lys Thr Ser Ala Thr Asp Leu Ile
1               5                   10                  15

<210> SEQ ID NO 183
<211> LENGTH: 15
<212> TYPE: PRT
<213> ORGANISM: Artificial Sequence
<220> FEATURE:
<223> OTHER INFORMATION: Synthetic

<400> SEQUENCE: 183

Gln Gly Asn Asp Pro Asp Val Lys Ala Ala Phe Asp Ser Leu Gln
1               5                   10                  15

<210> SEQ ID NO 184
<211> LENGTH: 15
<212> TYPE: PRT
<213> ORGANISM: Artificial Sequence
<220> FEATURE:
<223> OTHER INFORMATION: Synthetic
```

```
<400> SEQUENCE: 184

Thr Ala Val Ser Ile Ala Thr Glu Ala Met Asp Arg Leu Arg Thr
1               5                   10                  15

<210> SEQ ID NO 185
<211> LENGTH: 15
<212> TYPE: PRT
<213> ORGANISM: Artificial Sequence
<220> FEATURE:
<223> OTHER INFORMATION: Synthetic

<400> SEQUENCE: 185

Thr Glu Ile Met Asn Ser Leu Lys Asn Ser Asp Thr Asp Leu Ile
1               5                   10                  15

<210> SEQ ID NO 186
<211> LENGTH: 15
<212> TYPE: PRT
<213> ORGANISM: Artificial Sequence
<220> FEATURE:
<223> OTHER INFORMATION: Synthetic

<400> SEQUENCE: 186

Thr Ser Leu Pro Ala Phe Ala Ala Leu Ile Asp Ser Ala Ala Val
1               5                   10                  15

<210> SEQ ID NO 187
<211> LENGTH: 15
<212> TYPE: PRT
<213> ORGANISM: Artificial Sequence
<220> FEATURE:
<223> OTHER INFORMATION: Synthetic

<400> SEQUENCE: 187

Thr Ser Thr Ala Thr Ser Tyr Ser Thr Glu Leu Arg Thr Ala Met
1               5                   10                  15

<210> SEQ ID NO 188
<211> LENGTH: 16
<212> TYPE: PRT
<213> ORGANISM: Artificial Sequence
<220> FEATURE:
<223> OTHER INFORMATION: Synthetic

<400> SEQUENCE: 188

Ala Thr Ala Leu Pro Ala Phe Ala Thr Ser Ala Val Ala Ala Ile Thr
1               5                   10                  15

<210> SEQ ID NO 189
<211> LENGTH: 16
<212> TYPE: PRT
<213> ORGANISM: Artificial Sequence
<220> FEATURE:
<223> OTHER INFORMATION: Synthetic

<400> SEQUENCE: 189

Ala Thr Ser Phe Ser Thr Glu Ala Val Asn Ser Leu Thr Asn Leu Ile
1               5                   10                  15

<210> SEQ ID NO 190
<211> LENGTH: 16
<212> TYPE: PRT
<213> ORGANISM: Artificial Sequence
<220> FEATURE:
<223> OTHER INFORMATION: Synthetic
```

<400> SEQUENCE: 190

Ala Thr Ser Tyr Ala Thr Ala Glu Pro Met Asp Ala Thr Gln Ala Thr
1               5                   10                  15

<210> SEQ ID NO 191
<211> LENGTH: 16
<212> TYPE: PRT
<213> ORGANISM: Artificial Sequence
<220> FEATURE:
<223> OTHER INFORMATION: Synthetic

<400> SEQUENCE: 191

Asp Phe Leu Asn Pro Ser Glu Val Ala Ser Leu Gln Gln Val Tyr Asn
1               5                   10                  15

<210> SEQ ID NO 192
<211> LENGTH: 16
<212> TYPE: PRT
<213> ORGANISM: Artificial Sequence
<220> FEATURE:
<223> OTHER INFORMATION: Synthetic

<400> SEQUENCE: 192

Asp Phe Asn Pro Ser Ala Ser Ala Asp Val Ala Ala Ala Ile Thr Asn
1               5                   10                  15

<210> SEQ ID NO 193
<211> LENGTH: 16
<212> TYPE: PRT
<213> ORGANISM: Artificial Sequence
<220> FEATURE:
<223> OTHER INFORMATION: Synthetic

<400> SEQUENCE: 193

Asp Gly Thr Ser Ser Thr Ser Tyr Glu Thr Val Pro Leu Asn Ser Leu
1               5                   10                  15

<210> SEQ ID NO 194
<211> LENGTH: 16
<212> TYPE: PRT
<213> ORGANISM: Artificial Sequence
<220> FEATURE:
<223> OTHER INFORMATION: Synthetic

<400> SEQUENCE: 194

Glu Ala Met Asn Ser Leu Thr Thr Gln Ala Lys Ala Asp Leu Leu Glu
1               5                   10                  15

<210> SEQ ID NO 195
<211> LENGTH: 16
<212> TYPE: PRT
<213> ORGANISM: Artificial Sequence
<220> FEATURE:
<223> OTHER INFORMATION: Synthetic

<400> SEQUENCE: 195

Gly Ile Ile Asp Thr Asn Val Val Gln Ser Ala Ile Ser Asp Ala Gln
1               5                   10                  15

<210> SEQ ID NO 196
<211> LENGTH: 16
<212> TYPE: PRT
<213> ORGANISM: Artificial Sequence
<220> FEATURE:
<223> OTHER INFORMATION: Synthetic

<400> SEQUENCE: 196

Gly Val Ile Arg Asp Thr Pro Glu Ala Val Glu Ser Ala Phe Thr Asp
1               5                   10                  15

<210> SEQ ID NO 197
<211> LENGTH: 16
<212> TYPE: PRT
<213> ORGANISM: Artificial Sequence
<220> FEATURE:
<223> OTHER INFORMATION: Synthetic

<400> SEQUENCE: 197

Met Asp Phe Asn Pro Ser Glu Ile Ala Thr Thr Val Val Gln Tyr Ile
1               5                   10                  15

<210> SEQ ID NO 198
<211> LENGTH: 16
<212> TYPE: PRT
<213> ORGANISM: Artificial Sequence
<220> FEATURE:
<223> OTHER INFORMATION: Synthetic

<400> SEQUENCE: 198

Met Glu Phe His Ala Asp Glu Val Ala Ala Asn Val Thr Gly Tyr Ile
1               5                   10                  15

<210> SEQ ID NO 199
<211> LENGTH: 16
<212> TYPE: PRT
<213> ORGANISM: Artificial Sequence
<220> FEATURE:
<223> OTHER INFORMATION: Synthetic

<400> SEQUENCE: 199

Met Gly Phe Asn Pro Arg Glu Val Ser Lys Gln Val Ile Glu Asn Tyr
1               5                   10                  15

<210> SEQ ID NO 200
<211> LENGTH: 16
<212> TYPE: PRT
<213> ORGANISM: Artificial Sequence
<220> FEATURE:
<223> OTHER INFORMATION: Synthetic

<400> SEQUENCE: 200

Met Ser Phe Asn Ser Glu Val Leu Asn Ala Ser Gln Ile Thr Asp Tyr
1               5                   10                  15

<210> SEQ ID NO 201
<211> LENGTH: 16
<212> TYPE: PRT
<213> ORGANISM: Artificial Sequence
<220> FEATURE:
<223> OTHER INFORMATION: Synthetic

<400> SEQUENCE: 201

Asn Phe Asn Ala Ser Glu Pro Ser Gln Leu Val Thr Lys Tyr Ile Gln
1               5                   10                  15

<210> SEQ ID NO 202
<211> LENGTH: 16
<212> TYPE: PRT
<213> ORGANISM: Artificial Sequence
<220> FEATURE:
<223> OTHER INFORMATION: Synthetic

<400> SEQUENCE: 202

```
Thr Ala Ile Ser Tyr Gln Thr Glu Ala Met Gln Ser Leu Gln Ile Gln
1               5                   10                  15
```

<210> SEQ ID NO 203
<211> LENGTH: 16
<212> TYPE: PRT
<213> ORGANISM: Artificial Sequence
<220> FEATURE:
<223> OTHER INFORMATION: Synthetic

<400> SEQUENCE: 203

```
Val Ile Asp Ala Ser Asn Val Glu Lys Ala Phe Ile Ile Thr Asp Gly
1               5                   10                  15
```

<210> SEQ ID NO 204
<211> LENGTH: 16
<212> TYPE: PRT
<213> ORGANISM: Artificial Sequence
<220> FEATURE:
<223> OTHER INFORMATION: Synthetic

<400> SEQUENCE: 204

```
Val Thr Asp Thr Ser Glu Ala Ala Ile Thr Asp Lys His Gly Asp Met
1               5                   10                  15
```

<210> SEQ ID NO 205
<211> LENGTH: 16
<212> TYPE: PRT
<213> ORGANISM: Artificial Sequence
<220> FEATURE:
<223> OTHER INFORMATION: Synthetic

<400> SEQUENCE: 205

```
Tyr Ala Thr Glu Leu Ser Ser Leu Thr Thr Gln Val Ser Gln Leu Ile
1               5                   10                  15
```

<210> SEQ ID NO 206
<211> LENGTH: 16
<212> TYPE: PRT
<213> ORGANISM: Artificial Sequence
<220> FEATURE:
<223> OTHER INFORMATION: Synthetic

<400> SEQUENCE: 206

```
Tyr Ala Thr Lys Ala Leu Asn Ser Val Lys Thr Ala Asn Asp Asp Gln
1               5                   10                  15
```

<210> SEQ ID NO 207
<211> LENGTH: 16
<212> TYPE: PRT
<213> ORGANISM: Artificial Sequence
<220> FEATURE:
<223> OTHER INFORMATION: Synthetic

<400> SEQUENCE: 207

```
Tyr Ala Thr Lys Ser Leu Asn Ser Val Lys Thr Ser Asn Glu Glu Gln
1               5                   10                  15
```

<210> SEQ ID NO 208
<211> LENGTH: 16
<212> TYPE: PRT
<213> ORGANISM: Artificial Sequence
<220> FEATURE:
<223> OTHER INFORMATION: Synthetic

<400> SEQUENCE: 208

```
Tyr Ala Thr Asn Ala Leu Asn Ser Val Arg Thr Ala Asn Glu Asp Gln
```

<210> SEQ ID NO 209
<211> LENGTH: 17
<212> TYPE: PRT
<213> ORGANISM: Artificial Sequence
<220> FEATURE:
<223> OTHER INFORMATION: Synthetic

<400> SEQUENCE: 209

Ala Thr Glu Ala Leu Asn Glu Phe Lys Thr Gln Ile Thr Asp Leu Ala
1               5                   10                  15

Asp

<210> SEQ ID NO 210
<211> LENGTH: 17
<212> TYPE: PRT
<213> ORGANISM: Artificial Sequence
<220> FEATURE:
<223> OTHER INFORMATION: Synthetic

<400> SEQUENCE: 210

Ala Thr Ser Leu Pro Ala Phe Ala Gly Val Ile Asp Thr Ser Ala Val
1               5                   10                  15

Glu

<210> SEQ ID NO 211
<211> LENGTH: 17
<212> TYPE: PRT
<213> ORGANISM: Artificial Sequence
<220> FEATURE:
<223> OTHER INFORMATION: Synthetic

<400> SEQUENCE: 211

Asp Asp Gly Ser Thr Ser Asp Gly Thr Ser Tyr Ala Thr Asn Val Leu
1               5                   10                  15

Lys

<210> SEQ ID NO 212
<211> LENGTH: 17
<212> TYPE: PRT
<213> ORGANISM: Artificial Sequence
<220> FEATURE:
<223> OTHER INFORMATION: Synthetic

<400> SEQUENCE: 212

Asp Asp Pro Ala Thr Ala Ala Phe Asp Gly Gly Pro Ser Leu Thr Glu
1               5                   10                  15

Tyr

<210> SEQ ID NO 213
<211> LENGTH: 17
<212> TYPE: PRT
<213> ORGANISM: Artificial Sequence
<220> FEATURE:
<223> OTHER INFORMATION: Synthetic

<400> SEQUENCE: 213

Asp Phe Asn Pro Ser Lys Val Ala Gln Asp Pro Lys Val Thr Ala Tyr
1               5                   10                  15

Ile

<210> SEQ ID NO 214

```
<211> LENGTH: 17
<212> TYPE: PRT
<213> ORGANISM: Artificial Sequence
<220> FEATURE:
<223> OTHER INFORMATION: Synthetic

<400> SEQUENCE: 214

Asp Phe Asn Thr Ser Thr Glu Leu Ala Gly Gln Val Thr Asp Tyr Phe
1               5                   10                  15

Gln

<210> SEQ ID NO 215
<211> LENGTH: 17
<212> TYPE: PRT
<213> ORGANISM: Artificial Sequence
<220> FEATURE:
<223> OTHER INFORMATION: Synthetic

<400> SEQUENCE: 215

Asp Phe Ser Gly Ser Glu Val Ala Ala Gln Thr Asn Leu Gly Val Thr
1               5                   10                  15

Asn

<210> SEQ ID NO 216
<211> LENGTH: 17
<212> TYPE: PRT
<213> ORGANISM: Artificial Sequence
<220> FEATURE:
<223> OTHER INFORMATION: Synthetic

<400> SEQUENCE: 216

Asp Phe Ser Gln Ser Glu Ile Ala Ala Ala Gly Ala Val Thr Asp Tyr
1               5                   10                  15

Ile

<210> SEQ ID NO 217
<211> LENGTH: 17
<212> TYPE: PRT
<213> ORGANISM: Artificial Sequence
<220> FEATURE:
<223> OTHER INFORMATION: Synthetic

<400> SEQUENCE: 217

Glu Glu Glu Asp Pro Ala Asp Ala Ala Phe Pro Thr Leu Gln Ala Ser
1               5                   10                  15

Ala

<210> SEQ ID NO 218
<211> LENGTH: 17
<212> TYPE: PRT
<213> ORGANISM: Artificial Sequence
<220> FEATURE:
<223> OTHER INFORMATION: Synthetic

<400> SEQUENCE: 218

Phe Asn Pro Ser Val Glu Ile Gly Ser Gln Gln Asn Val Thr Asp Tyr
1               5                   10                  15

Val

<210> SEQ ID NO 219
<211> LENGTH: 17
<212> TYPE: PRT
<213> ORGANISM: Artificial Sequence
<220> FEATURE:
```

<223> OTHER INFORMATION: Synthetic

<400> SEQUENCE: 219

Gly Val Ile Asp Ser Ala Pro Val Val Gln Ser Ala Ile Thr Asn Gly
1               5                   10                  15
Gln

<210> SEQ ID NO 220
<211> LENGTH: 17
<212> TYPE: PRT
<213> ORGANISM: Artificial Sequence
<220> FEATURE:
<223> OTHER INFORMATION: Synthetic

<400> SEQUENCE: 220

Leu Pro Ala Phe Thr Gly Val Lys Ile Asp Val Glu Gly Ala Val Ile
1               5                   10                  15
Thr

<210> SEQ ID NO 221
<211> LENGTH: 17
<212> TYPE: PRT
<213> ORGANISM: Artificial Sequence
<220> FEATURE:
<223> OTHER INFORMATION: Synthetic

<400> SEQUENCE: 221

Met Asn Ser Leu Lys Thr Gln Ala Glu Glu Leu Val Met Thr Glu Leu
1               5                   10                  15
Ile

<210> SEQ ID NO 222
<211> LENGTH: 17
<212> TYPE: PRT
<213> ORGANISM: Artificial Sequence
<220> FEATURE:
<223> OTHER INFORMATION: Synthetic

<400> SEQUENCE: 222

Ser Lys Ala Thr Ser Phe Lys Ala Thr Glu Pro Ala Leu Asn Ser Leu
1               5                   10                  15
Lys

<210> SEQ ID NO 223
<211> LENGTH: 17
<212> TYPE: PRT
<213> ORGANISM: Artificial Sequence
<220> FEATURE:
<223> OTHER INFORMATION: Synthetic

<400> SEQUENCE: 223

Thr Asp Ala Lys Asn Glu Leu Thr Thr Gln Val Thr Asp Leu Thr Thr
1               5                   10                  15
Gln

<210> SEQ ID NO 224
<211> LENGTH: 17
<212> TYPE: PRT
<213> ORGANISM: Artificial Sequence
<220> FEATURE:
<223> OTHER INFORMATION: Synthetic

<400> SEQUENCE: 224

```
Thr Glu Gly Met Asn Ser Leu Lys Thr Leu Ala Ser Gln Leu Thr Asp
1               5                   10                  15

Gln

<210> SEQ ID NO 225
<211> LENGTH: 17
<212> TYPE: PRT
<213> ORGANISM: Artificial Sequence
<220> FEATURE:
<223> OTHER INFORMATION: Synthetic

<400> SEQUENCE: 225

Thr Glu Ser Leu Gln Ser Leu Lys Ala Gln Ile Met Asp Leu Ile Asp
1               5                   10                  15

Gln

<210> SEQ ID NO 226
<211> LENGTH: 17
<212> TYPE: PRT
<213> ORGANISM: Artificial Sequence
<220> FEATURE:
<223> OTHER INFORMATION: Synthetic

<400> SEQUENCE: 226

Thr Glu Thr Leu Gln Ser Leu Met Lys Ser Gln Ala Thr Asp Leu Leu
1               5                   10                  15

Asn

<210> SEQ ID NO 227
<211> LENGTH: 17
<212> TYPE: PRT
<213> ORGANISM: Artificial Sequence
<220> FEATURE:
<223> OTHER INFORMATION: Synthetic

<400> SEQUENCE: 227

Thr Glu Val Leu Asn Phe Leu Lys Thr Gln Thr Asp Leu Val Ile Asp
1               5                   10                  15

Gln

<210> SEQ ID NO 228
<211> LENGTH: 17
<212> TYPE: PRT
<213> ORGANISM: Artificial Sequence
<220> FEATURE:
<223> OTHER INFORMATION: Synthetic

<400> SEQUENCE: 228

Val Phe Asp Ser Ser Ala Ala Asp Lys Ala Ile Gln Gly Asp Leu Lys
1               5                   10                  15

Ala

<210> SEQ ID NO 229
<211> LENGTH: 17
<212> TYPE: PRT
<213> ORGANISM: Artificial Sequence
<220> FEATURE:
<223> OTHER INFORMATION: Synthetic

<400> SEQUENCE: 229

Val Thr Asp Thr Ser Ala Ile Glu Ala Ala Val Val Gln Ile Ile Thr
1               5                   10                  15

Asp
```

```
<210> SEQ ID NO 230
<211> LENGTH: 17
<212> TYPE: PRT
<213> ORGANISM: Artificial Sequence
<220> FEATURE:
<223> OTHER INFORMATION: Synthetic

<400> SEQUENCE: 230

Tyr Ala Glu Ala Ser Leu Lys Thr Thr Ala Thr Arg Glu Asp Leu Ile
1               5                   10                  15

Glu

<210> SEQ ID NO 231
<211> LENGTH: 17
<212> TYPE: PRT
<213> ORGANISM: Artificial Sequence
<220> FEATURE:
<223> OTHER INFORMATION: Synthetic

<400> SEQUENCE: 231

Met Asp Phe Asn Pro Ser Glu Val Ala Ser Gln Val Thr Asn Tyr Ile
1               5                   10                  15

Gln

<210> SEQ ID NO 232
<211> LENGTH: 18
<212> TYPE: PRT
<213> ORGANISM: Artificial Sequence
<220> FEATURE:
<223> OTHER INFORMATION: Synthetic

<400> SEQUENCE: 232

Ala Ala Gly Asp Asp Pro Ala Val Ala Ala Val Gln Thr Ala Ala Thr
1               5                   10                  15

Glu Tyr

<210> SEQ ID NO 233
<211> LENGTH: 18
<212> TYPE: PRT
<213> ORGANISM: Artificial Sequence
<220> FEATURE:
<223> OTHER INFORMATION: Synthetic

<400> SEQUENCE: 233

Ala Ala Thr Leu Arg Ile Phe Ala Ile Asp Thr Thr Ala Val Glu Ser
1               5                   10                  15

Ala Ile

<210> SEQ ID NO 234
<211> LENGTH: 18
<212> TYPE: PRT
<213> ORGANISM: Artificial Sequence
<220> FEATURE:
<223> OTHER INFORMATION: Synthetic

<400> SEQUENCE: 234

Ala Ser Asp Gly Thr Ser Ser Thr Ser Tyr Glu Thr Val Pro Val Asn
1               5                   10                  15

Ser Leu

<210> SEQ ID NO 235
<211> LENGTH: 18
```

```
<212> TYPE: PRT
<213> ORGANISM: Artificial Sequence
<220> FEATURE:
<223> OTHER INFORMATION: Synthetic

<400> SEQUENCE: 235

Ala Thr Gln Ala Ala Asn Asn Leu Ala Thr Gln Ala Thr Asn Leu Val
1               5                   10                  15
Asn Gln

<210> SEQ ID NO 236
<211> LENGTH: 18
<212> TYPE: PRT
<213> ORGANISM: Artificial Sequence
<220> FEATURE:
<223> OTHER INFORMATION: Synthetic

<400> SEQUENCE: 236

Asp Phe Asn Pro Ala Glu Val Ala Lys Thr Leu Ser Ser Glu Asn Ile
1               5                   10                  15
Thr Asn

<210> SEQ ID NO 237
<211> LENGTH: 18
<212> TYPE: PRT
<213> ORGANISM: Artificial Sequence
<220> FEATURE:
<223> OTHER INFORMATION: Synthetic

<400> SEQUENCE: 237

Asp Gly Asp Thr Ala Thr Ala Asn Ser Tyr Leu Thr Glu Ala Ala Asn
1               5                   10                  15
Ser Leu

<210> SEQ ID NO 238
<211> LENGTH: 18
<212> TYPE: PRT
<213> ORGANISM: Artificial Sequence
<220> FEATURE:
<223> OTHER INFORMATION: Synthetic

<400> SEQUENCE: 238

Glu Asp Asp Asp Ala Val Lys Ala Ala Phe Asp Lys Leu Gln Ala Ser
1               5                   10                  15
Gln Thr

<210> SEQ ID NO 239
<211> LENGTH: 18
<212> TYPE: PRT
<213> ORGANISM: Artificial Sequence
<220> FEATURE:
<223> OTHER INFORMATION: Synthetic

<400> SEQUENCE: 239

Glu Glu Glu Glu Ala Val Lys Ala Ala Phe Glu Lys Leu Gln Ala Ser
1               5                   10                  15
Gln Thr

<210> SEQ ID NO 240
<211> LENGTH: 18
<212> TYPE: PRT
<213> ORGANISM: Artificial Sequence
<220> FEATURE:
<223> OTHER INFORMATION: Synthetic
```

```
<400> SEQUENCE: 240

Glu Asp Asp Glu Ala Val Lys Ser Ala Phe Asp Lys Leu Gln Ala Ser
1               5                   10                  15

Gln Thr

<210> SEQ ID NO 241
<211> LENGTH: 18
<212> TYPE: PRT
<213> ORGANISM: Artificial Sequence
<220> FEATURE:
<223> OTHER INFORMATION: Synthetic

<400> SEQUENCE: 241

Glu Gly Asp Asp Asp Ala Ala Val Lys Ala Ala Phe Glu Lys Leu Gln
1               5                   10                  15

Ala Ser

<210> SEQ ID NO 242
<211> LENGTH: 18
<212> TYPE: PRT
<213> ORGANISM: Artificial Sequence
<220> FEATURE:
<223> OTHER INFORMATION: Synthetic

<400> SEQUENCE: 242

Glu Gly Thr Asp Asp Ala Ala Val Lys Ala Ala Phe Glu Lys Leu Gln
1               5                   10                  15

Ala Ser

<210> SEQ ID NO 243
<211> LENGTH: 18
<212> TYPE: PRT
<213> ORGANISM: Artificial Sequence
<220> FEATURE:
<223> OTHER INFORMATION: Synthetic

<400> SEQUENCE: 243

Phe Ser Pro Thr Glu Val Ala Ser Leu Leu Asp Val Gly Thr Asn Tyr
1               5                   10                  15

Val Gln

<210> SEQ ID NO 244
<211> LENGTH: 18
<212> TYPE: PRT
<213> ORGANISM: Artificial Sequence
<220> FEATURE:
<223> OTHER INFORMATION: Synthetic

<400> SEQUENCE: 244

Ile Asp Thr Ser Ala Ile Glu Asn Ala Val Lys Lys Ser Asp Gly Gln
1               5                   10                  15

Gly Glu

<210> SEQ ID NO 245
<211> LENGTH: 18
<212> TYPE: PRT
<213> ORGANISM: Artificial Sequence
<220> FEATURE:
<223> OTHER INFORMATION: Synthetic

<400> SEQUENCE: 245

Ile Asp Thr Ser Ala Ile Glu Thr Ala Val Arg Lys Ser Asp Gly Gln
```

```
1               5                   10                  15

Gly Glu

<210> SEQ ID NO 246
<211> LENGTH: 18
<212> TYPE: PRT
<213> ORGANISM: Artificial Sequence
<220> FEATURE:
<223> OTHER INFORMATION: Synthetic

<400> SEQUENCE: 246

Met Asp Phe Leu Leu Asn Pro Glu Asn Ile Ala Ala Val Thr Asn Tyr
1               5                   10                  15

Ala Gln

<210> SEQ ID NO 247
<211> LENGTH: 18
<212> TYPE: PRT
<213> ORGANISM: Artificial Sequence
<220> FEATURE:
<223> OTHER INFORMATION: Synthetic

<400> SEQUENCE: 247

Met Glu Phe Leu Tyr Lys Pro Asp Val Ala Ala Glu Leu Thr Asp Tyr
1               5                   10                  15

Ile Gln

<210> SEQ ID NO 248
<211> LENGTH: 18
<212> TYPE: PRT
<213> ORGANISM: Artificial Sequence
<220> FEATURE:
<223> OTHER INFORMATION: Synthetic

<400> SEQUENCE: 248

Met Asp Tyr Leu Val Pro Ser Pro Thr Glu Val Pro Ser Met Val Thr
1               5                   10                  15

Asp Tyr

<210> SEQ ID NO 249
<211> LENGTH: 18
<212> TYPE: PRT
<213> ORGANISM: Artificial Sequence
<220> FEATURE:
<223> OTHER INFORMATION: Synthetic

<400> SEQUENCE: 249

Met Phe Asn Pro Ser Val Glu Ile Gly Ser Gln Gln Asn Val Thr Asp
1               5                   10                  15

Tyr Val

<210> SEQ ID NO 250
<211> LENGTH: 18
<212> TYPE: PRT
<213> ORGANISM: Artificial Sequence
<220> FEATURE:
<223> OTHER INFORMATION: Synthetic

<400> SEQUENCE: 250

Gln Ala Met Asp Ser Leu Lys Thr Ala Thr Ala Ser Val Ala Asp Leu
1               5                   10                  15

Leu Asp
```

```
<210> SEQ ID NO 251
<211> LENGTH: 18
<212> TYPE: PRT
<213> ORGANISM: Artificial Sequence
<220> FEATURE:
<223> OTHER INFORMATION: Synthetic

<400> SEQUENCE: 251

Ser Glu Val Ala Ala Ala Lys Gln Arg His Gln Gln Val Thr Asn Tyr
1               5                   10                  15

Ile Gln

<210> SEQ ID NO 252
<211> LENGTH: 18
<212> TYPE: PRT
<213> ORGANISM: Artificial Sequence
<220> FEATURE:
<223> OTHER INFORMATION: Synthetic

<400> SEQUENCE: 252

Ser Asn Ala Ile Glu Ala Lys Asn Gly Leu Lys Lys Gln Ala Ile Asp
1               5                   10                  15

Leu Ile

<210> SEQ ID NO 253
<211> LENGTH: 18
<212> TYPE: PRT
<213> ORGANISM: Artificial Sequence
<220> FEATURE:
<223> OTHER INFORMATION: Synthetic

<400> SEQUENCE: 253

Thr Asn Met Ser Thr Ala Tyr Ala Phe Leu Glu Ala Ile Asn Ser Leu
1               5                   10                  15

Lys Thr

<210> SEQ ID NO 254
<211> LENGTH: 18
<212> TYPE: PRT
<213> ORGANISM: Artificial Sequence
<220> FEATURE:
<223> OTHER INFORMATION: Synthetic

<400> SEQUENCE: 254

Thr Ser Ala Val Ala Ser Ala Asp Thr Asp Gly Ser Asp Asp Gln Gly
1               5                   10                  15

Asp Met

<210> SEQ ID NO 255
<211> LENGTH: 18
<212> TYPE: PRT
<213> ORGANISM: Artificial Sequence
<220> FEATURE:
<223> OTHER INFORMATION: Synthetic

<400> SEQUENCE: 255

Met Gln Ser Val Ile Thr Asp Val Thr Gly Gln Leu Thr Ala Val Gln
1               5                   10                  15

Ala Asp

<210> SEQ ID NO 256
<211> LENGTH: 19
<212> TYPE: PRT
```

<213> ORGANISM: Artificial Sequence
<220> FEATURE:
<223> OTHER INFORMATION: Synthetic

<400> SEQUENCE: 256

Ala Glu Leu Gly Asp Asp Pro Ala Ala Ile Asp Ala Leu Ala Ala
1               5                   10                  15

Ala Ala Thr

<210> SEQ ID NO 257
<211> LENGTH: 19
<212> TYPE: PRT
<213> ORGANISM: Artificial Sequence
<220> FEATURE:
<223> OTHER INFORMATION: Synthetic

<400> SEQUENCE: 257

Ala Gly Val Ile Asn Thr Ala Val Ile Glu Gln Ala Ile Thr Asp Ala
1               5                   10                  15

Ser Asp Met

<210> SEQ ID NO 258
<211> LENGTH: 19
<212> TYPE: PRT
<213> ORGANISM: Artificial Sequence
<220> FEATURE:
<223> OTHER INFORMATION: Synthetic

<400> SEQUENCE: 258

Asp Phe Tyr Pro Ser Glu Leu Ala Gly Gln Ile Asp Gln Leu Ala Asp
1               5                   10                  15

Tyr Ile Gln

<210> SEQ ID NO 259
<211> LENGTH: 19
<212> TYPE: PRT
<213> ORGANISM: Artificial Sequence
<220> FEATURE:
<223> OTHER INFORMATION: Synthetic

<400> SEQUENCE: 259

Glu Ala Leu Ser Ser Leu Lys Ile Lys Ile Asp Asp Gln Pro Thr Asp
1               5                   10                  15

Leu Ile Asp

<210> SEQ ID NO 260
<211> LENGTH: 19
<212> TYPE: PRT
<213> ORGANISM: Artificial Sequence
<220> FEATURE:
<223> OTHER INFORMATION: Synthetic

<400> SEQUENCE: 260

Glu Glu Met Ala Ala Ala Ala Asn Ser Leu Lys Thr Gln Ala Lys Glu
1               5                   10                  15

Leu Val Asp

<210> SEQ ID NO 261
<211> LENGTH: 19
<212> TYPE: PRT
<213> ORGANISM: Artificial Sequence
<220> FEATURE:
<223> OTHER INFORMATION: Synthetic

```
<400> SEQUENCE: 261

Glu Gly Asp Asp Pro Leu Ser Arg Leu Ala Arg Ala Ser Leu Gln Ala
1               5                   10                  15

Ser Ala Thr

<210> SEQ ID NO 262
<211> LENGTH: 19
<212> TYPE: PRT
<213> ORGANISM: Artificial Sequence
<220> FEATURE:
<223> OTHER INFORMATION: Synthetic

<400> SEQUENCE: 262

Phe Asn Pro Ser Glu Asn Ala Ser Lys Leu Thr Asn Arg Asn Ile His
1               5                   10                  15

Tyr Ile Gln

<210> SEQ ID NO 263
<211> LENGTH: 19
<212> TYPE: PRT
<213> ORGANISM: Artificial Sequence
<220> FEATURE:
<223> OTHER INFORMATION: Synthetic

<400> SEQUENCE: 263

Ile Asp Thr Ser Ser Ala Ser Ser Ile Ala Ala Glu Ala Ser Ile
1               5                   10                  15

Ala Ala Gly

<210> SEQ ID NO 264
<211> LENGTH: 19
<212> TYPE: PRT
<213> ORGANISM: Artificial Sequence
<220> FEATURE:
<223> OTHER INFORMATION: Synthetic

<400> SEQUENCE: 264

Leu Pro Gly Phe Leu Gly Val Ile Asp Thr Ala Ile Ser Lys Ile Glu
1               5                   10                  15

Ser Val Ile

<210> SEQ ID NO 265
<211> LENGTH: 19
<212> TYPE: PRT
<213> ORGANISM: Artificial Sequence
<220> FEATURE:
<223> OTHER INFORMATION: Synthetic

<400> SEQUENCE: 265

Met Glu Ile Asn Pro Ser Glu Val Thr Lys Ile Leu Lys Glu Gln Ile
1               5                   10                  15

Lys Asn Tyr

<210> SEQ ID NO 266
<211> LENGTH: 19
<212> TYPE: PRT
<213> ORGANISM: Artificial Sequence
<220> FEATURE:
<223> OTHER INFORMATION: Synthetic

<400> SEQUENCE: 266

Met Glu Ile Asn Pro Ser Glu Val Thr Lys Ile Leu Lys Asp Gln Ile
1               5                   10                  15
```

Arg Asn Tyr

<210> SEQ ID NO 267
<211> LENGTH: 19
<212> TYPE: PRT
<213> ORGANISM: Artificial Sequence
<220> FEATURE:
<223> OTHER INFORMATION: Synthetic

<400> SEQUENCE: 267

Met Gln Ser Leu Lys Thr Gln Glu Glu Glu Lys Arg Lys Ala Asp Leu
1               5                   10                  15

Val Asp Gln

<210> SEQ ID NO 268
<211> LENGTH: 19
<212> TYPE: PRT
<213> ORGANISM: Artificial Sequence
<220> FEATURE:
<223> OTHER INFORMATION: Synthetic

<400> SEQUENCE: 268

Thr Ala Ile Thr Ser Tyr Ala Thr Glu Asn Ala Thr Gln Met Asn Ser
1               5                   10                  15

Ile Lys Thr

<210> SEQ ID NO 269
<211> LENGTH: 19
<212> TYPE: PRT
<213> ORGANISM: Artificial Sequence
<220> FEATURE:
<223> OTHER INFORMATION: Synthetic

<400> SEQUENCE: 269

Thr Lys Tyr Glu Thr Glu Ala Lys His Leu Lys Ser Leu Glu Thr Gln
1               5                   10                  15

Gly Thr Asp

<210> SEQ ID NO 270
<211> LENGTH: 19
<212> TYPE: PRT
<213> ORGANISM: Artificial Sequence
<220> FEATURE:
<223> OTHER INFORMATION: Synthetic

<400> SEQUENCE: 270

Thr Ser Leu Pro Ser Ile Ser Gly Gly Ile Glu Thr Ser Glu Ser Ala
1               5                   10                  15

Gly Thr Asp

<210> SEQ ID NO 271
<211> LENGTH: 19
<212> TYPE: PRT
<213> ORGANISM: Artificial Sequence
<220> FEATURE:
<223> OTHER INFORMATION: Synthetic

<400> SEQUENCE: 271

Thr Thr Thr Gly Tyr Gly Met Asn Ser Leu Lys Ser Lys Glu Thr Asn
1               5                   10                  15

Leu Ile Asp

-continued

<210> SEQ ID NO 272
<211> LENGTH: 19
<212> TYPE: PRT
<213> ORGANISM: Artificial Sequence
<220> FEATURE:
<223> OTHER INFORMATION: Synthetic

<400> SEQUENCE: 272

Ser Gly Val Gly Asp Gly Val Asp Val Val Ser Ala Ile Glu Gly Ala
1               5                   10                  15

Ala Gly Pro

<210> SEQ ID NO 273
<211> LENGTH: 20
<212> TYPE: PRT
<213> ORGANISM: Artificial Sequence
<220> FEATURE:
<223> OTHER INFORMATION: Synthetic

<400> SEQUENCE: 273

Ala Asp Asp Gly Glu Gly Phe Thr Gly Ser Thr Thr Glu Ala Met Asn
1               5                   10                  15

Lys Leu Lys Thr
            20

<210> SEQ ID NO 274
<211> LENGTH: 20
<212> TYPE: PRT
<213> ORGANISM: Artificial Sequence
<220> FEATURE:
<223> OTHER INFORMATION: Synthetic

<400> SEQUENCE: 274

Ala Glu Gly Glu Gly Ala Ser Ala Val Phe Thr Ala Leu Gln Ala Lys
1               5                   10                  15

Ala Thr Glu Tyr
            20

<210> SEQ ID NO 275
<211> LENGTH: 20
<212> TYPE: PRT
<213> ORGANISM: Artificial Sequence
<220> FEATURE:
<223> OTHER INFORMATION: Synthetic

<400> SEQUENCE: 275

Ala Gly Asp Gly Thr Thr Thr Ala Thr Val Leu Thr Gln Ser Ile Ala
1               5                   10                  15

Thr Glu Gly Met
            20

<210> SEQ ID NO 276
<211> LENGTH: 20
<212> TYPE: PRT
<213> ORGANISM: Artificial Sequence
<220> FEATURE:
<223> OTHER INFORMATION: Synthetic

<400> SEQUENCE: 276

Ala Gly Glu Gly Thr Thr Thr Ala Thr Val Leu Thr Gln Ser Ile Ala
1               5                   10                  15

Thr Asp Gly Met
            20

```
<210> SEQ ID NO 277
<211> LENGTH: 20
<212> TYPE: PRT
<213> ORGANISM: Artificial Sequence
<220> FEATURE:
<223> OTHER INFORMATION: Synthetic

<400> SEQUENCE: 277

Ala Ser Val Ile Ser Thr Arg Asn Val Glu Thr Ala Met Lys Asn Gly
1               5                   10                  15

Gln Gly Asp Leu
            20

<210> SEQ ID NO 278
<211> LENGTH: 20
<212> TYPE: PRT
<213> ORGANISM: Artificial Sequence
<220> FEATURE:
<223> OTHER INFORMATION: Synthetic

<400> SEQUENCE: 278

Asp Asp Ala Ser Ser Thr Val Glu Ser Ala Thr Ser Ser Ala Thr Glu
1               5                   10                  15

Ala Met Glu Ser
            20

<210> SEQ ID NO 279
<211> LENGTH: 20
<212> TYPE: PRT
<213> ORGANISM: Artificial Sequence
<220> FEATURE:
<223> OTHER INFORMATION: Synthetic

<400> SEQUENCE: 279

Asp Asp Ala Thr Ser Gln Ala Lys Ala Ala Phe Asp Ser Leu Thr Ala
1               5                   10                  15

Gln Ala Thr Glu
            20

<210> SEQ ID NO 280
<211> LENGTH: 20
<212> TYPE: PRT
<213> ORGANISM: Artificial Sequence
<220> FEATURE:
<223> OTHER INFORMATION: Synthetic

<400> SEQUENCE: 280

Asp Asp Pro Asn Ala Thr Ala Ala Phe Glu Ser Leu Gln Ala Asp Ile
1               5                   10                  15

Ala Ala Asn Glu
            20

<210> SEQ ID NO 281
<211> LENGTH: 20
<212> TYPE: PRT
<213> ORGANISM: Artificial Sequence
<220> FEATURE:
<223> OTHER INFORMATION: Synthetic

<400> SEQUENCE: 281

Asp Thr Ser Ser Glu Ser Ala Ile Glu Ser Ala Val Gly Gln Gly Asp
1               5                   10                  15

Leu Ala Met Lys
            20
```

<210> SEQ ID NO 282
<211> LENGTH: 20
<212> TYPE: PRT
<213> ORGANISM: Artificial Sequence
<220> FEATURE:
<223> OTHER INFORMATION: Synthetic

<400> SEQUENCE: 282

Glu Gly Thr Asp Asp Ala Val Lys Ala Ala Phe Glu Lys Leu Gln
1               5                   10                  15

Ala Ser Gln Thr
            20

<210> SEQ ID NO 283
<211> LENGTH: 20
<212> TYPE: PRT
<213> ORGANISM: Artificial Sequence
<220> FEATURE:
<223> OTHER INFORMATION: Synthetic

<400> SEQUENCE: 283

Met Asp Phe Asn Pro Ser Glu Gln Gly Ala Lys Val Leu Lys Gln Val
1               5                   10                  15

Thr Asp Phe Val
            20

<210> SEQ ID NO 284
<211> LENGTH: 20
<212> TYPE: PRT
<213> ORGANISM: Artificial Sequence
<220> FEATURE:
<223> OTHER INFORMATION: Synthetic

<400> SEQUENCE: 284

Met Gln Phe Asn Pro Tyr Glu Ile Ser Ser Gln Ile Lys Gln Asn Gly
1               5                   10                  15

Gly Tyr Ile Gln
            20

<210> SEQ ID NO 285
<211> LENGTH: 20
<212> TYPE: PRT
<213> ORGANISM: Artificial Sequence
<220> FEATURE:
<223> OTHER INFORMATION: Synthetic

<400> SEQUENCE: 285

Thr Ser Leu Pro Gly Val Ile Gly Ala Ala Val Gln Ser Ala Lys
1               5                   10                  15

Thr Glu Gly Gln
            20

<210> SEQ ID NO 286
<211> LENGTH: 20
<212> TYPE: PRT
<213> ORGANISM: Artificial Sequence
<220> FEATURE:
<223> OTHER INFORMATION: Synthetic

<400> SEQUENCE: 286

Val Ile Asp Val Ser Ser Ala Ser His Val Gln Ser Phe Val Glu Ser
1               5                   10                  15

Ala Ile Thr Asp
            20

<210> SEQ ID NO 287
<211> LENGTH: 20
<212> TYPE: PRT
<213> ORGANISM: Artificial Sequence
<220> FEATURE:
<223> OTHER INFORMATION: Synthetic

<400> SEQUENCE: 287

Tyr Ser Thr Glu Asp Ala Ala Ala Met Asn Ala Ala Asp Gly Leu Lys
1               5                   10                  15

Thr Gln Ala Thr
            20

<210> SEQ ID NO 288
<211> LENGTH: 21
<212> TYPE: PRT
<213> ORGANISM: Artificial Sequence
<220> FEATURE:
<223> OTHER INFORMATION: Synthetic

<400> SEQUENCE: 288

Ala Ala Gly Asn Asp Arg Val Phe Thr Arg Arg Ala Phe Thr Met His
1               5                   10                  15

Pro Tyr Gly Val Lys
            20

<210> SEQ ID NO 289
<211> LENGTH: 21
<212> TYPE: PRT
<213> ORGANISM: Artificial Sequence
<220> FEATURE:
<223> OTHER INFORMATION: Synthetic

<400> SEQUENCE: 289

Ala Asp Gln Gly Thr Met Thr Ala Thr Asp Tyr Ala Thr Tyr Thr Ser
1               5                   10                  15

Leu Phe Glu Ala Met
            20

<210> SEQ ID NO 290
<211> LENGTH: 21
<212> TYPE: PRT
<213> ORGANISM: Artificial Sequence
<220> FEATURE:
<223> OTHER INFORMATION: Synthetic

<400> SEQUENCE: 290

Ala Pro Gly Glu Asp Pro Glu Ala Arg Ala Ala Tyr Asp Glu Met Gln
1               5                   10                  15

Ala Ala Ala Ala Glu
            20

<210> SEQ ID NO 291
<211> LENGTH: 21
<212> TYPE: PRT
<213> ORGANISM: Artificial Sequence
<220> FEATURE:
<223> OTHER INFORMATION: Synthetic

<400> SEQUENCE: 291

Asp Asp Gly Thr Ala Thr Ile Gly Val Ser Ala Tyr Ala Val Glu Ala
1               5                   10                  15

Leu Thr Asp Leu Val

```
                  20

<210> SEQ ID NO 292
<211> LENGTH: 21
<212> TYPE: PRT
<213> ORGANISM: Artificial Sequence
<220> FEATURE:
<223> OTHER INFORMATION: Synthetic

<400> SEQUENCE: 292

Asp Gly Tyr Gly Lys Ala Thr Ser Phe Ser Thr Glu Ala Val Asn Ser
1               5                   10                  15

Leu Thr Asn Ile Ile
            20

<210> SEQ ID NO 293
<211> LENGTH: 21
<212> TYPE: PRT
<213> ORGANISM: Artificial Sequence
<220> FEATURE:
<223> OTHER INFORMATION: Synthetic

<400> SEQUENCE: 293

Gly Val Ile Asp Thr Ser Ala Val Glu Ser Ala Ile Thr Asp Gly Gln
1               5                   10                  15

Gly Asp Met Lys Ala
            20

<210> SEQ ID NO 294
<211> LENGTH: 21
<212> TYPE: PRT
<213> ORGANISM: Artificial Sequence
<220> FEATURE:
<223> OTHER INFORMATION: Synthetic

<400> SEQUENCE: 294

Leu Asp Phe Asn Ser Ser Glu Val Ala Leu Ser Glu Gly Met Gln Val
1               5                   10                  15

Thr Ser Phe Leu Gln
            20

<210> SEQ ID NO 295
<211> LENGTH: 21
<212> TYPE: PRT
<213> ORGANISM: Artificial Sequence
<220> FEATURE:
<223> OTHER INFORMATION: Synthetic

<400> SEQUENCE: 295

Leu Pro Asp Phe Ala Gly Val Val Asp Asp Tyr Asp Glu Phe Thr Asp
1               5                   10                  15

Ala Val Glu Ser Ala
            20

<210> SEQ ID NO 296
<211> LENGTH: 21
<212> TYPE: PRT
<213> ORGANISM: Artificial Sequence
<220> FEATURE:
<223> OTHER INFORMATION: Synthetic

<400> SEQUENCE: 296

Thr Gly Leu Pro His Ala Phe Pro Ala Val Ser Gly Ala Ser Ala Val
1               5                   10                  15
```

Glu Ser Ala Ile Thr
         20

<210> SEQ ID NO 297
<211> LENGTH: 21
<212> TYPE: PRT
<213> ORGANISM: Artificial Sequence
<220> FEATURE:
<223> OTHER INFORMATION: Synthetic

<400> SEQUENCE: 297

Thr Gly Leu Pro His Ala Phe Pro Ala Val Ser Gly Ala Ser Ala Val
1               5                   10                  15

Glu Ser Ala Ile Thr
         20

<210> SEQ ID NO 298
<211> LENGTH: 21
<212> TYPE: PRT
<213> ORGANISM: Artificial Sequence
<220> FEATURE:
<223> OTHER INFORMATION: Synthetic

<400> SEQUENCE: 298

Thr Ser Ala Glu Ala Thr Tyr Glu Lys Ala Met Asn Ala Leu Lys Ile
1               5                   10                  15

Gln Ala Ile Asp Leu
         20

<210> SEQ ID NO 299
<211> LENGTH: 21
<212> TYPE: PRT
<213> ORGANISM: Artificial Sequence
<220> FEATURE:
<223> OTHER INFORMATION: Synthetic

<400> SEQUENCE: 299

Ala Glu Gly Asp Asp Pro Ala Lys Ala Ala Phe Asp Ser Leu Gln Ala
1               5                   10                  15

Ser Ala Thr Glu Tyr
         20

<210> SEQ ID NO 300
<211> LENGTH: 21
<212> TYPE: PRT
<213> ORGANISM: Artificial Sequence
<220> FEATURE:
<223> OTHER INFORMATION: Synthetic

<400> SEQUENCE: 300

Ala Glu Gly Asp Asp Pro Ala Lys Ala Ala Phe Asn Ser Leu Gln Ala
1               5                   10                  15

Ser Ala Thr Glu Tyr
         20

<210> SEQ ID NO 301
<211> LENGTH: 22
<212> TYPE: PRT
<213> ORGANISM: Artificial Sequence
<220> FEATURE:
<223> OTHER INFORMATION: Synthetic

<400> SEQUENCE: 301

Ala Glu Gly Asp Ala Ser Ser Gln Ala Lys Ala Ala Phe Asp Ser Leu
1               5                   10                  15

Thr Ala Gln Ala Thr Glu
            20

<210> SEQ ID NO 302
<211> LENGTH: 22
<212> TYPE: PRT
<213> ORGANISM: Artificial Sequence
<220> FEATURE:
<223> OTHER INFORMATION: Synthetic

<400> SEQUENCE: 302

Ala Glu Gly Asp Ala Thr Ser Gln Ala Lys Ala Ala Phe Asp Ser Leu
1               5                   10                  15

Thr Ala Gln Ala Thr Glu
            20

<210> SEQ ID NO 303
<211> LENGTH: 22
<212> TYPE: PRT
<213> ORGANISM: Artificial Sequence
<220> FEATURE:
<223> OTHER INFORMATION: Synthetic

<400> SEQUENCE: 303

Ala Asp Gly Glu Ala Thr Ser Gln Ala Lys Val Ala Phe Asp Ser Leu
1               5                   10                  15

Thr Ala Gln Ala Thr Glu
            20

<210> SEQ ID NO 304
<211> LENGTH: 22
<212> TYPE: PRT
<213> ORGANISM: Artificial Sequence
<220> FEATURE:
<223> OTHER INFORMATION: Synthetic

<400> SEQUENCE: 304

Ala Gly Asp Gly Thr Thr Thr Ala Thr Val Leu Thr Gln Ala Ile Ala
1               5                   10                  15

Thr Glu Gly Met Lys Ser
            20

<210> SEQ ID NO 305
<211> LENGTH: 22
<212> TYPE: PRT
<213> ORGANISM: Artificial Sequence
<220> FEATURE:
<223> OTHER INFORMATION: Synthetic

<400> SEQUENCE: 305

Ala Thr Asn Tyr Ala Thr Glu Ala Met Asp Ser Leu Lys Thr Gln Ala
1               5                   10                  15

Ile Asp Leu Ile Ser Gln
            20

<210> SEQ ID NO 306
<211> LENGTH: 22
<212> TYPE: PRT
<213> ORGANISM: Artificial Sequence
<220> FEATURE:
<223> OTHER INFORMATION: Synthetic

<400> SEQUENCE: 306

Ala Thr Pro Leu Pro Ala Phe Thr Val Asp Val Glu Ser Gly Ile Thr

```
1               5                   10                  15
Asp Pro Thr Ser Gly Gln
            20

<210> SEQ ID NO 307
<211> LENGTH: 22
<212> TYPE: PRT
<213> ORGANISM: Artificial Sequence
<220> FEATURE:
<223> OTHER INFORMATION: Synthetic

<400> SEQUENCE: 307

Asp Gly Ser Thr Ser Tyr Thr Leu Asp Thr Leu Asp Ser Leu Lys Thr
1               5                   10                  15

Gln Gly Thr Glu Ile Ile
            20

<210> SEQ ID NO 308
<211> LENGTH: 22
<212> TYPE: PRT
<213> ORGANISM: Artificial Sequence
<220> FEATURE:
<223> OTHER INFORMATION: Synthetic

<400> SEQUENCE: 308

Glu Gly Ser Asp Pro Ala Ala Thr Val Phe Asp Ser Leu Gln Ala Ala
1               5                   10                  15

Lys Ala Arg Gly Thr Glu
            20

<210> SEQ ID NO 309
<211> LENGTH: 22
<212> TYPE: PRT
<213> ORGANISM: Artificial Sequence
<220> FEATURE:
<223> OTHER INFORMATION: Synthetic

<400> SEQUENCE: 309

Gly Thr Ser Thr Thr Ala Phe Tyr Asp Arg Ala Thr Ile Asp Met Asn
1               5                   10                  15

Ala Leu Arg Thr Gln Ala
            20

<210> SEQ ID NO 310
<211> LENGTH: 22
<212> TYPE: PRT
<213> ORGANISM: Artificial Sequence
<220> FEATURE:
<223> OTHER INFORMATION: Synthetic

<400> SEQUENCE: 310

Gly Val Asp Glu Leu Trp Val Arg Arg Gln Phe Val Met His Pro Tyr
1               5                   10                  15

Gly Ile Lys Trp Thr Asp
            20

<210> SEQ ID NO 311
<211> LENGTH: 22
<212> TYPE: PRT
<213> ORGANISM: Artificial Sequence
<220> FEATURE:
<223> OTHER INFORMATION: Synthetic

<400> SEQUENCE: 311
```

-continued

Ile Ile Asp Ala Gly Ala Val Ile Ser Gly Ile Thr Asp Gly Tyr Gln
1               5                   10                  15

Gly Ser Ala Pro Asp Met
            20

<210> SEQ ID NO 312
<211> LENGTH: 22
<212> TYPE: PRT
<213> ORGANISM: Artificial Sequence
<220> FEATURE:
<223> OTHER INFORMATION: Synthetic

<400> SEQUENCE: 312

Ile Ile Glu Ala Gly Thr Val Ile Ser Gly Ile Thr Glu Gly Tyr Gln
1               5                   10                  15

Gly Ser Ser Pro Asp Met
            20

<210> SEQ ID NO 313
<211> LENGTH: 22
<212> TYPE: PRT
<213> ORGANISM: Artificial Sequence
<220> FEATURE:
<223> OTHER INFORMATION: Synthetic

<400> SEQUENCE: 313

Thr Ser Thr Ala Thr Gly Pro Ile Ile Tyr Ala Glu Ala Ile Asn
1               5                   10                  15

Ser Gly Ala Asp Leu Ile
            20

<210> SEQ ID NO 314
<211> LENGTH: 22
<212> TYPE: PRT
<213> ORGANISM: Artificial Sequence
<220> FEATURE:
<223> OTHER INFORMATION: Synthetic

<400> SEQUENCE: 314

Thr Ser Thr Ala Thr Ser Tyr Asp Gly Glu Ala Val Val Thr Ser Leu
1               5                   10                  15

Lys Thr Ser Thr Ala Leu
            20

<210> SEQ ID NO 315
<211> LENGTH: 22
<212> TYPE: PRT
<213> ORGANISM: Artificial Sequence
<220> FEATURE:
<223> OTHER INFORMATION: Synthetic

<400> SEQUENCE: 315

Ala Asp Asp Ala Thr Ser Gln Ala Lys Ala Ala Phe Asp Ser Leu Thr
1               5                   10                  15

Ala Gln Ala Thr Glu Met
            20

<210> SEQ ID NO 316
<211> LENGTH: 23
<212> TYPE: PRT
<213> ORGANISM: Artificial Sequence
<220> FEATURE:
<223> OTHER INFORMATION: Synthetic

<400> SEQUENCE: 316

```
Ala Asp Asp Gly Asp Asp Thr Thr Thr Ala Thr Thr Ser Ala Thr Glu
1               5                   10                  15

Pro Val Ala Ser Ile Lys Thr
            20

<210> SEQ ID NO 317
<211> LENGTH: 23
<212> TYPE: PRT
<213> ORGANISM: Artificial Sequence
<220> FEATURE:
<223> OTHER INFORMATION: Synthetic

<400> SEQUENCE: 317

Ala Asp Ser Ser Thr Asp Tyr Ala Gly Gln Ala Met Asp Ser Leu Leu
1               5                   10                  15

Thr Gln Ala Asn Asp Leu Ile
            20

<210> SEQ ID NO 318
<211> LENGTH: 23
<212> TYPE: PRT
<213> ORGANISM: Artificial Sequence
<220> FEATURE:
<223> OTHER INFORMATION: Synthetic

<400> SEQUENCE: 318

Ala Phe Thr Gln Pro Ile Asp Thr Ser Ala Ile Glu Thr Ala Ile Ile
1               5                   10                  15

Asp Gln Ser Lys Gly Gln Gly
            20

<210> SEQ ID NO 319
<211> LENGTH: 23
<212> TYPE: PRT
<213> ORGANISM: Artificial Sequence
<220> FEATURE:
<223> OTHER INFORMATION: Synthetic

<400> SEQUENCE: 319

Ala Gly Asp Gly Thr Thr Thr Ala Thr Val Leu Ala Tyr Ala Met Val
1               5                   10                  15

Arg Glu Gly Met Lys Asn Leu
            20

<210> SEQ ID NO 320
<211> LENGTH: 23
<212> TYPE: PRT
<213> ORGANISM: Artificial Sequence
<220> FEATURE:
<223> OTHER INFORMATION: Synthetic

<400> SEQUENCE: 320

Ser Thr Gly Gly Thr Asp Tyr Ala Gly Gln Ala Met Asp Ala Leu Leu
1               5                   10                  15

Thr Gln Ala Asn Asp Leu Ile
            20

<210> SEQ ID NO 321
<211> LENGTH: 23
<212> TYPE: PRT
<213> ORGANISM: Artificial Sequence
<220> FEATURE:
<223> OTHER INFORMATION: Synthetic
```

-continued

```
<400> SEQUENCE: 321

Thr Ala Thr Asn Tyr Ala Thr Glu Ala Met Thr Ser Leu Lys Thr Gln
1               5                   10                  15

Ala Thr Asp Leu Ile Ala Gln
            20

<210> SEQ ID NO 322
<211> LENGTH: 24
<212> TYPE: PRT
<213> ORGANISM: Artificial Sequence
<220> FEATURE:
<223> OTHER INFORMATION: Synthetic

<400> SEQUENCE: 322

Ala Gly Asp Gly Thr Thr Thr Ala Thr Val Leu Ala Cys Ser Ile Ala
1               5                   10                  15

Lys Glu Ser Met Asn Ser Ile Lys
            20

<210> SEQ ID NO 323
<211> LENGTH: 24
<212> TYPE: PRT
<213> ORGANISM: Artificial Sequence
<220> FEATURE:
<223> OTHER INFORMATION: Synthetic

<400> SEQUENCE: 323

Ala Lys Gly Asn Asp Asn Val Phe Thr Arg Arg Ala Phe Val Met His
1               5                   10                  15

Pro Tyr Gly Val Lys Trp Thr Asp
            20

<210> SEQ ID NO 324
<211> LENGTH: 24
<212> TYPE: PRT
<213> ORGANISM: Artificial Sequence
<220> FEATURE:
<223> OTHER INFORMATION: Synthetic

<400> SEQUENCE: 324

Ala Asn Asp Gly Thr Ala Thr Ala Thr Ser Ile Glu Thr Gly Ala Thr
1               5                   10                  15

Glu Ala Leu Pro Thr Ser Ala Thr
            20

<210> SEQ ID NO 325
<211> LENGTH: 24
<212> TYPE: PRT
<213> ORGANISM: Artificial Sequence
<220> FEATURE:
<223> OTHER INFORMATION: Synthetic

<400> SEQUENCE: 325

Ala Ser Ser Tyr Ala Asp Glu Ala Lys Ala Ser Leu Lys Thr Ala Gly
1               5                   10                  15

Val Leu Ala Ser Gln Ala Thr Asp
            20

<210> SEQ ID NO 326
<211> LENGTH: 24
<212> TYPE: PRT
<213> ORGANISM: Artificial Sequence
<220> FEATURE:
<223> OTHER INFORMATION: Synthetic
```

-continued

<400> SEQUENCE: 326

Ala Thr Glu Ala Met Asn Leu Trp Ile Arg Glu Lys Thr Gln Glu Ala
1               5                   10                  15

Ile Ala Arg Asp Ala Leu Asp Gln
            20

<210> SEQ ID NO 327
<211> LENGTH: 24
<212> TYPE: PRT
<213> ORGANISM: Artificial Sequence
<220> FEATURE:
<223> OTHER INFORMATION: Synthetic

<400> SEQUENCE: 327

Asp Asp Gly Thr Ala Thr Ser Tyr Ser Val Ala Leu Ser Leu Asn Pro
1               5                   10                  15

Tyr Ser Thr Glu Ala Met Asp Ser
            20

<210> SEQ ID NO 328
<211> LENGTH: 24
<212> TYPE: PRT
<213> ORGANISM: Artificial Sequence
<220> FEATURE:
<223> OTHER INFORMATION: Synthetic

<400> SEQUENCE: 328

Asp Gly Ser Ala Thr Thr Ser Thr Glu Ala Arg Asp Ala Leu Lys
1               5                   10                  15

Ala Glu Ala Thr Thr Leu Glu Asp
            20

<210> SEQ ID NO 329
<211> LENGTH: 24
<212> TYPE: PRT
<213> ORGANISM: Artificial Sequence
<220> FEATURE:
<223> OTHER INFORMATION: Synthetic

<400> SEQUENCE: 329

Asp Asn Pro Ser Lys Ala Ala Tyr Asp Ser Leu Gln Ala Gln Leu Lys
1               5                   10                  15

Arg Asp Ile Glu Ala Ala Glu Tyr
            20

<210> SEQ ID NO 330
<211> LENGTH: 24
<212> TYPE: PRT
<213> ORGANISM: Artificial Sequence
<220> FEATURE:
<223> OTHER INFORMATION: Synthetic

<400> SEQUENCE: 330

Asp Asn Pro Ser Lys Ala Ala Tyr Asp Ser Leu Gln Ala Gln Leu Lys
1               5                   10                  15

Arg Asp Leu Glu Ala Ser Glu Tyr
            20

<210> SEQ ID NO 331
<211> LENGTH: 24
<212> TYPE: PRT
<213> ORGANISM: Artificial Sequence
<220> FEATURE:

<223> OTHER INFORMATION: Synthetic

<400> SEQUENCE: 331

Glu Ala Met Ser Thr Tyr Arg Ala Met Arg Tyr Leu Lys Thr Asp Glu
1               5                   10                  15

Val Ser Thr Asp Leu Ile Glu Gln
            20

<210> SEQ ID NO 332
<211> LENGTH: 24
<212> TYPE: PRT
<213> ORGANISM: Artificial Sequence
<220> FEATURE:
<223> OTHER INFORMATION: Synthetic

<400> SEQUENCE: 332

Met Thr Phe Asn Pro Ala Ala Val Val Ser Pro Leu Leu Leu Gly Asn
1               5                   10                  15

Ala Ser Arg Ile Thr Asn Tyr Ile
            20

<210> SEQ ID NO 333
<211> LENGTH: 24
<212> TYPE: PRT
<213> ORGANISM: Artificial Sequence
<220> FEATURE:
<223> OTHER INFORMATION: Synthetic

<400> SEQUENCE: 333

Ser Leu Pro Ala Phe Ile Glu Val Ile Gly Thr Ser Gly Val Asp Ala
1               5                   10                  15

Ala Ile Lys Gln Tyr Ala Thr Asp
            20

<210> SEQ ID NO 334
<211> LENGTH: 24
<212> TYPE: PRT
<213> ORGANISM: Artificial Sequence
<220> FEATURE:
<223> OTHER INFORMATION: Synthetic

<400> SEQUENCE: 334

Thr Asp Leu Pro Thr Ile Asp Glu Leu Gly Ser Ala Gly Leu Ile Asp
1               5                   10                  15

Thr Ser Thr Val Asp Ser Gln Ile
            20

<210> SEQ ID NO 335
<211> LENGTH: 24
<212> TYPE: PRT
<213> ORGANISM: Artificial Sequence
<220> FEATURE:
<223> OTHER INFORMATION: Synthetic

<400> SEQUENCE: 335

Thr Pro Leu Gln Ala Phe Ser Gly Val Pro Arg Thr Arg Asp Thr Ser
1               5                   10                  15

Glu Ser Pro Ile Thr Asp Gly Glu
            20

<210> SEQ ID NO 336
<211> LENGTH: 24
<212> TYPE: PRT
<213> ORGANISM: Artificial Sequence

```
<220> FEATURE:
<223> OTHER INFORMATION: Synthetic

<400> SEQUENCE: 336

Thr Ser Phe Ala Glu Asp Ala Met Ser Ser Leu Thr Thr Ala Gly Pro
1               5                   10                  15
Thr Thr Ala Thr Asp Leu Leu Asp
            20

<210> SEQ ID NO 337
<211> LENGTH: 24
<212> TYPE: PRT
<213> ORGANISM: Artificial Sequence
<220> FEATURE:
<223> OTHER INFORMATION: Synthetic

<400> SEQUENCE: 337

Thr Ser Met Pro Ala Tyr Thr Ser Lys Ala Leu Val Ile Asp Thr Ser
1               5                   10                  15
Pro Ile Glu Lys Glu Ile Ser Asn
            20

<210> SEQ ID NO 338
<211> LENGTH: 25
<212> TYPE: PRT
<213> ORGANISM: Artificial Sequence
<220> FEATURE:
<223> OTHER INFORMATION: Synthetic

<400> SEQUENCE: 338

Ala Phe Ser Ala Val Leu Asp Thr Ala Val Thr Ala Val Glu Asn Val
1               5                   10                  15
Asn Ala Ala Ile Glu Ala Ile Thr Asp
            20                  25

<210> SEQ ID NO 339
<211> LENGTH: 25
<212> TYPE: PRT
<213> ORGANISM: Artificial Sequence
<220> FEATURE:
<223> OTHER INFORMATION: Synthetic

<400> SEQUENCE: 339

Ala Gly Glu Gly Ala Ser Thr Asp Tyr Ala Gly Gln Ala Met Asp Ser
1               5                   10                  15
Leu Leu Thr Gln Ala Asn Asp Leu Ile
            20                  25

<210> SEQ ID NO 340
<211> LENGTH: 25
<212> TYPE: PRT
<213> ORGANISM: Artificial Sequence
<220> FEATURE:
<223> OTHER INFORMATION: Synthetic

<400> SEQUENCE: 340

Ala Thr Pro Val Phe Val Asp Val Leu Gly Asn Gln Leu Ile Asp Pro
1               5                   10                  15
Asn Ala Ile Glu Lys Ala Ile Thr Asp
            20                  25

<210> SEQ ID NO 341
<211> LENGTH: 25
<212> TYPE: PRT
```

<213> ORGANISM: Artificial Sequence
<220> FEATURE:
<223> OTHER INFORMATION: Synthetic

<400> SEQUENCE: 341

Ala Thr Val Pro Ala Phe Ala Ala Val Val Asp Thr Ala Ala Ile Gln
1               5                   10                  15

Ala Gln Ile Gln Glu Gly Gln Gly Asp
            20                  25

<210> SEQ ID NO 342
<211> LENGTH: 25
<212> TYPE: PRT
<213> ORGANISM: Artificial Sequence
<220> FEATURE:
<223> OTHER INFORMATION: Synthetic

<400> SEQUENCE: 342

Ala Thr Val Pro Ala Phe Ala Ala Val Val Asp Thr Ala Ala Ile Gln
1               5                   10                  15

Thr Gln Ile Gln Glu Gly Gln Ala Asp
            20                  25

<210> SEQ ID NO 343
<211> LENGTH: 25
<212> TYPE: PRT
<213> ORGANISM: Artificial Sequence
<220> FEATURE:
<223> OTHER INFORMATION: Synthetic

<400> SEQUENCE: 343

Asp Gly Thr Ser Ala Ser Thr Val Tyr Val Thr Gly Ala Leu Cys Leu
1               5                   10                  15

Leu Leu Glu Ala Met Pro Gly Leu Lys
            20                  25

<210> SEQ ID NO 344
<211> LENGTH: 25
<212> TYPE: PRT
<213> ORGANISM: Artificial Sequence
<220> FEATURE:
<223> OTHER INFORMATION: Synthetic

<400> SEQUENCE: 344

Glu Asp Val Thr Val Thr Ala Thr Ile Ser Tyr Ala Ala Ser Pro Met
1               5                   10                  15

Asn Gly Gln Val Val Asn Leu Ile Asn
            20                  25

<210> SEQ ID NO 345
<211> LENGTH: 25
<212> TYPE: PRT
<213> ORGANISM: Artificial Sequence
<220> FEATURE:
<223> OTHER INFORMATION: Synthetic

<400> SEQUENCE: 345

Gly Ile Thr Asp Thr Ser Asp Val Ser Leu Val Ala Leu Ser Asp Ala
1               5                   10                  15

Val Glu Ser Ala Ile Thr Glu Thr Gln
            20                  25

<210> SEQ ID NO 346
<211> LENGTH: 25

```
<212> TYPE: PRT
<213> ORGANISM: Artificial Sequence
<220> FEATURE:
<223> OTHER INFORMATION: Synthetic

<400> SEQUENCE: 346

Thr Ser Asn Ser Ala Glu Ser Met Asn Ser Leu Ser Lys His Pro Gln
1               5                   10                  15

Lys Thr Pro Ile Thr Gln Leu Ile Asp
            20                  25

<210> SEQ ID NO 347
<211> LENGTH: 25
<212> TYPE: PRT
<213> ORGANISM: Artificial Sequence
<220> FEATURE:
<223> OTHER INFORMATION: Synthetic

<400> SEQUENCE: 347

Ala Glu Pro Asn Ala Ala Thr Asn Tyr Ala Thr Glu Ala Met Asp Ser
1               5                   10                  15

Leu Lys Thr Gln Ala Ile Asp Leu Ile
            20                  25

<210> SEQ ID NO 348
<211> LENGTH: 26
<212> TYPE: PRT
<213> ORGANISM: Artificial Sequence
<220> FEATURE:
<223> OTHER INFORMATION: Synthetic

<400> SEQUENCE: 348

Ala Thr Ser Ser Pro Ser Tyr Ala Val Ile Asp Val Thr Ala Val Thr
1               5                   10                  15

Thr Gly Ile Thr Asp Ala Gln Thr Ala Met
            20                  25

<210> SEQ ID NO 349
<211> LENGTH: 26
<212> TYPE: PRT
<213> ORGANISM: Artificial Sequence
<220> FEATURE:
<223> OTHER INFORMATION: Synthetic

<400> SEQUENCE: 349

Asp Asp Gly Thr Val Ser Arg Phe Ala Glu Asp His Phe Leu Ile Thr
1               5                   10                  15

Thr Thr Thr Ala Tyr Ala Thr Glu Ala Met
            20                  25

<210> SEQ ID NO 350
<211> LENGTH: 26
<212> TYPE: PRT
<213> ORGANISM: Artificial Sequence
<220> FEATURE:
<223> OTHER INFORMATION: Synthetic

<400> SEQUENCE: 350

Ser Leu Phe Gly Pro Val Phe Ala Gly Ile Ile Thr Ala Ala Val Leu
1               5                   10                  15

Ser Ala Ile Met Ser Thr Ala Asp Ser Gln
            20                  25

<210> SEQ ID NO 351
```

```
<211> LENGTH: 27
<212> TYPE: PRT
<213> ORGANISM: Artificial Sequence
<220> FEATURE:
<223> OTHER INFORMATION: Synthetic

<400> SEQUENCE: 351

Ala Ala Asp Gly Ala Thr Gly Ser Thr Asp Tyr Ala Gly Gln Ala Met
1               5                   10                  15

Asp Ser Leu Leu Thr Gln Ala Asn Asp Leu Ile
            20                  25

<210> SEQ ID NO 352
<211> LENGTH: 27
<212> TYPE: PRT
<213> ORGANISM: Artificial Sequence
<220> FEATURE:
<223> OTHER INFORMATION: Synthetic

<400> SEQUENCE: 352

Ala Ala Asp Gly Ala Thr Thr Asp Tyr Ala Thr Asp Ala Phe Ala Thr
1               5                   10                  15

Leu Lys Thr Thr Ala Thr Asp Met Ile Glu Gln
            20                  25

<210> SEQ ID NO 353
<211> LENGTH: 27
<212> TYPE: PRT
<213> ORGANISM: Artificial Sequence
<220> FEATURE:
<223> OTHER INFORMATION: Synthetic

<400> SEQUENCE: 353

Ala Ala Asp Gly Ser Thr Gly Gly Ala Asp Tyr Ala Gly Gln Ala Met
1               5                   10                  15

Asp Ala Leu Leu Thr Gln Ala Asn Asp Leu Ile
            20                  25

<210> SEQ ID NO 354
<211> LENGTH: 27
<212> TYPE: PRT
<213> ORGANISM: Artificial Sequence
<220> FEATURE:
<223> OTHER INFORMATION: Synthetic

<400> SEQUENCE: 354

Ala Ala Glu Gly Ala Thr Gly Gly Thr Asp Tyr Ala Gly Gln Ala Met
1               5                   10                  15

Asp Ala Leu Leu Thr Gln Ala Asn Asp Leu Ile
            20                  25

<210> SEQ ID NO 355
<211> LENGTH: 27
<212> TYPE: PRT
<213> ORGANISM: Artificial Sequence
<220> FEATURE:
<223> OTHER INFORMATION: Synthetic

<400> SEQUENCE: 355

Ala Ala Glu Gly Ala Thr Gly Ser Thr Asp Tyr Ala Gly Lys Ala Met
1               5                   10                  15

Asp Ser Leu Leu Thr Gln Ala Asn Asp Leu Ile
            20                  25
```

```
<210> SEQ ID NO 356
<211> LENGTH: 27
<212> TYPE: PRT
<213> ORGANISM: Artificial Sequence
<220> FEATURE:
<223> OTHER INFORMATION: Synthetic

<400> SEQUENCE: 356

Ala Ala Glu Gly Ala Thr Gly Ser Thr Asp Tyr Ala Gly Gln Ala Met
1               5                   10                  15

Asp Ser Leu Leu Thr Gln Ala Asn Asp Leu Ile
            20                  25

<210> SEQ ID NO 357
<211> LENGTH: 27
<212> TYPE: PRT
<213> ORGANISM: Artificial Sequence
<220> FEATURE:
<223> OTHER INFORMATION: Synthetic

<400> SEQUENCE: 357

Ala Glu Gly Gly Ala Ala Thr Thr Pro Asp Tyr Ala Gly Gln Ala Met
1               5                   10                  15

Asp Ser Leu Leu Thr Gln Ala Asn Thr Leu Ile
            20                  25

<210> SEQ ID NO 358
<211> LENGTH: 27
<212> TYPE: PRT
<213> ORGANISM: Artificial Sequence
<220> FEATURE:
<223> OTHER INFORMATION: Synthetic

<400> SEQUENCE: 358

Ala Glu Pro Asp Glu Glu Ala Lys Ala Met Phe Asp Ser Leu Ala Lys
1               5                   10                  15

Pro Ala Leu Gly Pro Gly Ala Ser Ala Thr Glu
            20                  25

<210> SEQ ID NO 359
<211> LENGTH: 27
<212> TYPE: PRT
<213> ORGANISM: Artificial Sequence
<220> FEATURE:
<223> OTHER INFORMATION: Synthetic

<400> SEQUENCE: 359

Ala Glu Pro Asp Glu Glu Ala Lys Ala Met Phe Glu Ser Leu Ala Lys
1               5                   10                  15

Pro Ala Leu Gly Pro Gly Ala Ser Ala Thr Asp
            20                  25

<210> SEQ ID NO 360
<211> LENGTH: 27
<212> TYPE: PRT
<213> ORGANISM: Artificial Sequence
<220> FEATURE:
<223> OTHER INFORMATION: Synthetic

<400> SEQUENCE: 360

Ala Phe Thr Gly Thr Ile Asp Val Asp Ser Ala Ala Glu Ser Leu Lys
1               5                   10                  15

Leu Phe Thr Lys Thr Phe Ala Ile Thr Asp Gly
            20                  25
```

```
<210> SEQ ID NO 361
<211> LENGTH: 27
<212> TYPE: PRT
<213> ORGANISM: Artificial Sequence
<220> FEATURE:
<223> OTHER INFORMATION: Synthetic

<400> SEQUENCE: 361

Ala Thr Ala Leu Pro Ala Trp Ala Ala Val Ile Asp Thr Thr Glu Val
1               5                   10                  15

Gln Ala Thr Phe Gly Glu Ala Lys Gly Asp Met
            20                  25

<210> SEQ ID NO 362
<211> LENGTH: 27
<212> TYPE: PRT
<213> ORGANISM: Artificial Sequence
<220> FEATURE:
<223> OTHER INFORMATION: Synthetic

<400> SEQUENCE: 362

Ala Thr Ser Leu Pro Ala Phe Ala Gly Val Ile Asp Thr Ser Ala Val
1               5                   10                  15

Glu Ala Ala Ile Thr Asp Gly Lys Gly Asp Met
            20                  25

<210> SEQ ID NO 363
<211> LENGTH: 27
<212> TYPE: PRT
<213> ORGANISM: Artificial Sequence
<220> FEATURE:
<223> OTHER INFORMATION: Synthetic

<400> SEQUENCE: 363

Ala Thr Ser Leu Pro Ala Phe Ala Gly Val Ile Gly Ala Val Ala Leu
1               5                   10                  15

Ala Leu Ala Val Gly Asp Gly Asp Met Lys Ala
            20                  25

<210> SEQ ID NO 364
<211> LENGTH: 27
<212> TYPE: PRT
<213> ORGANISM: Artificial Sequence
<220> FEATURE:
<223> OTHER INFORMATION: Synthetic

<400> SEQUENCE: 364

Ala Thr Thr Leu Pro Ala Val Ala Thr Arg Ala Gly Asp Thr Trp Ala
1               5                   10                  15

Val Glu Val Arg Ile Ser Asp Gly Glu Asp Met
            20                  25

<210> SEQ ID NO 365
<211> LENGTH: 27
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (14)..(14)
<223> OTHER INFORMATION: Xaa can be any naturally occurring amino acid

<400> SEQUENCE: 365

Thr Ser Val Pro Ala Phe Ala Ala Ser Val Ile Asp Thr Xaa Ala Val
```

```
                1               5                   10                  15
Glu Gln Ala Ile Thr Asp Gly Lys Ser Asp Met
                20                  25
```

<210> SEQ ID NO 366
<211> LENGTH: 27
<212> TYPE: PRT
<213> ORGANISM: Artificial Sequence
<220> FEATURE:
<223> OTHER INFORMATION: Synthetic

<400> SEQUENCE: 366

```
Thr Ser Val Pro Ala Phe Ala Gly Ser Val Ile Asp Thr Ser Ala Val
1               5                   10                  15

Glu Thr Ala Ile Thr Asp Gly Lys Ser Asp Met
                20                  25
```

<210> SEQ ID NO 367
<211> LENGTH: 28
<212> TYPE: PRT
<213> ORGANISM: Artificial Sequence
<220> FEATURE:
<223> OTHER INFORMATION: Synthetic

<400> SEQUENCE: 367

```
Ala Asp Asp Gly Thr Ser Thr His Ile Ser Tyr Met Gln Leu His Gly
1               5                   10                  15

Arg Val Cys Arg Phe Ala Asn Ala Leu Lys Ala Gln
                20                  25
```

<210> SEQ ID NO 368
<211> LENGTH: 28
<212> TYPE: PRT
<213> ORGANISM: Artificial Sequence
<220> FEATURE:
<223> OTHER INFORMATION: Synthetic

<400> SEQUENCE: 368

```
Ala Phe Ala Asn Asp Asp Ala Ile Asp Thr Ala Val Gly Thr Ala Gln
1               5                   10                  15

Asn Val Thr Asp Thr Trp Leu Ala Gln Gly Asp Met
                20                  25
```

<210> SEQ ID NO 369
<211> LENGTH: 28
<212> TYPE: PRT
<213> ORGANISM: Artificial Sequence
<220> FEATURE:
<223> OTHER INFORMATION: Synthetic

<400> SEQUENCE: 369

```
Ala Ser Ser Met Pro Val Trp Ala Ala Ser Val Ile Asp Thr Ser Ser
1               5                   10                  15

Val Glu Gln Ala Ile Thr Asp Gly Lys Gly Asp Met
                20                  25
```

<210> SEQ ID NO 370
<211> LENGTH: 28
<212> TYPE: PRT
<213> ORGANISM: Artificial Sequence
<220> FEATURE:
<223> OTHER INFORMATION: Synthetic

<400> SEQUENCE: 370

```
Ala Ser Ser Val Pro Ala Trp Ala Gly Ser Val Ile Asp Thr Ser Ala
1               5                   10                  15

Val Glu Ser Ala Ile Ser Asp Gly Lys Gln Asp Met
            20                  25
```

<210> SEQ ID NO 371
<211> LENGTH: 28
<212> TYPE: PRT
<213> ORGANISM: Artificial Sequence
<220> FEATURE:
<223> OTHER INFORMATION: Synthetic

<400> SEQUENCE: 371

```
Ala Thr Ser Leu Pro Ala Phe Ala Gly Val Ile Asp Thr Ser Ala Val
1               5                   10                  15

Glu Thr Ala Met Thr Asp Gly Gln Gly Asp Met Lys
            20                  25
```

<210> SEQ ID NO 372
<211> LENGTH: 28
<212> TYPE: PRT
<213> ORGANISM: Artificial Sequence
<220> FEATURE:
<223> OTHER INFORMATION: Synthetic

<400> SEQUENCE: 372

```
Thr Ala Leu Pro Val Ile Glu Thr Ala Ala Gly Asp Val Ser Ala Phe
1               5                   10                  15

Val Pro Thr Asn Val Ile Ser Ile Thr Asp Gly Gln
            20                  25
```

<210> SEQ ID NO 373
<211> LENGTH: 28
<212> TYPE: PRT
<213> ORGANISM: Artificial Sequence
<220> FEATURE:
<223> OTHER INFORMATION: Synthetic

<400> SEQUENCE: 373

```
Thr Ser Leu Pro Val Ile Glu Thr Gln Ala Gly Asp Val Ser Ala Tyr
1               5                   10                  15

Ile Pro Thr Asn Val Ile Ser Ile Thr Asp Gly Gln
            20                  25
```

<210> SEQ ID NO 374
<211> LENGTH: 29
<212> TYPE: PRT
<213> ORGANISM: Artificial Sequence
<220> FEATURE:
<223> OTHER INFORMATION: Synthetic

<400> SEQUENCE: 374

```
Ala Glu Asp Pro Ala Met Gln Gln Arg Ser Val Ala Ala Phe Asp Ala
1               5                   10                  15

Leu Gln Leu Ser Ala Thr Asp Ala Glu Leu Arg Glu Tyr
            20                  25
```

<210> SEQ ID NO 375
<211> LENGTH: 29
<212> TYPE: PRT
<213> ORGANISM: Artificial Sequence
<220> FEATURE:
<223> OTHER INFORMATION: Synthetic

<400> SEQUENCE: 375

Ala Glu Asp Pro Ala Met Gln Gln Arg Ser Val Ala Ala Phe Asp Ala
1               5                   10                  15

Leu Gln Gln Ser Ala Thr Asp Ala Glu Leu Arg Glu Tyr
            20                  25

<210> SEQ ID NO 376
<211> LENGTH: 29
<212> TYPE: PRT
<213> ORGANISM: Artificial Sequence
<220> FEATURE:
<223> OTHER INFORMATION: Synthetic

<400> SEQUENCE: 376

Ala Glu Asp Pro Ala Met Gln Gln Arg Ser Val Ala Ala Phe Glu Ala
1               5                   10                  15

Leu Gln Glu Ser Ala Thr Asp Ala Gly Leu Arg Glu Tyr
            20                  25

<210> SEQ ID NO 377
<211> LENGTH: 29
<212> TYPE: PRT
<213> ORGANISM: Artificial Sequence
<220> FEATURE:
<223> OTHER INFORMATION: Synthetic

<400> SEQUENCE: 377

Ala Ser Thr Leu Pro Ala Ile Ala Thr Arg Ala Gly Asp Val Trp Thr
1               5                   10                  15

Val Glu Val Arg Ile Thr Asp Gly Glu Asp Met Ser Ala
            20                  25

<210> SEQ ID NO 378
<211> LENGTH: 29
<212> TYPE: PRT
<213> ORGANISM: Artificial Sequence
<220> FEATURE:
<223> OTHER INFORMATION: Synthetic

<400> SEQUENCE: 378

Asp Phe Asn Ile Ala Pro Gly Leu Ala Pro Leu Asn Gly Leu Leu Leu
1               5                   10                  15

Pro Ser Glu Val Val Ser Gln Ile Ser Ser Phe Ile Gln
            20                  25

<210> SEQ ID NO 379
<211> LENGTH: 29
<212> TYPE: PRT
<213> ORGANISM: Artificial Sequence
<220> FEATURE:
<223> OTHER INFORMATION: Synthetic

<400> SEQUENCE: 379

Ser Thr Thr Thr Ser Tyr Ser Ser Glu Leu Ser Val Tyr Pro Ser Leu
1               5                   10                  15

Asn Ser Leu Lys Glu Thr His Gly Gln Asp Leu Ile Asp
            20                  25

<210> SEQ ID NO 380
<211> LENGTH: 29
<212> TYPE: PRT
<213> ORGANISM: Artificial Sequence
<220> FEATURE:
<223> OTHER INFORMATION: Synthetic

```
<400> SEQUENCE: 380

Ala Thr Ser Leu Pro Ala Phe Ala Gly Val Ile Asp Thr Ser Ala Val
1               5                   10                  15

Glu Ser Ala Ile Thr Asp Gly Gln Gly Asp Met Lys Ala
            20                  25

<210> SEQ ID NO 381
<211> LENGTH: 29
<212> TYPE: PRT
<213> ORGANISM: Artificial Sequence
<220> FEATURE:
<223> OTHER INFORMATION: Synthetic

<400> SEQUENCE: 381

Ala Asp Asp Gly Thr Ser Thr Ala Thr Ser Tyr Ala Thr Glu Ala Met
1               5                   10                  15

Asn Ser Leu Lys Thr Gln Ala Thr Asp Leu Ile Asp Gln
            20                  25

<210> SEQ ID NO 382
<211> LENGTH: 30
<212> TYPE: PRT
<213> ORGANISM: Artificial Sequence
<220> FEATURE:
<223> OTHER INFORMATION: Synthetic

<400> SEQUENCE: 382

Ala Asp Asp Gly Gly Ser Thr Ile Thr Ser Tyr Thr Val Glu Tyr Ala
1               5                   10                  15

Thr Ser Asn Ser Gly Pro Trp Thr Thr His Ser Thr Asn Leu
            20                  25                  30

<210> SEQ ID NO 383
<211> LENGTH: 31
<212> TYPE: PRT
<213> ORGANISM: Artificial Sequence
<220> FEATURE:
<223> OTHER INFORMATION: Synthetic

<400> SEQUENCE: 383

Met Phe Asn Pro Ser Glu Val Ala Asp Asn Leu Lys Arg Ser Gly Ala
1               5                   10                  15

Phe Val Pro Gly Ile Arg Pro Gly Gln Gln Thr Ala Asn Tyr Ile
            20                  25                  30

<210> SEQ ID NO 384
<211> LENGTH: 32
<212> TYPE: PRT
<213> ORGANISM: Artificial Sequence
<220> FEATURE:
<223> OTHER INFORMATION: Synthetic

<400> SEQUENCE: 384

Asp His Leu Glu Thr Arg Leu Ala Phe Asn Tyr His Pro Phe Gly His
1               5                   10                  15

Thr Tyr Ile Ser Ala Ile Leu Asp Ala Asn Asp Phe Thr Pro Thr Ser
            20                  25                  30

<210> SEQ ID NO 385
<211> LENGTH: 33
<212> TYPE: PRT
<213> ORGANISM: Artificial Sequence
<220> FEATURE:
<223> OTHER INFORMATION: Synthetic
```

```
<400> SEQUENCE: 385

Ala Gly Asp Gly Thr Thr Thr Ala Thr Ile Tyr Ala Glu Ala Ile Phe
1               5                   10                  15

Asn Glu Gly Leu Lys Asn Val Val Ala Gly Ala Asp Ala Met Ser Leu
            20                  25                  30

Lys

<210> SEQ ID NO 386
<211> LENGTH: 35
<212> TYPE: PRT
<213> ORGANISM: Artificial Sequence
<220> FEATURE:
<223> OTHER INFORMATION: Synthetic

<400> SEQUENCE: 386

Gly Asp Asp Ile Leu Ile Asn Arg Gln Ala Phe Val Leu His Pro Arg
1               5                   10                  15

Gly Val Glu Phe Lys Asn Ala Ser Val Ala Gly Ala Thr Pro Ser Asn
            20                  25                  30

Ala Glu Val
        35

<210> SEQ ID NO 387
<211> LENGTH: 35
<212> TYPE: PRT
<213> ORGANISM: Artificial Sequence
<220> FEATURE:
<223> OTHER INFORMATION: Synthetic

<400> SEQUENCE: 387

Gly Asp Asp Ile Leu Ile Asn Arg Gln His Phe Ile Leu His Pro Arg
1               5                   10                  15

Gly Val Lys Phe Lys Asn Thr Ser Val Ala Gly Ser Ser Pro Thr Asn
            20                  25                  30

Ala Glu Leu
        35

<210> SEQ ID NO 388
<211> LENGTH: 35
<212> TYPE: PRT
<213> ORGANISM: Artificial Sequence
<220> FEATURE:
<223> OTHER INFORMATION: Synthetic

<400> SEQUENCE: 388

Gly Asp Asp Ile Leu Ile Asn Arg Gln His Phe Leu Leu His Pro Arg
1               5                   10                  15

Gly Val Lys Phe Asn Asn Ala Ala Val Ala Gly Ser Ser Pro Thr Asn
            20                  25                  30

Ala Glu Leu
        35

<210> SEQ ID NO 389
<211> LENGTH: 35
<212> TYPE: PRT
<213> ORGANISM: Artificial Sequence
<220> FEATURE:
<223> OTHER INFORMATION: Synthetic

<400> SEQUENCE: 389

Gly Asp Asp Ile Leu Ile Asn Arg Gln His Phe Leu Leu His Pro Arg
```

```
                1               5                  10                  15
Gly Val Lys Phe Thr Asp Lys Ser Val Ala Gly Asn Ser Pro Thr Asn
                20                  25                  30

Ala Glu Leu
        35

<210> SEQ ID NO 390
<211> LENGTH: 35
<212> TYPE: PRT
<213> ORGANISM: Artificial Sequence
<220> FEATURE:
<223> OTHER INFORMATION: Synthetic

<400> SEQUENCE: 390

Gly Asp Asp Ile Leu Ile Asn Arg Gln His Phe Leu Leu His Pro Arg
1               5                  10                  15

Gly Val Lys Phe Thr Asp Lys Ser Val Ser Gly Ser Ser Pro Thr Asn
                20                  25                  30

Ala Glu Leu
        35

<210> SEQ ID NO 391
<211> LENGTH: 35
<212> TYPE: PRT
<213> ORGANISM: Artificial Sequence
<220> FEATURE:
<223> OTHER INFORMATION: Synthetic

<400> SEQUENCE: 391

Gly Asp Asp Ile Leu Ile Asn Arg Gln His Phe Leu Leu His Pro Arg
1               5                  10                  15

Gly Val Lys Phe Thr Asn Lys Ser Val Ala Gly Ser Ser Pro Thr Asn
                20                  25                  30

Ala Glu Leu
        35

<210> SEQ ID NO 392
<211> LENGTH: 35
<212> TYPE: PRT
<213> ORGANISM: Artificial Sequence
<220> FEATURE:
<223> OTHER INFORMATION: Synthetic

<400> SEQUENCE: 392

Gly Asp Asp Ile Leu Val Asn Arg Gln His Phe Leu Leu His Pro Arg
1               5                  10                  15

Gly Val Lys Phe Thr Asn Lys Thr Val Thr Gly Ser Ser Pro Thr Asn
                20                  25                  30

Ala Glu Leu
        35

<210> SEQ ID NO 393
<211> LENGTH: 35
<212> TYPE: PRT
<213> ORGANISM: Artificial Sequence
<220> FEATURE:
<223> OTHER INFORMATION: Synthetic

<400> SEQUENCE: 393

Gly Asp Asp Ile Leu Val Asn Arg Arg His Phe Val Leu His Pro Arg
1               5                  10                  15

Gly Ile Lys Phe Thr Asn Ala Ser Val Ala Gly Val Ser Pro Thr Asn
```

```
Ala Glu Leu
        35

<210> SEQ ID NO 394
<211> LENGTH: 35
<212> TYPE: PRT
<213> ORGANISM: Artificial Sequence
<220> FEATURE:
<223> OTHER INFORMATION: Synthetic

<400> SEQUENCE: 394

Gly Glu Asp Ile Leu Ile Asn Arg Lys His Phe Val Leu His Pro Arg
1               5                   10                  15

Gly Ile Lys Phe Thr Asn Ala Ser Val Ala Lys Thr Ala Pro Thr Asn
            20                  25                  30

Ala Glu Leu
        35

<210> SEQ ID NO 395
<211> LENGTH: 35
<212> TYPE: PRT
<213> ORGANISM: Artificial Sequence
<220> FEATURE:
<223> OTHER INFORMATION: Synthetic

<400> SEQUENCE: 395

Gly Glu Asp Ile Leu Ile Asn Arg Lys His Phe Val Leu His Pro Arg
1               5                   10                  15

Gly Ile Lys Phe Thr Asn Ala Thr Val Ala Lys Thr Ala Pro Thr Asn
            20                  25                  30

Ala Glu Leu
        35

<210> SEQ ID NO 396
<211> LENGTH: 35
<212> TYPE: PRT
<213> ORGANISM: Artificial Sequence
<220> FEATURE:
<223> OTHER INFORMATION: Synthetic

<400> SEQUENCE: 396

Gly Glu Asp Ile Leu Ile Asn Arg Gln His Phe Val Leu His Pro Arg
1               5                   10                  15

Gly Val Ala Phe Gln Asn Ala Ser Val Ala Gly Ser Ser Pro Thr Asn
            20                  25                  30

Ala Glu Leu
        35

<210> SEQ ID NO 397
<211> LENGTH: 35
<212> TYPE: PRT
<213> ORGANISM: Artificial Sequence
<220> FEATURE:
<223> OTHER INFORMATION: Synthetic

<400> SEQUENCE: 397

Gly Glu Asp Tyr Leu Ile Asn Arg Arg Thr Phe Ile Leu His Pro Arg
1               5                   10                  15

Gly Val Arg Phe Thr Ser Gly Ser Val Ala Gly Val Ser Pro Thr Asn
            20                  25                  30

Ala Glu Leu
```

<210> SEQ ID NO 398
<211> LENGTH: 35
<212> TYPE: PRT
<213> ORGANISM: Artificial Sequence
<220> FEATURE:
<223> OTHER INFORMATION: Synthetic

<400> SEQUENCE: 398

Gly Gly Asp Ile Leu Tyr Thr Arg Arg Gln Phe Val Leu His Pro Tyr
1               5                   10                  15

Gly Ile Ala Trp Gln Asp Ala Ser Val Ala Ala Glu Phe Pro Thr Asn
            20                  25                  30

Val Glu Leu
        35

<210> SEQ ID NO 399
<211> LENGTH: 35
<212> TYPE: PRT
<213> ORGANISM: Artificial Sequence
<220> FEATURE:
<223> OTHER INFORMATION: Synthetic

<400> SEQUENCE: 399

Gly Gly Asp Ile Leu Tyr Thr Arg Arg Gln Phe Val Leu His Pro Tyr
1               5                   10                  15

Gly Ile Lys Trp Thr Asp Ala Ser Val Ala Gly Glu Phe Pro Thr Thr
            20                  25                  30

Ala Glu Met
        35

<210> SEQ ID NO 400
<211> LENGTH: 35
<212> TYPE: PRT
<213> ORGANISM: Artificial Sequence
<220> FEATURE:
<223> OTHER INFORMATION: Synthetic

<400> SEQUENCE: 400

Gly Asn Asp Lys Leu Tyr Thr Arg Arg Ala Ile Val Met His Pro Tyr
1               5                   10                  15

Gly Leu Ser Phe Glu Pro Glu Leu Ser Asp Phe Thr Pro Thr Asn
            20                  25                  30

Gly Asp Leu
        35

<210> SEQ ID NO 401
<211> LENGTH: 35
<212> TYPE: PRT
<213> ORGANISM: Artificial Sequence
<220> FEATURE:
<223> OTHER INFORMATION: Synthetic

<400> SEQUENCE: 401

Gly Val Asp Tyr Leu Ile Thr Arg Arg His Phe Leu Leu His Pro Arg
1               5                   10                  15

Gly Ile Lys Phe Thr Asn Ser Ser Val Ala Gly Ala Ala Pro Thr Asn
            20                  25                  30

Ala Glu Leu
        35

-continued

```
<210> SEQ ID NO 402
<211> LENGTH: 36
<212> TYPE: PRT
<213> ORGANISM: Artificial Sequence
<220> FEATURE:
<223> OTHER INFORMATION: Synthetic

<400> SEQUENCE: 402

Gly Ile Asp Tyr Leu Ile Asn Arg Lys Thr Phe Ile Leu His Pro Arg
1               5                   10                  15

Gly Val Lys Phe Thr Asn Thr Val Arg Ala Asn Thr Glu Thr Val Ser
            20                  25                  30

Arg Ala Glu Leu
        35

<210> SEQ ID NO 403
<211> LENGTH: 36
<212> TYPE: PRT
<213> ORGANISM: Artificial Sequence
<220> FEATURE:
<223> OTHER INFORMATION: Synthetic

<400> SEQUENCE: 403

Gly Val Asp Tyr Leu Ile Asn Arg Lys Ala Phe Ile Leu His Pro Arg
1               5                   10                  15

Gly Ile Ala Tyr Thr Gly Ala Lys Arg Gly His Val Glu Thr Pro Thr
            20                  25                  30

Arg Ala Glu Leu
        35

<210> SEQ ID NO 404
<211> LENGTH: 36
<212> TYPE: PRT
<213> ORGANISM: Artificial Sequence
<220> FEATURE:
<223> OTHER INFORMATION: Synthetic

<400> SEQUENCE: 404

Gly Val Asp Tyr Leu Ile Asn Arg Lys Thr Phe Ile Leu His Pro Arg
1               5                   10                  15

Gly Ile Lys Phe Thr Gly Ala Val Arg Ala Asn Gln Glu Thr Val Ser
            20                  25                  30

Arg Ala Glu Leu
        35

<210> SEQ ID NO 405
<211> LENGTH: 36
<212> TYPE: PRT
<213> ORGANISM: Artificial Sequence
<220> FEATURE:
<223> OTHER INFORMATION: Synthetic

<400> SEQUENCE: 405

Gln Gly Asp Asp Ile Leu Ile Asn Arg Gln His Phe Ile Leu His Pro
1               5                   10                  15

Arg Gly Val Glu Phe Lys Asn Ala Ala Val Ala Gly Pro Ser Pro Thr
            20                  25                  30

Asn Ala Glu Leu
        35

<210> SEQ ID NO 406
<211> LENGTH: 36
<212> TYPE: PRT
```

```
-continued

<213> ORGANISM: Artificial Sequence
<220> FEATURE:
<223> OTHER INFORMATION: Synthetic

<400> SEQUENCE: 406

Gln Gly Asp Asp Ile Leu Ile Asn Arg Gln His Phe Ile Leu His Pro
1               5                   10                  15

Arg Gly Val Glu Phe Lys Asn Ala Ala Val Ala Ser Ser Ser Pro Thr
            20                  25                  30

Asn Thr Glu Leu
        35

<210> SEQ ID NO 407
<211> LENGTH: 37
<212> TYPE: PRT
<213> ORGANISM: Artificial Sequence
<220> FEATURE:
<223> OTHER INFORMATION: Synthetic

<400> SEQUENCE: 407

Ala Ala Gly Ile Asp Glu Ile Phe Thr Arg Arg Ala Phe Val Tyr His
1               5                   10                  15

Pro Tyr Gly Val Lys Phe Thr Ser Lys Ala Val Ala Gly Leu Thr Pro
            20                  25                  30

Ser Asn Ala Glu Leu
        35

<210> SEQ ID NO 408
<211> LENGTH: 37
<212> TYPE: PRT
<213> ORGANISM: Artificial Sequence
<220> FEATURE:
<223> OTHER INFORMATION: Synthetic

<400> SEQUENCE: 408

Ala Ala Gly Asn Asp Arg Ile Phe Thr Arg Arg Ala Leu Val Met His
1               5                   10                  15

Pro Tyr Gly Ile Lys Trp Thr Asp Thr Ser Val Glu Gly Ala Thr Pro
            20                  25                  30

Ser Asn Glu Glu Leu
        35

<210> SEQ ID NO 409
<211> LENGTH: 37
<212> TYPE: PRT
<213> ORGANISM: Artificial Sequence
<220> FEATURE:
<223> OTHER INFORMATION: Synthetic

<400> SEQUENCE: 409

Ala Ala Gly Asn Asp Arg Val Phe Thr Arg Arg Ala Phe Thr Met His
1               5                   10                  15

Pro Tyr Gly Val Lys Phe Lys Ser Thr Thr Val Ala Gly Ala Thr Pro
            20                  25                  30

Ser Asn Ala Glu Met
        35

<210> SEQ ID NO 410
<211> LENGTH: 37
<212> TYPE: PRT
<213> ORGANISM: Artificial Sequence
<220> FEATURE:
<223> OTHER INFORMATION: Synthetic
```

<400> SEQUENCE: 410

Ala Ala Gly Val Asp Glu Leu Phe Thr Arg Arg Ala Phe Val Tyr His
1               5                   10                  15

Pro Tyr Gly Val Lys Phe Thr Ser Lys Ala Val Ala Gly Leu Thr Pro
            20                  25                  30

Ser Asn Thr Glu Leu
        35

<210> SEQ ID NO 411
<211> LENGTH: 37
<212> TYPE: PRT
<213> ORGANISM: Artificial Sequence
<220> FEATURE:
<223> OTHER INFORMATION: Synthetic

<400> SEQUENCE: 411

Ala Ala Gly Val Asp Glu Val Phe Thr Arg Arg Ala Phe Val Phe His
1               5                   10                  15

Pro Tyr Gly Val Lys Phe Thr Asp Thr Val Ala Gly Leu Thr Pro
            20                  25                  30

Ser Asn Thr Glu Leu
        35

<210> SEQ ID NO 412
<211> LENGTH: 37
<212> TYPE: PRT
<213> ORGANISM: Artificial Sequence
<220> FEATURE:
<223> OTHER INFORMATION: Synthetic

<400> SEQUENCE: 412

Ala Ala Gly Val Asp Glu Val Phe Thr Arg Arg Ala Phe Val Tyr His
1               5                   10                  15

Pro Tyr Gly Ile Lys Phe Lys Ser Thr Thr Val Thr Gly Glu Thr Pro
            20                  25                  30

Ser Asn Ala Glu Leu
        35

<210> SEQ ID NO 413
<211> LENGTH: 37
<212> TYPE: PRT
<213> ORGANISM: Artificial Sequence
<220> FEATURE:
<223> OTHER INFORMATION: Synthetic

<400> SEQUENCE: 413

Ala Ala Gly Val Asp Glu Val Tyr Thr Arg Arg Ala Phe Val Phe His
1               5                   10                  15

Pro Tyr Gly Ile Lys Phe Thr Asp Thr Thr Val Ala Gly Glu Thr Pro
            20                  25                  30

Ser Asn Ala Glu Leu
        35

<210> SEQ ID NO 414
<211> LENGTH: 37
<212> TYPE: PRT
<213> ORGANISM: Artificial Sequence
<220> FEATURE:
<223> OTHER INFORMATION: Synthetic

<400> SEQUENCE: 414

```
Ala Ala Gly Val Asp Asn Val Tyr Thr Arg Arg Ala Leu Thr Met His
1               5                   10                  15

Pro Tyr Gly Val Arg Trp Gln Asp Asn Ser Ile Val Gly Leu Thr Pro
            20                  25                  30

Ser Asn Ala Glu Leu
        35

<210> SEQ ID NO 415
<211> LENGTH: 37
<212> TYPE: PRT
<213> ORGANISM: Artificial Sequence
<220> FEATURE:
<223> OTHER INFORMATION: Synthetic

<400> SEQUENCE: 415

Gly Gln Asp Tyr Leu Val Thr Arg Arg His Tyr Val Leu His Pro Arg
1               5                   10                  15

Gly Ile Lys Trp Asp Pro Gly Ser Gly Val Pro Ala Ser Val Thr Pro
            20                  25                  30

Ser Asp Ala Glu Leu
        35

<210> SEQ ID NO 416
<211> LENGTH: 37
<212> TYPE: PRT
<213> ORGANISM: Artificial Sequence
<220> FEATURE:
<223> OTHER INFORMATION: Synthetic

<400> SEQUENCE: 416

Ser Lys Gly Ile Asp Glu Val Tyr Thr Arg Arg Ala Phe Val Phe His
1               5                   10                  15

Pro Tyr Gly Val Lys Phe Thr Asp Ala Thr Val Ser Gly Glu Thr Pro
            20                  25                  30

Ser Asn Ala Glu Leu
        35

<210> SEQ ID NO 417
<211> LENGTH: 37
<212> TYPE: PRT
<213> ORGANISM: Artificial Sequence
<220> FEATURE:
<223> OTHER INFORMATION: Synthetic

<400> SEQUENCE: 417

Ser Ser Gly Glu Asp Phe Leu Ile Asn Arg Gln Ile Tyr Ile Leu His
1               5                   10                  15

Pro Arg Gly Val Lys Phe Thr Asp Thr Ala Val Ala Asp Val Phe Pro
            20                  25                  30

Thr Asn Ala Glu Leu
        35

<210> SEQ ID NO 418
<211> LENGTH: 38
<212> TYPE: PRT
<213> ORGANISM: Artificial Sequence
<220> FEATURE:
<223> OTHER INFORMATION: Synthetic

<400> SEQUENCE: 418

Lys Gly Asn Asp Glu Val Tyr Thr Arg Arg Ala Phe Thr Met His Pro
1               5                   10                  15
```

Tyr Gly Val Lys Phe Thr Asn Ala Asp Arg Asp Ser Gly Glu Ile Thr
            20                  25                  30

Pro Thr Asn Lys Asp Leu
        35

<210> SEQ ID NO 419
<211> LENGTH: 38
<212> TYPE: PRT
<213> ORGANISM: Artificial Sequence
<220> FEATURE:
<223> OTHER INFORMATION: Synthetic

<400> SEQUENCE: 419

Lys Gly Asn Asp Glu Val Tyr Thr Arg Arg Ala Phe Thr Met His Pro
1               5                   10                  15

Tyr Gly Val Lys Phe Thr Asn Ile Glu Arg Glu Glu Gly Glu Ile Thr
            20                  25                  30

Pro Thr Asn Asn Asp Leu
        35

<210> SEQ ID NO 420
<211> LENGTH: 39
<212> TYPE: PRT
<213> ORGANISM: Artificial Sequence
<220> FEATURE:
<223> OTHER INFORMATION: Synthetic

<400> SEQUENCE: 420

Ala Lys Gly Asn Asp Met Ile Tyr Thr Arg Arg Ala Leu Val Met His
1               5                   10                  15

Pro Tyr Gly Val Lys Trp Thr Gly Ala Glu Val Asp Ala Gly Asn Ile
            20                  25                  30

Thr Pro Ser Asn Ala Asp Leu
        35

<210> SEQ ID NO 421
<211> LENGTH: 39
<212> TYPE: PRT
<213> ORGANISM: Artificial Sequence
<220> FEATURE:
<223> OTHER INFORMATION: Synthetic

<400> SEQUENCE: 421

Ala Lys Gly Asn Asp Gln Val Phe Thr Arg Arg Ala Phe Thr Met His
1               5                   10                  15

Pro Tyr Gly Val Lys Phe Lys Asn Ala Val Arg Asp Ala Asn Glu Ile
            20                  25                  30

Thr Pro Thr Asn Ala Asp Leu
        35

<210> SEQ ID NO 422
<211> LENGTH: 39
<212> TYPE: PRT
<213> ORGANISM: Artificial Sequence
<220> FEATURE:
<223> OTHER INFORMATION: Synthetic

<400> SEQUENCE: 422

Ala Lys Gly Asn Asp Gln Val Phe Thr Arg Arg Ala Phe Thr Met His
1               5                   10                  15

Pro Tyr Gly Val Lys Phe Thr Asn Ala Asp Arg Glu Ala Gly Glu Ile
            20                  25                  30

Thr Pro Thr Asn Lys Asp Leu
        35

<210> SEQ ID NO 423
<211> LENGTH: 39
<212> TYPE: PRT
<213> ORGANISM: Artificial Sequence
<220> FEATURE:
<223> OTHER INFORMATION: Synthetic

<400> SEQUENCE: 423

Ala Lys Gly Asn Asp Gln Val Phe Thr Arg Arg Ala Ile Thr Met His
1               5                   10                  15

Pro Tyr Gly Ile Lys Trp Thr Asp Asn Leu Arg Asp Asp Gly Asn Ile
            20                  25                  30

Thr Pro Thr Asn Val Asp Leu
        35

<210> SEQ ID NO 424
<211> LENGTH: 39
<212> TYPE: PRT
<213> ORGANISM: Artificial Sequence
<220> FEATURE:
<223> OTHER INFORMATION: Synthetic

<400> SEQUENCE: 424

Ala Lys Gly Asn Asp Gln Val Phe Thr Arg Arg Ala Ile Thr Met His
1               5                   10                  15

Pro Tyr Gly Ile Lys Trp Thr Asp Asn Leu Arg Glu Glu Gly Asn Ile
            20                  25                  30

Thr Pro Thr Asn Val Asp Leu
        35

<210> SEQ ID NO 425
<211> LENGTH: 39
<212> TYPE: PRT
<213> ORGANISM: Artificial Sequence
<220> FEATURE:
<223> OTHER INFORMATION: Synthetic

<400> SEQUENCE: 425

Ala Lys Gly Asn Asp Gln Val Phe Thr Arg Arg Ala Ile Thr Met His
1               5                   10                  15

Pro Tyr Gly Ile Lys Trp Thr Glu Asn Leu Arg Glu Glu Gly Asn Ile
            20                  25                  30

Thr Pro Thr Asn Val Asp Leu
        35

<210> SEQ ID NO 426
<211> LENGTH: 39
<212> TYPE: PRT
<213> ORGANISM: Artificial Sequence
<220> FEATURE:
<223> OTHER INFORMATION: Synthetic

<400> SEQUENCE: 426

Ala Lys Gly Asn Asp Arg Ile Phe Thr Arg Trp Ala Leu Thr Met His
1               5                   10                  15

Pro Tyr Gly Val Lys Trp Asn Asp Ser Thr Arg Glu Asp Gly Asn Ile
            20                  25                  30

Thr Pro Thr Asn Val Asp Leu
        35

```
<210> SEQ ID NO 427
<211> LENGTH: 39
<212> TYPE: PRT
<213> ORGANISM: Artificial Sequence
<220> FEATURE:
<223> OTHER INFORMATION: Synthetic

<400> SEQUENCE: 427

Ala Lys Gly Asn Asn Asn Ile Phe Thr Arg Arg Ala Phe Thr Met His
1               5                   10                  15

Pro Tyr Gly Val Lys Phe Thr Asn Ala Ala Arg Glu Ser Gly Phe Ile
            20                  25                  30

Thr Pro Thr Asn Lys Asp Leu
        35

<210> SEQ ID NO 428
<211> LENGTH: 39
<212> TYPE: PRT
<213> ORGANISM: Artificial Sequence
<220> FEATURE:
<223> OTHER INFORMATION: Synthetic

<400> SEQUENCE: 428

Ala Lys Gly Thr Asp Ile Ile Tyr Thr Arg Arg Ala Val Thr Met His
1               5                   10                  15

Pro Tyr Gly Val Lys Trp Lys Asp Ala Glu Arg Glu Ala Gly Asn Met
            20                  25                  30

Thr Pro Thr Asn Val Asp Leu
        35

<210> SEQ ID NO 429
<211> LENGTH: 39
<212> TYPE: PRT
<213> ORGANISM: Artificial Sequence
<220> FEATURE:
<223> OTHER INFORMATION: Synthetic

<400> SEQUENCE: 429

Asn Lys Gly Asn Asp Glu Val Tyr Thr Arg Arg Ala Phe Thr Met His
1               5                   10                  15

Pro Tyr Gly Val Lys Phe Thr Asn Thr Asp Arg Glu Ser Gly Glu Ile
            20                  25                  30

Thr Pro Thr Asn Lys Asp Leu
        35

<210> SEQ ID NO 430
<211> LENGTH: 39
<212> TYPE: PRT
<213> ORGANISM: Artificial Sequence
<220> FEATURE:
<223> OTHER INFORMATION: Synthetic

<400> SEQUENCE: 430

Ser Lys Gly Asn Asp Gln Val Phe Thr Arg Arg Ala Phe Thr Met His
1               5                   10                  15

Pro Tyr Gly Val Lys Phe Lys Asn Ala Val Arg Asp Val Asn Glu Ile
            20                  25                  30

Thr Pro Thr Asn Ala Asp Leu
        35

<210> SEQ ID NO 431
<211> LENGTH: 39
```

<212> TYPE: PRT
<213> ORGANISM: Artificial Sequence
<220> FEATURE:
<223> OTHER INFORMATION: Synthetic

<400> SEQUENCE: 431

Ser Lys Gly Asn Asp Gln Val Phe Thr Arg Arg Ala Phe Thr Met His
1               5                   10                  15
Pro Tyr Gly Val Lys Phe Lys Asn Ala Val Arg Asp Ala Asn Asp Ile
            20                  25                  30
Thr Pro Thr Asn Ala Glu Leu
        35

<210> SEQ ID NO 432
<211> LENGTH: 40
<212> TYPE: PRT
<213> ORGANISM: Artificial Sequence
<220> FEATURE:
<223> OTHER INFORMATION: Synthetic

<400> SEQUENCE: 432

Asp Gly Thr Ser Tyr Val Ser Ser Thr Ala Ser Pro Tyr Ser Ala Thr
1               5                   10                  15
Glu Asn Ser Thr Leu Lys Gly Ile Glu Leu Ile Tyr Lys Phe Pro Leu
            20                  25                  30
Ala Ala Met Asn Ser Leu Lys Thr
        35                  40

<210> SEQ ID NO 433
<211> LENGTH: 44
<212> TYPE: PRT
<213> ORGANISM: Artificial Sequence
<220> FEATURE:
<223> OTHER INFORMATION: Synthetic

<400> SEQUENCE: 433

Asp Asp Gly Ser Ser Thr Ala Ser Ala Ala Ser Val Ser Tyr Arg Val
1               5                   10                  15
Asp Gly Ala Pro Gly Ala Gln Val Ala Thr Ile Thr Leu Glu Arg Pro
            20                  25                  30
Glu Ala Met Asn Gly Leu Asp Thr Glu Thr Lys Asp
        35                  40

<210> SEQ ID NO 434
<211> LENGTH: 50
<212> TYPE: PRT
<213> ORGANISM: Artificial Sequence
<220> FEATURE:
<223> OTHER INFORMATION: Synthetic

<400> SEQUENCE: 434

Tyr Val Ile Thr Gly Ser Val Asn Pro Lys Arg Phe Ala Tyr Thr Glu
1               5                   10                  15
Arg Gly Asn Thr Gln Ile Val Ile Arg Glu Pro Phe Thr Asp His Pro
            20                  25                  30
Ile Tyr Asp Ala Phe Lys Asp Cys Phe Tyr Asp Ala Tyr Asp Leu Glu
        35                  40                  45
Leu Asp
    50

<210> SEQ ID NO 435
<211> LENGTH: 67

```
<212> TYPE: PRT
<213> ORGANISM: Artificial Sequence
<220> FEATURE:
<223> OTHER INFORMATION: Synthetic

<400> SEQUENCE: 435

Tyr Val Phe Gln Gly Gln Gly Asn Asp His Arg Phe Thr Thr Arg Pro
1               5                   10                  15

Phe Val Thr Gly Ser Lys Lys Phe Leu Phe Lys Asn Gln Val Arg Asp
            20                  25                  30

Asn Met Ile Arg Thr Leu Thr Ser Ala Val Pro Ile Ile Thr Gly Tyr
        35                  40                  45

Glu Val Phe Thr Tyr Trp Ala Phe Ala Asn Gly Tyr Leu Gly Leu Phe
    50                  55                  60

Asp Leu Gly
65

<210> SEQ ID NO 436
<211> LENGTH: 69
<212> TYPE: PRT
<213> ORGANISM: Artificial Sequence
<220> FEATURE:
<223> OTHER INFORMATION: Synthetic

<400> SEQUENCE: 436

Tyr Val Phe Gln Gly Gln Gly Asn Asp His Arg Phe Thr Thr Arg Pro
1               5                   10                  15

Phe Ala Thr Gly Ser Lys Lys Phe Leu Phe Lys Asn Gln Val Arg Asp
            20                  25                  30

Asn Met Ile Arg Thr Leu Ala Ser Ala Val Pro Ile Ile Thr Gly Tyr
        35                  40                  45

Glu Val Phe Thr Tyr Trp Ala Phe Ala Asn Gly Tyr Leu Gly Leu Phe
    50                  55                  60

Asp Leu Gly Ser Ser
65
```